US011382744B2

(12) United States Patent
Siegel et al.

(10) Patent No.: US 11,382,744 B2
(45) Date of Patent: Jul. 12, 2022

(54) STEERABLE DELIVERY CATHETER

(71) Applicant: Edwards Lifesciences Corporation, Irvine, CA (US)

(72) Inventors: Alexander J. Siegel, Irvine, CA (US); David M. Taylor, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 185 days.

(21) Appl. No.: 16/182,955

(22) Filed: Nov. 7, 2018

(65) Prior Publication Data

US 2019/0070003 A1    Mar. 7, 2019

Related U.S. Application Data

(63) Continuation of application No. 15/984,661, filed on May 21, 2018, which is a continuation of application No. PCT/US2017/066854, filed on Dec. 15, 2017.

(60) Provisional application No. 62/435,563, filed on Dec. 16, 2016.

(51) Int. Cl.
*A61F 2/24* (2006.01)

(52) U.S. Cl.
CPC .......... *A61F 2/2436* (2013.01); *A61F 2/2409* (2013.01); *A61F 2/2418* (2013.01); *A61F 2/2412* (2013.01); *A61F 2210/0014* (2013.01); *A61F 2220/0008* (2013.01)

(58) Field of Classification Search
CPC ...... A61F 2/2427; A61F 2/243; A61F 2/2451; A61F 2/2466; A61M 25/0054; A61M 25/0138; A61M 25/0147; A61M 25/0105; A61M 2025/015; A61M 2025/0161; A61B 1/0055; A61B 1/0056; A61B 1/0057; A61B 1/008; A61B 2017/003; A61B 2017/0035; A61B 2017/0039; A61B 2017/00314; A61B 2017/00318; A61B 2017/00323
See application file for complete search history.

(56) References Cited

U.S. PATENT DOCUMENTS

| 4,035,849 | A | 7/1977 | Angell et al. |
| 4,592,340 | A | 6/1986 | Boyles |
| 4,994,077 | A | 2/1991 | Dobben |
| 5,059,177 | A | 10/1991 | Towne et al. |
| 5,350,397 | A | 9/1994 | Palermo et al. |
| 5,411,552 | A | 5/1995 | Andersen et al. |
| 5,554,185 | A | 9/1996 | Block et al. |
| 5,591,195 | A | 1/1997 | Taheri et al. |
| 5,599,305 | A | 2/1997 | Hermann et al. |

(Continued)

FOREIGN PATENT DOCUMENTS

| DE | 19532846 A1 | 3/1997 |
| DE | 19907646 A1 | 8/2000 |

(Continued)

OTHER PUBLICATIONS

US 8,470,027 B2, 06/2013, Keranen (withdrawn)

*Primary Examiner* — Robert A Lynch
(74) *Attorney, Agent, or Firm* — Linda A. Nassif

(57) ABSTRACT

Tools and methods are provided for delivering a device to a native valve of a patient's heart. A catheter can include a flexible tube, a plurality of links, and a control wire. Applying tension to the control wire pulls on the links, which causes links to bend the flexible tube.

41 Claims, 39 Drawing Sheets

(56) References Cited

U.S. PATENT DOCUMENTS

| | | | |
|---|---|---|---|
| 5,639,274 A | 6/1997 | Fischell et al. | |
| 5,728,068 A | 3/1998 | Leone et al. | |
| 5,772,578 A * | 6/1998 | Heimberger | A61B 1/0056 |
| | | | 600/139 |
| 5,840,081 A | 11/1998 | Andersen et al. | |
| 5,968,068 A | 10/1999 | Dehdashtian et al. | |
| 6,168,614 B1 | 1/2001 | Andersen et al. | |
| 6,217,585 B1 | 4/2001 | Houser et al. | |
| 6,379,372 B1 | 4/2002 | Dehdashtian et al. | |
| 6,419,696 B1 | 7/2002 | Ortiz et al. | |
| 6,432,134 B1 | 8/2002 | Anson et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,527,979 B2 | 3/2003 | Constantz et al. | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,730,121 B2 | 5/2004 | Ortiz et al. | |
| 6,733,525 B2 | 5/2004 | Yang et al. | |
| 6,767,362 B2 | 7/2004 | Schreck | |
| 6,797,001 B2 | 9/2004 | Mathis et al. | |
| 6,797,002 B2 | 9/2004 | Spence et al. | |
| 6,830,584 B1 | 12/2004 | Seguin | |
| 6,893,460 B2 | 5/2005 | Spenser et al. | |
| 6,908,481 B2 | 6/2005 | Cribier | |
| 7,004,176 B2 | 2/2006 | Lau | |
| 7,018,406 B2 | 3/2006 | Seguin et al. | |
| 7,018,408 B2 | 3/2006 | Bailey et al. | |
| 7,037,334 B1 | 5/2006 | Hlavka et al. | |
| 7,077,861 B2 | 7/2006 | Spence | |
| 7,101,395 B2 | 9/2006 | Fremulis et al. | |
| 7,125,421 B2 | 10/2006 | Fremulis et al. | |
| 7,226,477 B2 | 6/2007 | Cox | |
| 7,276,084 B2 | 10/2007 | Yang et al. | |
| 7,318,278 B2 | 1/2008 | Zhang et al. | |
| 7,374,571 B2 | 5/2008 | Pease et al. | |
| 7,393,360 B2 | 7/2008 | Spenser et al. | |
| 7,510,575 B2 | 3/2009 | Spenser et al. | |
| 7,585,321 B2 | 9/2009 | Cribier | |
| 7,618,446 B2 | 11/2009 | Andersen et al. | |
| 7,708,775 B2 | 5/2010 | Rowe et al. | |
| 7,737,060 B2 | 6/2010 | Strickler et al. | |
| 7,780,723 B2 | 8/2010 | Taylor | |
| 7,785,366 B2 | 8/2010 | Maurer et al. | |
| 7,951,195 B2 | 5/2011 | Antonsson et al. | |
| 7,959,661 B2 | 6/2011 | Hijlkema et al. | |
| 7,993,397 B2 | 8/2011 | Lashinski et al. | |
| 8,029,556 B2 | 10/2011 | Rowe | |
| 8,167,932 B2 | 5/2012 | Bourang et al. | |
| 8,323,335 B2 | 12/2012 | Rowe et al. | |
| 8,377,115 B2 | 2/2013 | Thompson | |
| 8,398,708 B2 | 3/2013 | Meiri et al. | |
| 8,449,605 B2 | 5/2013 | Lichtenstein et al. | |
| 8,449,606 B2 | 5/2013 | Eliasen et al. | |
| 8,518,107 B2 | 8/2013 | Tsukashima et al. | |
| 8,657,872 B2 | 2/2014 | Seguin | |
| 8,663,322 B2 | 3/2014 | Keranen | |
| 8,672,998 B2 | 3/2014 | Lichtenstein et al. | |
| 8,734,507 B2 | 5/2014 | Keranen | |
| 8,864,823 B2 | 10/2014 | Cartledge et al. | |
| 9,078,747 B2 | 7/2015 | Conklin | |
| 9,095,434 B2 | 8/2015 | Rowe | |
| 9,119,718 B2 | 9/2015 | Keranen | |
| 9,237,886 B2 | 1/2016 | Seguin et al. | |
| 9,364,326 B2 | 6/2016 | Yaron | |
| 9,463,268 B2 | 10/2016 | Spence | |
| 9,474,599 B2 | 10/2016 | Keranen | |
| 9,622,863 B2 | 4/2017 | Karapetian et al. | |
| 2002/0032481 A1 | 3/2002 | Gabbay | |
| 2003/0050694 A1 | 3/2003 | Yang et al. | |
| 2003/0225420 A1 | 12/2003 | Wardle | |
| 2004/0073141 A1 | 4/2004 | Hartley et al. | |
| 2004/0133220 A1 * | 7/2004 | Lashinski | A61F 2/2466 |
| | | | 606/151 |
| 2004/0133263 A1 | 7/2004 | Dusbabek et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0080474 A1 | 4/2005 | Andreas et al. | |
| 2005/0096736 A1 | 5/2005 | Osse et al. | |
| 2005/0119735 A1 | 6/2005 | Spence et al. | |
| 2005/0137691 A1 | 6/2005 | Salahieh et al. | |
| 2005/0182486 A1 | 8/2005 | Gabbay | |
| 2005/0203614 A1 | 9/2005 | Forster et al. | |
| 2005/0203617 A1 | 9/2005 | Forster et al. | |
| 2006/0025857 A1 | 2/2006 | Bergheim et al. | |
| 2007/0005131 A1 | 1/2007 | Taylor | |
| 2007/0027533 A1 | 2/2007 | Douk | |
| 2007/0083226 A1 | 4/2007 | Buiser et al. | |
| 2007/0203575 A1 | 8/2007 | Forster et al. | |
| 2007/0225681 A1 | 9/2007 | House | |
| 2007/0265700 A1 | 11/2007 | Eliasen et al. | |
| 2008/0033542 A1 | 2/2008 | Antonsson et al. | |
| 2008/0125853 A1 | 5/2008 | Bailey et al. | |
| 2008/0208330 A1 | 8/2008 | Keranen | |
| 2008/0287741 A1 | 11/2008 | Ostrovsky et al. | |
| 2008/0294230 A1 | 11/2008 | Parker | |
| 2009/0088836 A1 | 4/2009 | Bishop et al. | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0319037 A1 | 12/2009 | Rowe et al. | |
| 2010/0049313 A1 | 2/2010 | Alon et al. | |
| 2010/0145440 A1 | 6/2010 | Keranen | |
| 2010/0185172 A1 | 7/2010 | Fabro | |
| 2010/0198347 A1 | 8/2010 | Zakay et al. | |
| 2010/0312333 A1 | 12/2010 | Navia et al. | |
| 2010/0318184 A1 | 12/2010 | Spence | |
| 2011/0015729 A1 | 1/2011 | Jimenez et al. | |
| 2012/0059458 A1 | 3/2012 | Buchbinder et al. | |
| 2012/0123529 A1 | 5/2012 | Levi et al. | |
| 2012/0158021 A1 | 6/2012 | Morrill | |
| 2012/0283820 A1 | 11/2012 | Tseng et al. | |
| 2013/0006352 A1 | 1/2013 | Yaron | |
| 2013/0226289 A1 | 8/2013 | Shaolian et al. | |
| 2013/0317598 A1 | 11/2013 | Rowe et al. | |
| 2013/0345765 A1 | 12/2013 | Brockman et al. | |
| 2014/0074299 A1 | 3/2014 | Endou et al. | |
| 2014/0135685 A1 | 5/2014 | Kabe et al. | |
| 2014/0135913 A1 | 5/2014 | Lichtenstein et al. | |
| 2014/0172070 A1 | 6/2014 | Seguin | |
| 2014/0276966 A1 * | 9/2014 | Ranucci | A61M 25/0138 |
| | | | 606/139 |
| 2014/0309661 A1 * | 10/2014 | Sheps | A61M 25/01 |
| | | | 606/130 |
| 2014/0379074 A1 | 12/2014 | Spence et al. | |
| 2015/0230921 A1 | 8/2015 | Chau et al. | |
| 2015/0282931 A1 | 10/2015 | Brunnett et al. | |
| 2015/0305867 A1 | 10/2015 | Liu et al. | |
| 2015/0335428 A1 | 11/2015 | Keranen | |
| 2015/0374493 A1 | 12/2015 | Yaron et al. | |
| 2016/0074165 A1 | 3/2016 | Spence et al. | |
| 2016/0095705 A1 | 4/2016 | Keranen et al. | |
| 2016/0158497 A1 * | 6/2016 | Tran | A61F 2/2436 |
| | | | 623/2.11 |
| 2016/0184095 A1 | 6/2016 | Spence et al. | |
| 2016/0199177 A1 | 7/2016 | Spence et al. | |
| 2016/0256276 A1 | 9/2016 | Yaron | |
| 2017/0007399 A1 | 1/2017 | Keranen | |
| 2017/0007402 A1 | 1/2017 | Zerkowski et al. | |
| 2017/0217385 A1 | 8/2017 | Rinkleff et al. | |

FOREIGN PATENT DOCUMENTS

| | | |
|---|---|---|
| DE | 102010034345 A1 | 2/2012 |
| EP | 092410 A1 | 4/1994 |
| EP | 0850607 A1 | 7/1998 |
| EP | 1432369 A1 | 6/2004 |
| EP | 1521550 A2 | 4/2005 |
| EP | 1296618 B1 | 1/2008 |
| EP | 1827314 B1 | 12/2010 |
| EP | 2620125 A1 | 7/2013 |
| EP | 2726018 A2 | 5/2014 |

(56) References Cited

FOREIGN PATENT DOCUMENTS

| | | | |
|---|---|---|---|
| EP | 2806829 | A2 | 12/2014 |
| FR | 2815844 | A1 | 5/2002 |
| WO | 9117720 | A1 | 11/1991 |
| WO | 9829057 | A1 | 7/1998 |
| WO | 0149213 | A2 | 7/2001 |
| WO | 0154625 | A1 | 8/2001 |
| WO | 0176510 | A2 | 10/2001 |
| WO | 0222054 | A1 | 3/2002 |
| WO | 0236048 | A1 | 5/2002 |
| WO | 0247575 | A2 | 6/2002 |
| WO | 03047468 | A1 | 6/2003 |
| WO | 2005084595 | A1 | 9/2005 |
| WO | 2005102015 | A2 | 11/2005 |
| WO | 2006011127 | A2 | 2/2006 |
| WO | 2006032051 | A2 | 3/2006 |
| WO | 2006111391 | A1 | 10/2006 |
| WO | 2006138173 | A2 | 12/2006 |
| WO | 2007033360 | A2 | 3/2007 |
| WO | 2007047488 | A2 | 4/2007 |
| WO | 2007067942 | A1 | 6/2007 |
| WO | 2010075245 | A2 | 7/2010 |
| WO | 2010121076 | A2 | 10/2010 |
| WO | 2013069019 | A2 | 5/2013 |
| WO | 2013110722 | A2 | 8/2013 |
| WO | 2013114214 | A2 | 8/2013 |
| WO | 2014145399 | A1 | 9/2014 |
| WO | 2015023579 | A1 | 2/2015 |
| WO | 2015023862 | A2 | 2/2015 |
| WO | 2015127264 | A1 | 8/2015 |
| WO | 2015198125 | A1 | 12/2015 |
| WO | 2016038017 | A1 | 3/2016 |
| WO | 2016040881 | A1 | 3/2016 |
| WO | 2016090025 | A1 | 6/2016 |
| WO | 2016130820 | A1 | 8/2016 |

\* cited by examiner

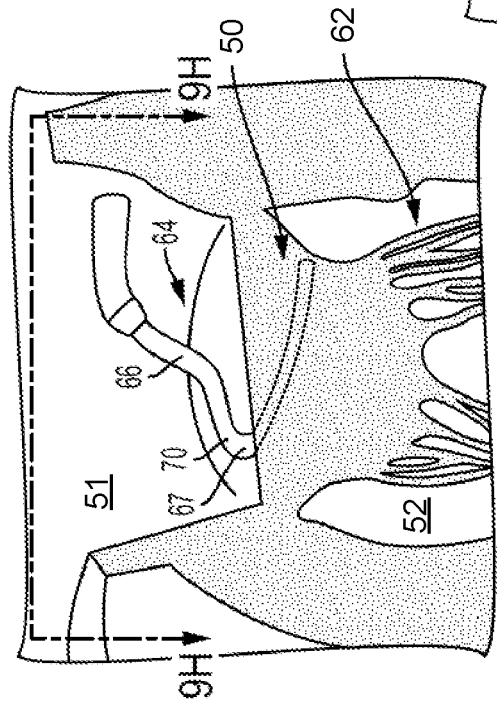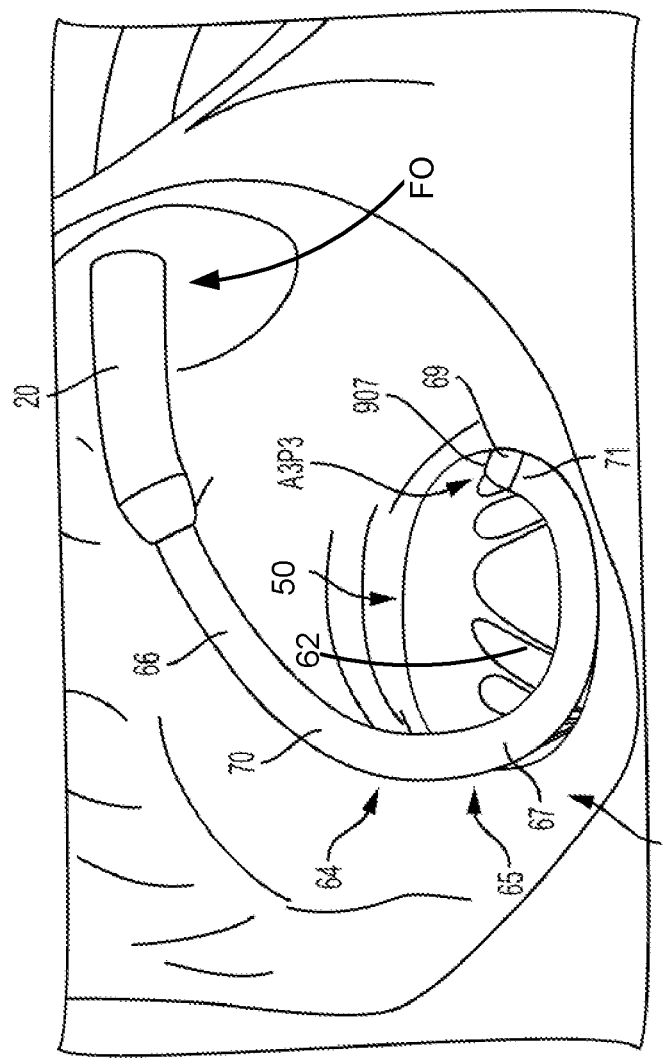

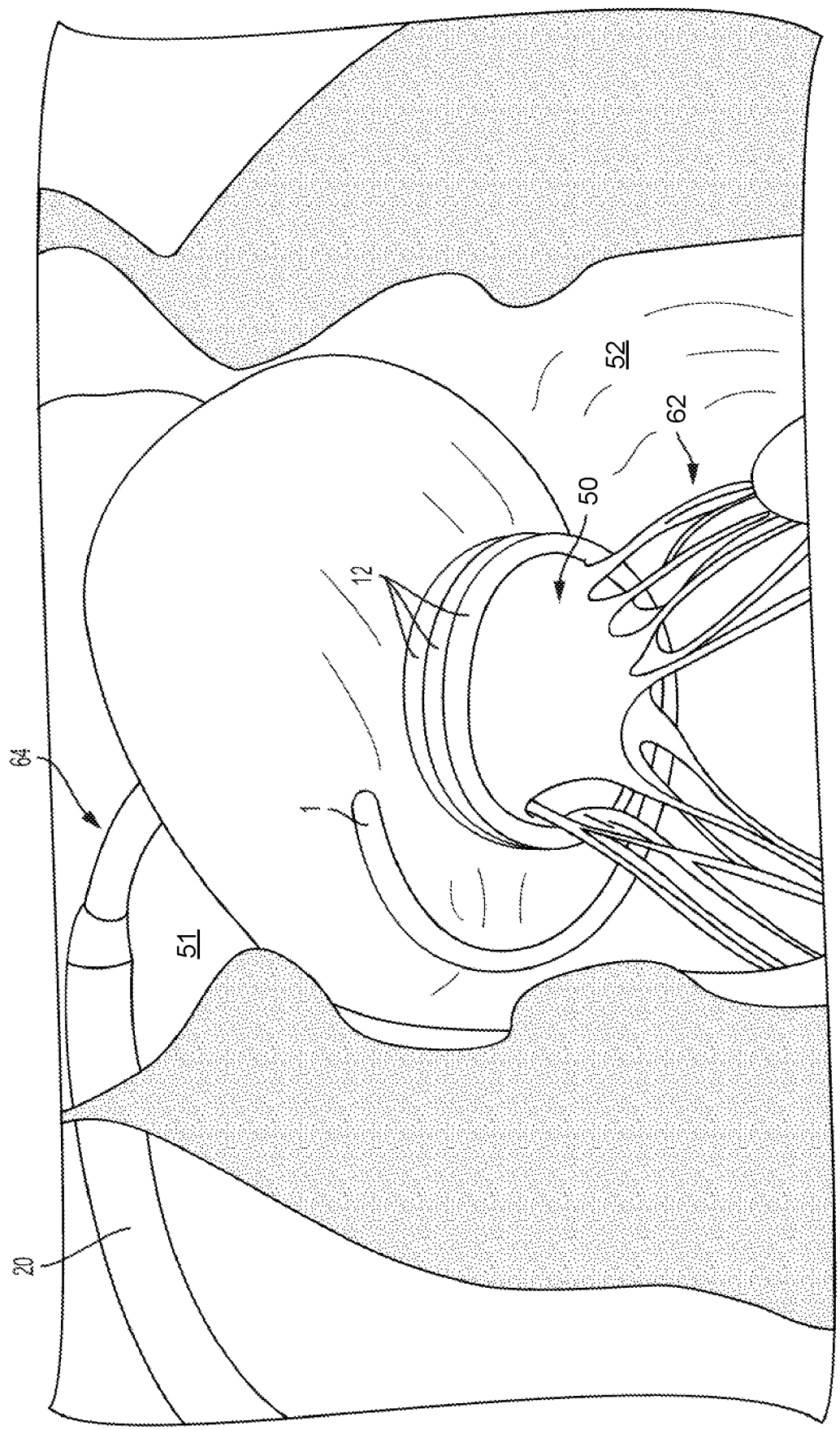

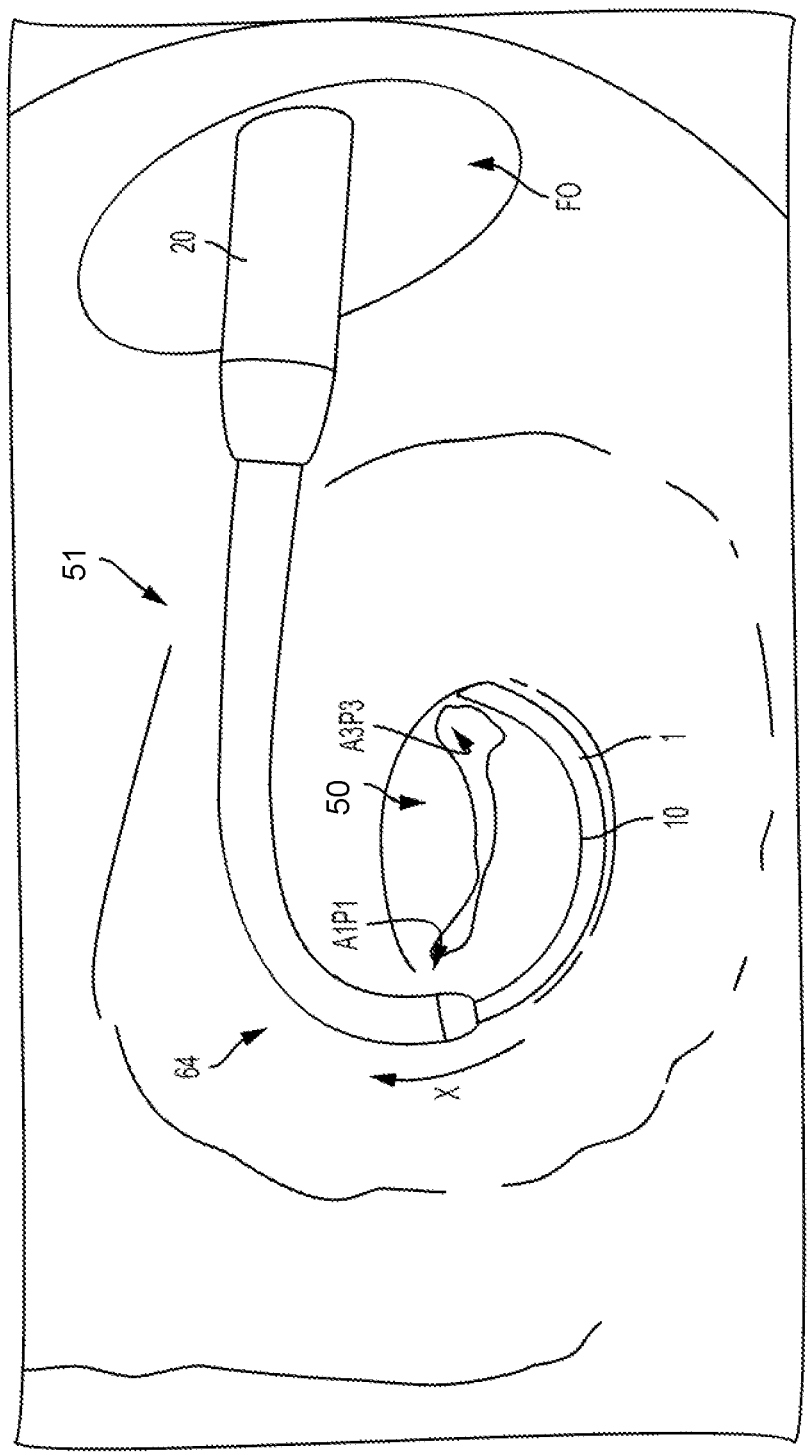

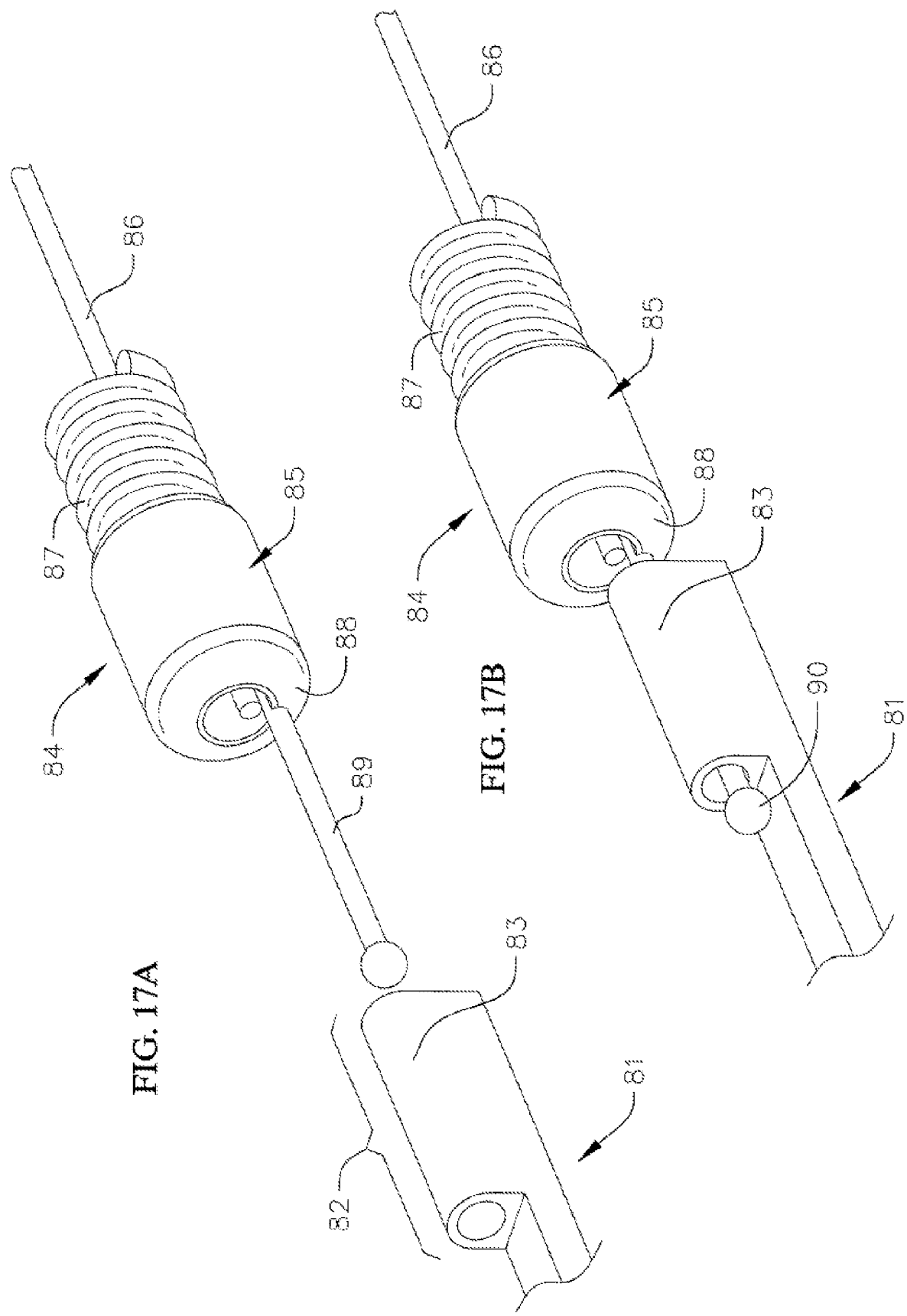

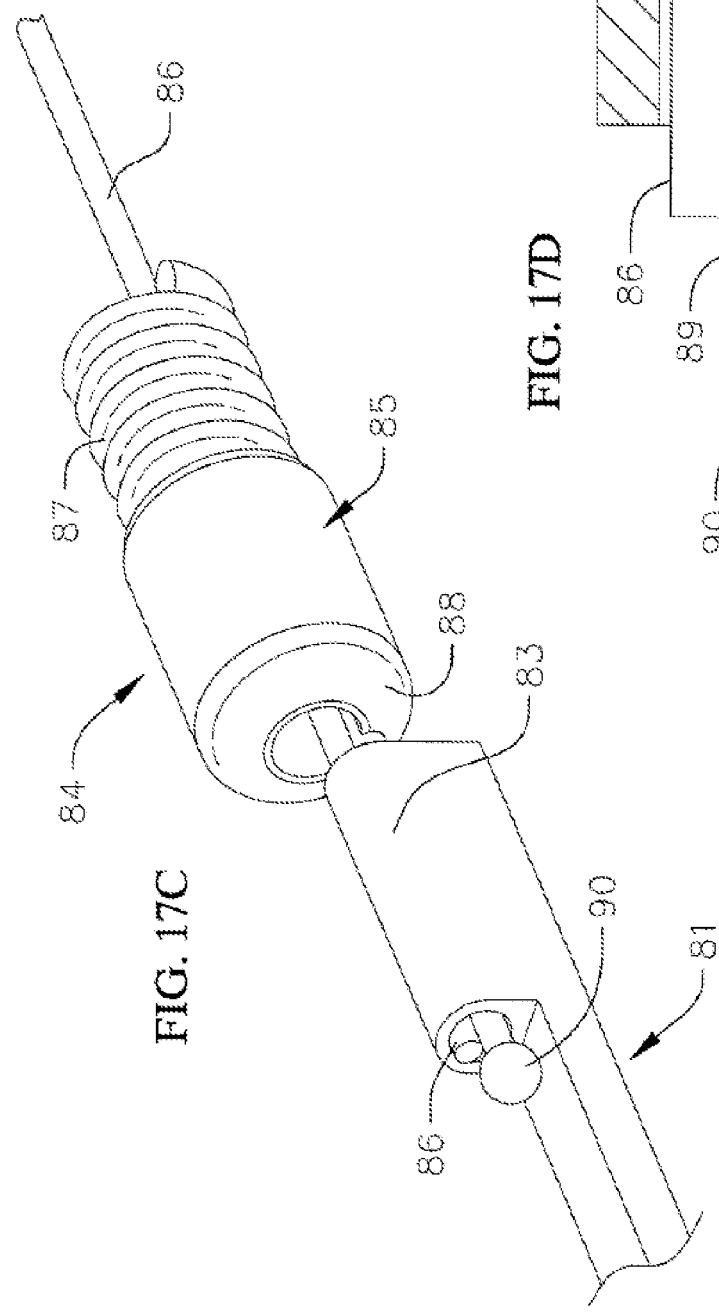
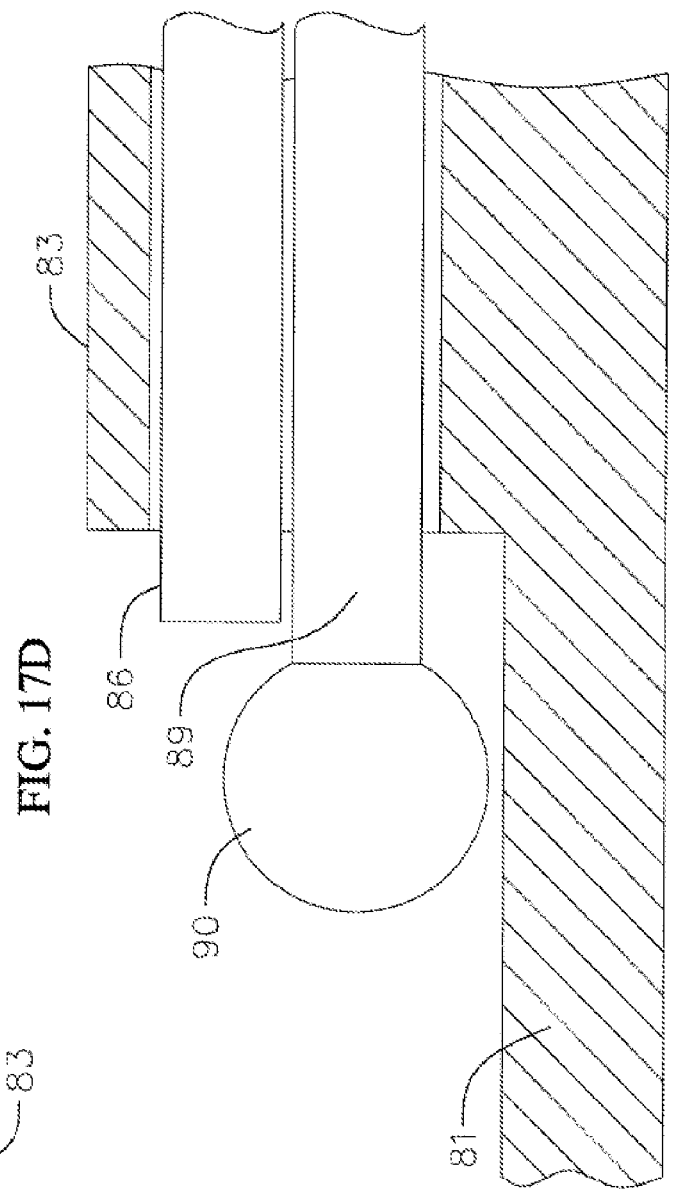
FIG. 17C
FIG. 17D

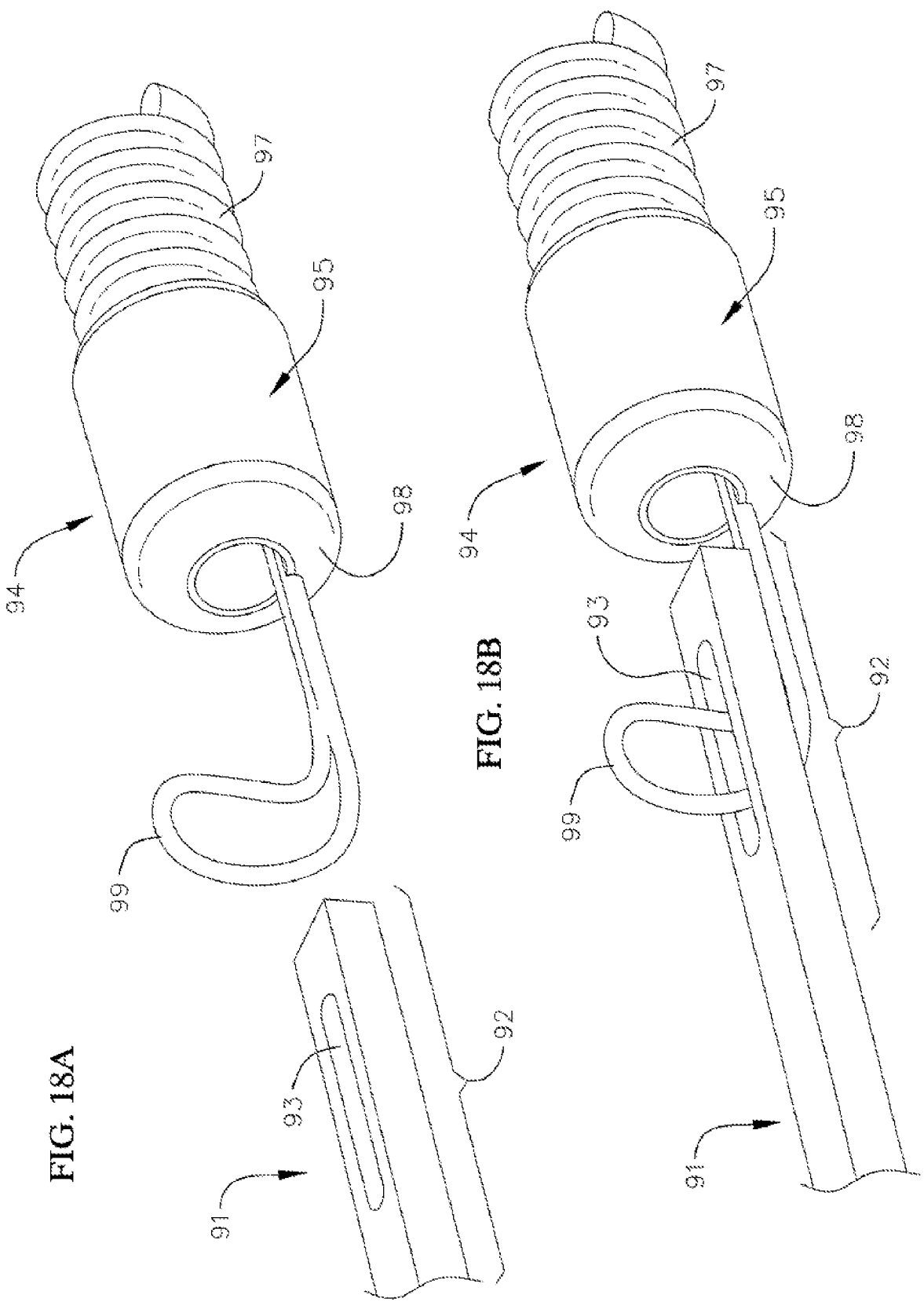

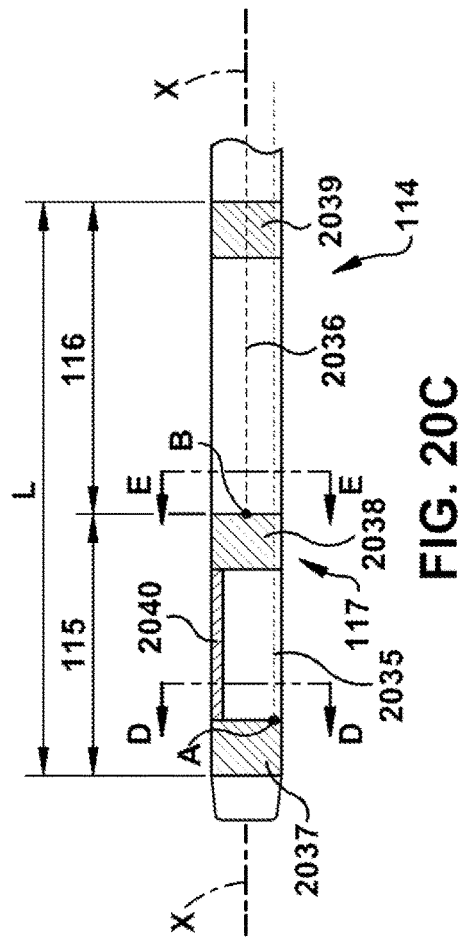
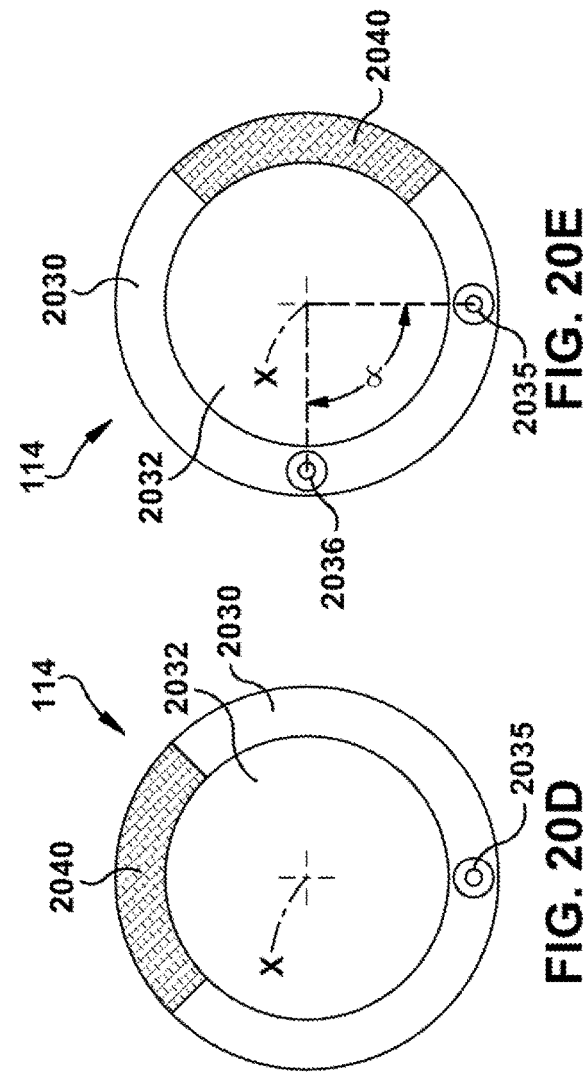
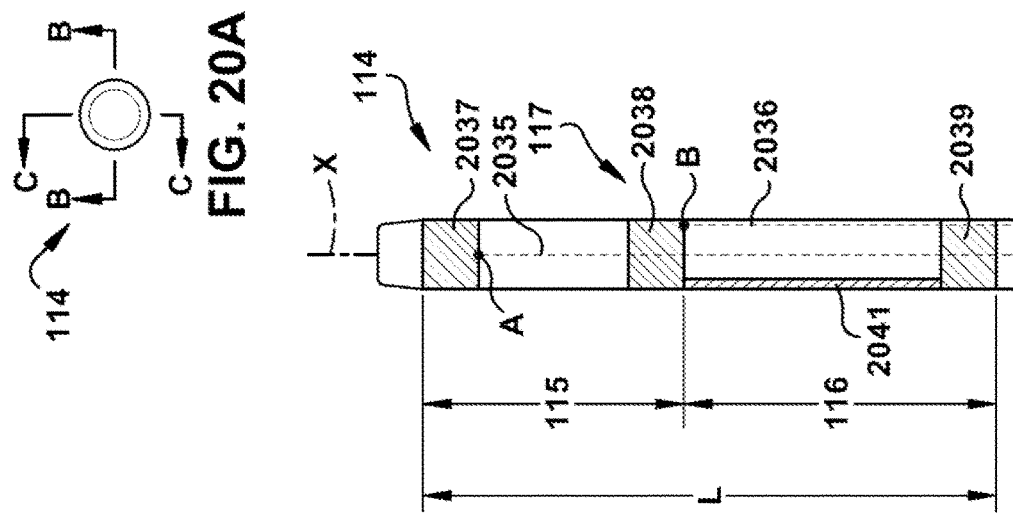

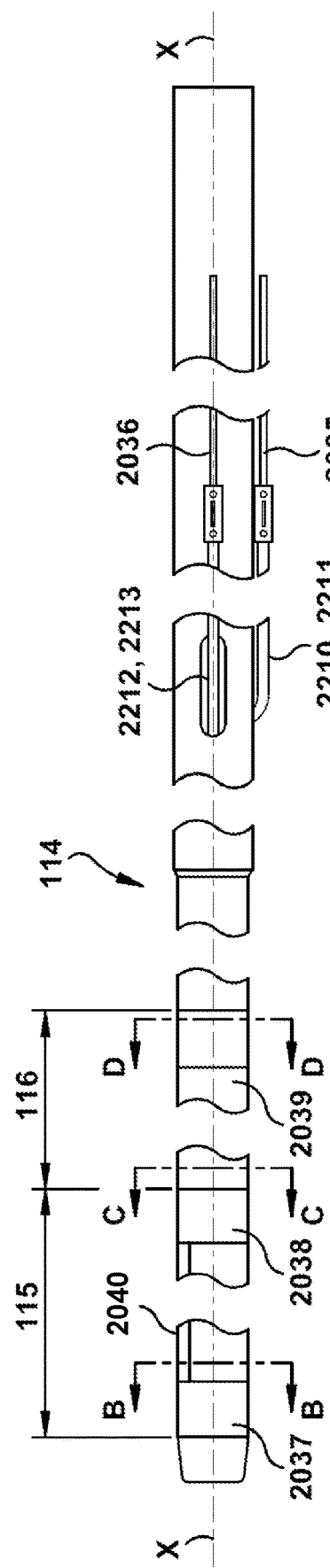
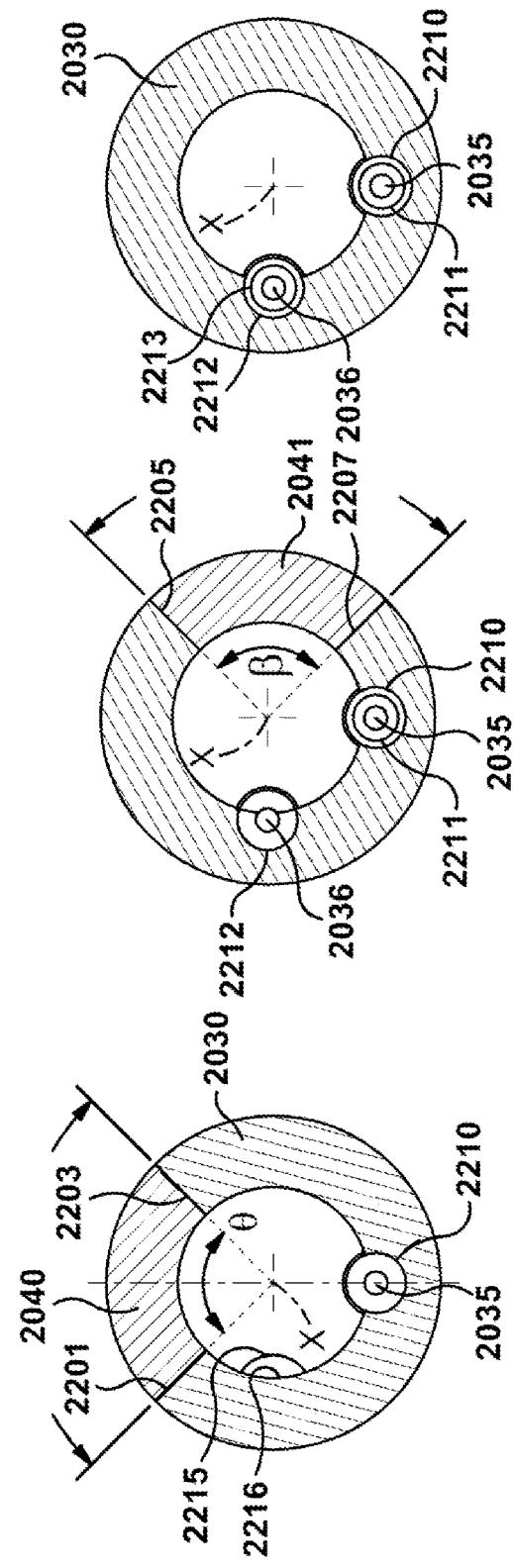
FIG. 22A
FIG. 22B
FIG. 22C
FIG. 22D

STEERABLE DELIVERY CATHETER

RELATED APPLICATIONS

The present application is a continuation of U.S. patent application Ser. No. 15/984,661 titled "DEPLOYMENT SYSTEMS, TOOLS, AND METHODS FOR DELIVERING AN ANCHORING DEVICE FOR A PROSTHETIC VALVE, filed on May 21, 2018, which is a continuation of PCT Patent Application Serial No. PCT/US2017/066854 titled "DEPLOYMENT SYSTEMS, TOOLS, AND METHODS FOR DELIVERING AN ANCHORING DEVICE FOR A PROSTHETIC VALVE" filed on Dec. 15, 2017, which claims the benefit of U.S. Provisional Patent Application Ser. No. 62/435,563, filed on Dec. 16, 2016, and titled "DEPLOYMENT TOOLS AND METHODS FOR DELIVERING AN ANCHORING DEVICE FOR A PROSTHETIC VALVE AT A NATIVE VALVE ANNULUS," all of which are incorporated herein by reference in their entireties.

FIELD

The present disclosure generally concerns deployment tools for delivering anchoring devices, such as prostheses docking devices that support prostheses and methods of using the same. For example, the disclosure relates to replacement of heart valves that have malformations and/or dysfunctions, where a flexible delivery catheter is utilized to deploy anchoring devices that support a prosthetic heart valve at an implant site, and methods of using the delivery catheter to implant such anchoring devices and/or prosthetic heart valves.

BACKGROUND

Referring generally to FIGS. 1A-1B, the native mitral valve 50 controls the flow of blood from the left atrium 51 to the left ventricle 52 of the human heart and, similarly, the tricuspid valve 59 controls the flow of blood between the right atrium 56 and the right ventricle 61. The mitral valve has a different anatomy than other native heart valves. The mitral valve includes an annulus made up of native valve tissue surrounding the mitral valve orifice, and a pair of cusps or leaflets extending downward from the annulus into the left ventricle. The mitral valve annulus can form a "D" shaped, oval shaped, or otherwise non-circular cross-sectional shape having major and minor axes. An anterior leaflet can be larger than a posterior leaflet of the valve, forming a generally "C" shaped boundary between the abutting free edges of the leaflets when they are closed together.

When operating properly, the anterior leaflet 54 and the posterior leaflet 53 of the mitral valve function together as a one-way valve to allow blood to flow from the left atrium 51 to the left ventricle 52. After the left atrium receives oxygenated blood from the pulmonary veins, the muscles of the left atrium contract and the left ventricle relaxes (also referred to as "ventricular diastole" or "diastole"), and the oxygenated blood that is collected in the left atrium flows into the left ventricle. Then, the muscles of the left atrium relax and the muscles of the left ventricle contract (also referred to as "ventricular systole" or "systole"), to move the oxygenated blood out of the left ventricle 52 and through the aortic valve 63 and the aorta 58 to the rest of the body. The increased blood pressure in the left ventricle during ventricular systole urges the two leaflets of the mitral valve together, thereby closing the one-way mitral valve so that blood cannot flow back into the left atrium. To prevent or inhibit the two leaflets from prolapsing under the pressure and folding back through the mitral annulus toward the left atrium during ventricular systole, a plurality of fibrous cords 62 called chordae tendineae tether the leaflets to papillary muscles in the left ventricle. The chordae tendineae 62 are schematically illustrated in both the heart cross-section of FIG. 1A and the top view of the mitral valve in FIG. 1B.

Problems with the proper functioning of the mitral valve are a type of valvular heart disease. Vascular heart disease can affect the other heart valves as well, including the tricuspid valve. A common form of valvular heart disease is valve leak, also known as regurgitation, which can occur in various heart valve, including both the mitral and tricuspid valves. Mitral regurgitation occurs when the native mitral valve fails to close properly and blood flows back into the left atrium from the left ventricle during ventricular systole. Mitral regurgitation can have different causes, such as leaflet prolapse, dysfunctional papillary muscles, problems with chordae tendineae, and/or stretching of the mitral valve annulus resulting from dilation of the left ventricle. In addition to mitral regurgitation, mitral narrowing or stenosis is another example of valvular heart disease. In tricuspid regurgitation, the tricuspid valve fails to close properly and blood flows back into the right atrium from the right ventricle.

Like the mitral and tricuspid valves, the aortic valve is likewise susceptible to complications, such as aortic valve stenosis or aortic valve insufficiency. One method for treating aortic heart disease includes the use of a prosthetic valve implanted within the native aortic valve. These prosthetic valves can be implanted using a variety of techniques, including various transcatheter techniques. A transcatheter heart valve (THV) can be mounted in a crimped state on the end portion of a flexible and/or steerable catheter, advanced to the implantation site in the heart via a blood vessel connected to the heart, and then expanded to its functional size, for example, by inflating a balloon on which the THV is mounted. Alternatively, a self-expanding THV can be retained in a radially compressed state within a sheath of a delivery catheter, where the THV can be deployed from the sheath, which allows the THV to expand to its functional state. Such delivery catheters and techniques of implantation are generally more developed for implantation or use at the aortic valve, but do not address the unique anatomy and challenges of other valves.

SUMMARY

This summary is meant to provide some examples and is not intended to be limiting of the scope of the invention in any way. For example, any feature included in an example of this summary is not required by the claims, unless the claims explicitly recite the features. Also, the features described can be combined in a variety of ways. Various features and steps as described elsewhere in this disclosure may be included in the examples summarized here.

Tools and methods are provided for delivering a device to a native valve of a patient's heart. In one exemplary embodiment, a catheter can include a flexible tube, a plurality of links, and a control wire. Applying tension to the control wire causes the plurality of links to bend the flexible tube.

In one exemplary embodiment, a delivery catheter for delivering a device to a native valve of a patient's heart includes a flexible tube, a plurality of links, and a control wire. The flexible tube can include a main lumen and a control wire lumen. The plurality of links can be disposed in the distal region of the flexible tube. Each link is aligned with and connected to at least one adjacent link with a slot formed between each pair of adjacent links. A top portion of each link is narrower than a bottom portion of each link when the links are viewed from a side. The control wire is in the control wire conduit and is connected to the plurality of links. Applying tension to the control wire causes the distal region of the flexible tube to bend.

In one exemplary embodiment, a delivery catheter for delivering a device to a native valve of a patient's heart includes a flexible tube, a first ring, a second ring, a plurality of links, a control wire, and a coil sleeve. The flexible tube can have a main lumen and a control wire lumen. A first ring is in a distal region of the flexible tube. A second ring is in the distal region of the flexible tube that is spaced apart from the first ring. A control wire is in the control wire conduit that is connected to the first ring. A plurality of links are disposed in the distal region of the flexible tube between the first ring and the second ring. A coil sleeve is disposed in the control wire lumen around the control wire. The coil sleeve extends proximally from the distal region of the flexible tube such that a portion of the control wire that extends from the second ring to the first ring is not covered by the coil sleeve. Applying tension to the control wire causes the distal region of the flexible tube to bend.

In one exemplary method of making a flexible catheter tube, a flat sheet is provided. A plurality of spaced apart aligned cutouts are cut in to the sheet. Each cutout has a central portion between two end portions. A width of the central portion of each cutout is wider than the width of the two end portions of each cutout. The cutouts form a corresponding plurality of spaced apart aligned strips each having a central portion and two end portions. A width of the central portion of strip is narrower than the width of the two end portions of strip. The sheet is rolled into a substantially cylindrical shape having a plurality of links with a slot formed between each pair of adjacent links. Top portions of the links correspond to the central portions of the strips and bottom portions of the links correspond to the end portions of the strips.

The tools and methods summarized here can also include any of the features, components, elements, etc. described elsewhere in this disclosure, and the methods summarized here can also include any of the steps described elsewhere in this disclosure.

BRIEF DESCRIPTION OF THE DRAWINGS

The foregoing and other objects, features, and advantages of the invention will become more apparent from the following detailed description using the accompanying figures. In the drawings:

FIG. 9G illustrates the delivery device of FIG. 9A in a fourth position;

FIG. 9H illustrates the delivery device of FIG. 9A in the fourth position shown in FIG. 9G, in which the delivery device is shown from a view taken along the lines H-H in FIG. 9G;

FIG. 9I is a side cutout view of the left side of a patient's heart that illustrates a an anchoring device being delivered around the chordae tendineae and leaflets in the left ventricle of the patient's heart;

FIG. 9K illustrates the anchoring device of FIG. 9I further wrapping around the chordae tendineae and leaflets in the left ventricle of the patient's heart as it is being delivered by the delivery device of FIG. 9A;

FIG. 9M illustrates the delivery device of FIG. 9A in the left atrium of the patient's heart, in which the delivery device is retracting to deliver a portion of the anchoring device in the left atrium of the patient's heart;

FIG. 9O illustrates the delivery device of FIG. 9A in the left atrium of the patient's heart, in which the anchoring device is exposed and shown connected tightly to a pusher in the left atrium of the patient's heart;

FIGS. 17A-17C show perspective views of an exemplary lock or locking mechanism for an anchoring device;

FIG. 17D is a cross-sectional view of the lock or locking mechanism of FIGS. 17A-17C;

FIGS. 18A-18C show perspective views of another exemplary lock or locking mechanism for an anchoring device according to one embodiment.

FIG. 20A is an end view of another exemplary embodiment of a delivery catheter;

FIG. 20B is a sectional view taken along the plane indicated by lines B-B in FIG. 20A;

FIG. 20C is a sectional view taken along the plane indicated by lines C-C in FIG. 20C;

FIG. 20D is a sectional view taken along the plane indicated by lines D-D in FIG. 20C;

FIG. 20E is a sectional view taken along the plane indicated by lines E-E in FIG. 20C;

FIG. 22A is a partial view of the delivery catheter of FIGS. 20A-20E;

FIGS. 22B-22D show cross-sectional views of the delivery catheter shown in FIG. 22A, the cross-sections taken in a plane perpendicular to a longitudinal axis of the delivery catheter.

DETAILED DESCRIPTION

The following description and accompanying figures, which describe and show certain embodiments, are made to demonstrate, in a non-limiting manner, several possible configurations of systems, devices, apparatuses, components, methods, etc. that may be used for various aspects and features of the present disclosure. As one example, various systems, devices/apparatuses, components, methods, etc. are described herein that may relate to mitral valve procedures. However, specific examples provided are not intended to be limiting, e.g., the systems, devices/apparatuses, components, methods, etc. can be adapted for use in other valves beyond the mitral valve (e.g., in the tricuspid valve).

Described herein are embodiments of deployment tools that are intended to facilitate implantation of prosthetic devices (e.g., prosthetic valves) at one of the native mitral, aortic, tricuspid, or pulmonary valve regions of a human heart, as well as methods for using the same. The prosthetic devices or valves can be expandable transcatheter heart valves ("THVs") (e.g., balloon expandable, self-expandable, and/or mechanically expandable THVs). The deployment tools can be used to deploy anchoring devices (sometimes referred to as docking devices, docking stations, or similar terms) that provide a more stable docking site to secure the prosthetic device or valve (e.g., THVs) at the native valve region. These deployment tools can be used to more accurately place such anchoring devices (e.g., prostheses anchoring devices, prosthetic valve anchoring device, etc.), so that the anchoring devices and any prostheses (e.g., prosthetic devices or prosthetic heart valves) anchored thereto function properly after implantation.

Figure 1A:
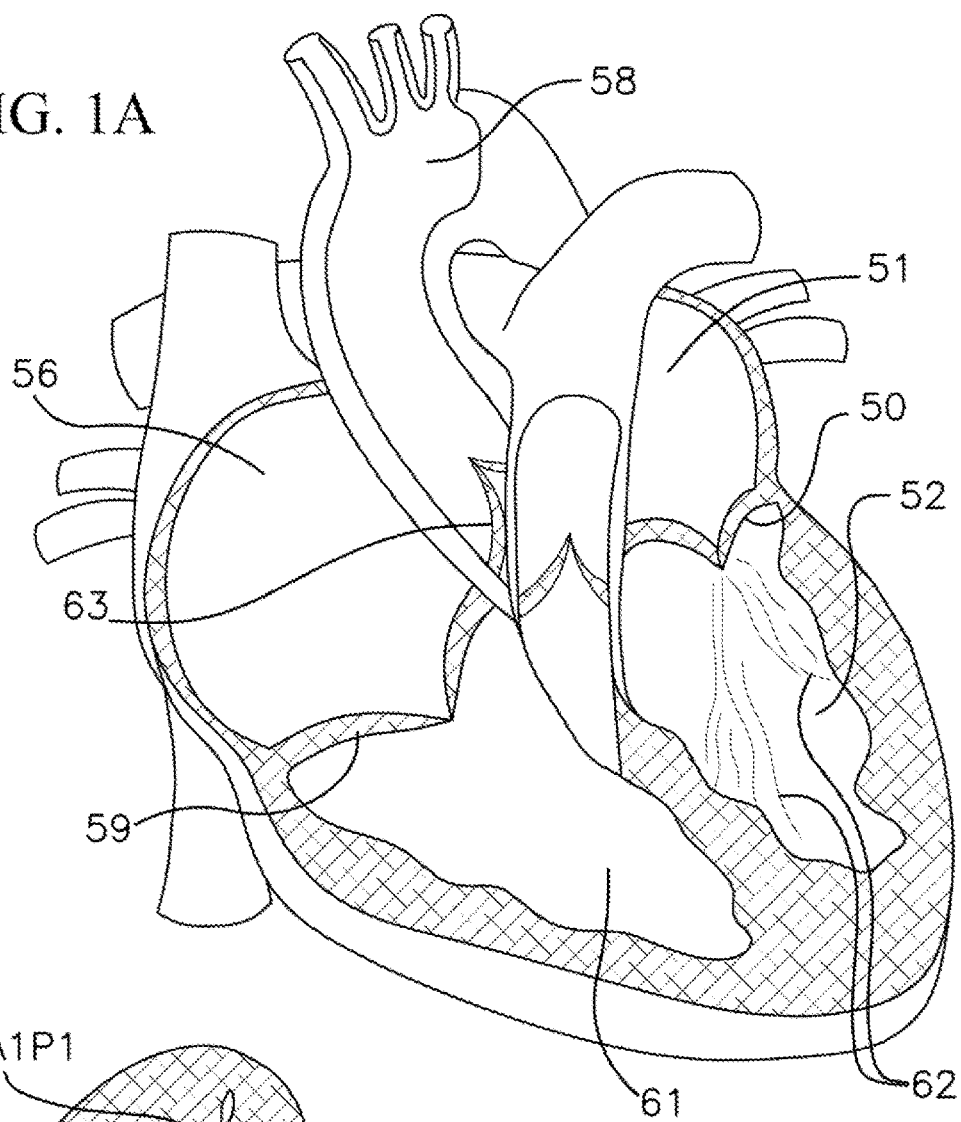
FIG. 1A shows a schematic cross-sectional view of a human heart.
Figure 1B:
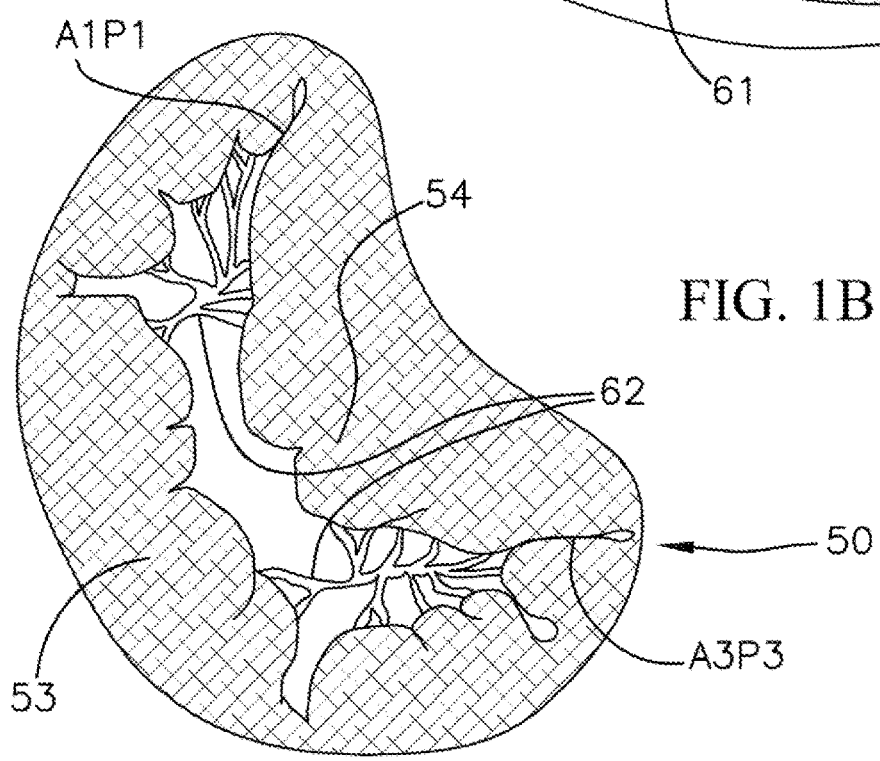
FIG. 1B shows a schematic top view of the mitral valve annulus of a heart.
Figure 2A:
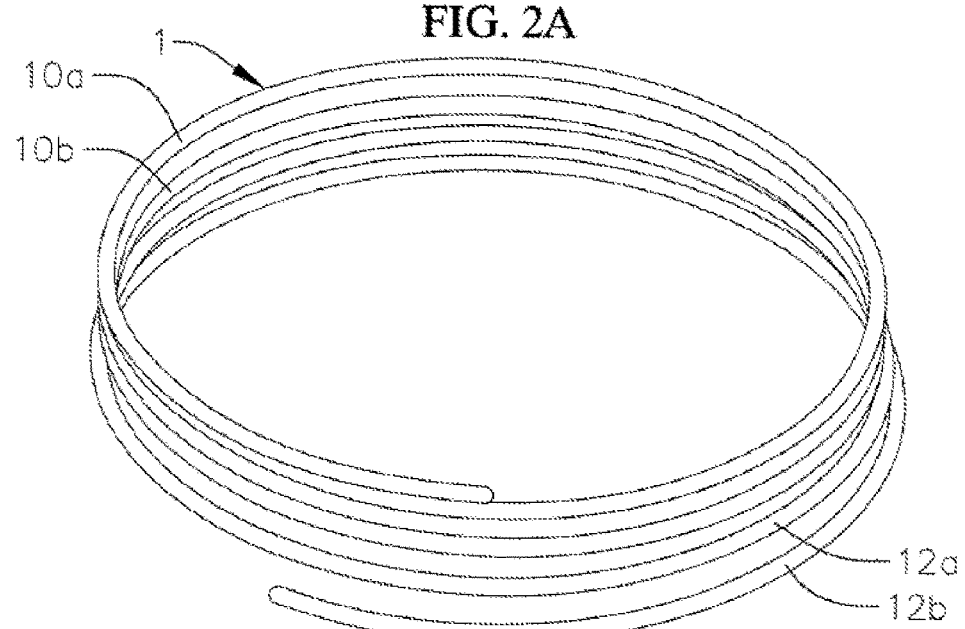
FIG. 2A shows a perspective view of an exemplary anchoring device that is helical.

An example of one such anchoring device is shown in FIG. 2A. Other examples of anchoring devices that can be used herein are shown in U.S. patent application Ser. Nos. 15/643,229, 15/684,836, and 15/682,287, which are each incorporated by reference in their entirety herein. The anchoring devices herein can be coiled or helical or they can include one or more coiled or helical regions. Anchoring device 1 is shown in FIG. 2A as including two upper coils 10a, 10b and two lower coils 12a, 12b. In alternative embodiments, the anchoring device 1 can include any suitable number of upper coils and lower coils. For example, the anchoring device 1 can include one upper coil, two or more upper coils, three or more upper coils, four or more upper coils, five or more upper coils, etc. In addition, the anchoring device 1 can have one lower coil, two or more lower coils, three or more lower coils, four or more lower coils, five or more lower coils, etc. In various embodiments, the anchoring device 1 can have the same number of upper coils as it has lower coils. In other embodiments, the anchoring device 1 can have more or less upper coils as compared to lower coils.

Anchoring devices can include coils/turns of varying diameters or the same diameters, coils/turns spaced with varying gap sizes or no gaps, and coils/turns which taper, expand, or flare to become larger or smaller. It should be noted that the coils/turns can also stretch radially outward when a prosthetic valve is placed or expanded within anchoring device 1.

In the illustrated embodiment of FIG. 2A, the upper coils 10a, 10b can be about the same size as or can have a slightly smaller diameter than the lower coils 12a, 12b. One or more lower end coils/turns (e.g., a full or partial end coil/turn) can have a larger diameter or larger radius of curvature than other coils and act as an encircling coil/turn to help guide the end of the coil outside and around the leaflets and/or any chordae tendineae, e.g., to encircle and corral the leaflets and/or any chordae tendineae. One or more larger-diameter or larger-radius lower coils or encircling coils allow for easier engagement with the native valve annulus and navigation around the native valve anatomy during insertion.

In some embodiments, one or more upper coils/turns (e.g., full or partial coils/turns) can be larger or have a larger diameter (or radius of curvature) and act as a stabilization coil (e.g., in an atrium of the heart) to help hold the coil in position before the prosthetic valve is deployed therein. In some embodiments, the one or more upper coils/turns can be atrial coils/turns and can have a greater diameter than the coils in the ventricle, for example, acting as a stabilization coil/turn configured to engage an atrial wall for stability.

Some of the coils can be functional coils (e.g., coils/turns between the stabilization coil(s)/turn(s) and the encircling coil(s)/turn(s)) in which the prosthetic valve is deployed and forces between the functional coils and prosthetic valve help to hold each other in position. The anchoring device and prosthetic valve may pinch native tissue (e.g., leaflets and/or chordae) between themselves (e.g., between the functional coils of the anchoring device and an outer surface of the prosthetic valve) to more securely hold them in place.

In one embodiment, which can be the same as or similar to the anchoring device shown in FIGS. 9I-9U, an anchoring device has one large upper coil/turn or stabilization coil/turn, one lower end coil/turn or encircling coil/turn, and multiple functional coils/turn (e.g., 2, 3, 4, 5, or more functional coils/turns).

Figure 2B:
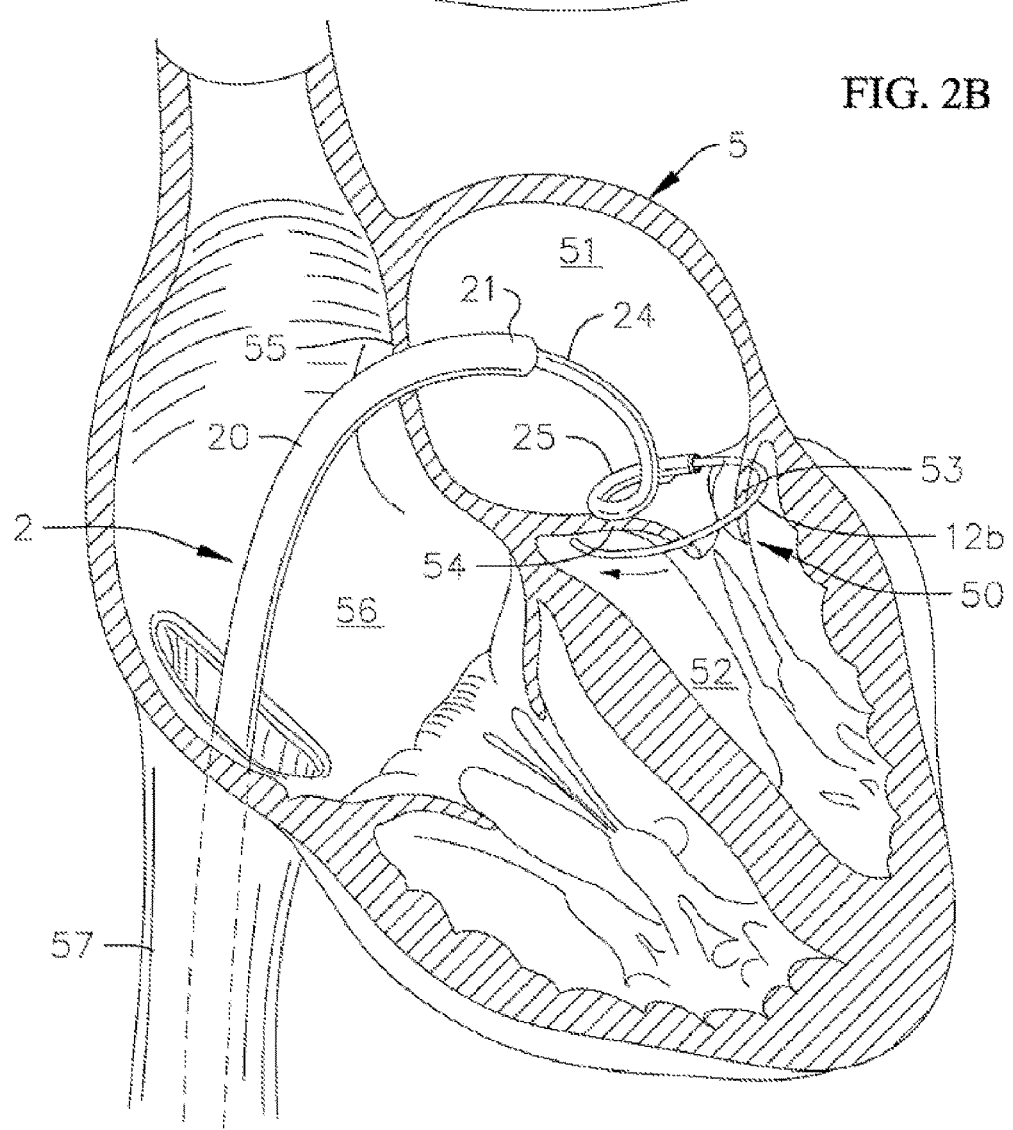
FIG. 2B shows a partial perspective view of a an exemplary delivery device for implanting the anchoring device at a native valve of a heart, using a transseptal technique.
Figure 2C:
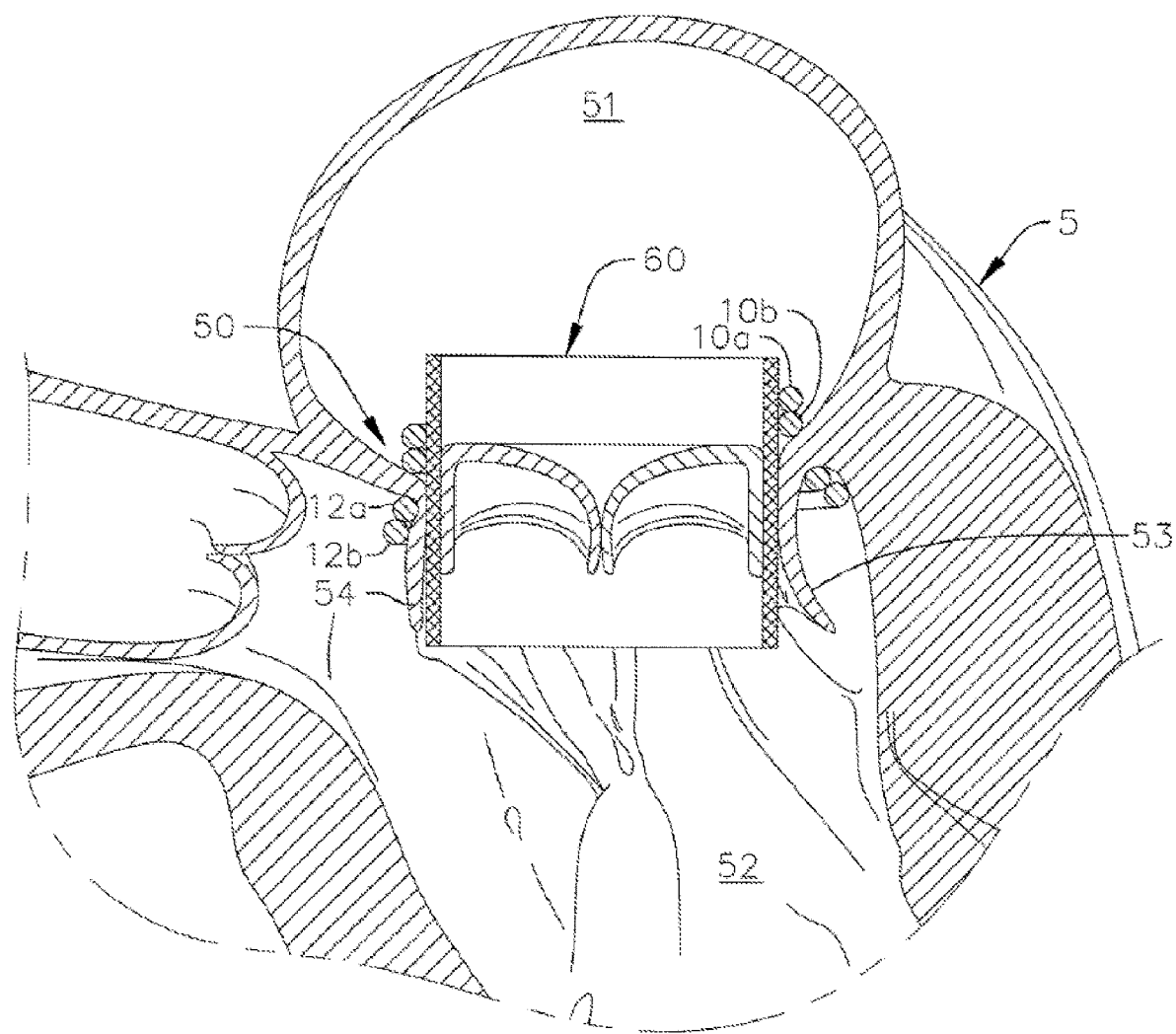
FIG. 2C shows a cross-sectional view of the anchoring device and an exemplary prosthetic heart valve implanted at the native valve of the heart.

When used at the mitral position, the anchoring device can be implanted so that one or more upper coils/turns (e.g., the upper coils 10a, 10b) are above, i.e., on the atrial side, of the annulus of the native valve (e.g., mitral valve 50 or a tricuspid valve) and the lower coils 12a, 12b are below, i.e., on the ventricular side, of the annulus of the native valve, for example, as shown in FIG. 2C. In this configuration, the mitral leaflets 53, 54 can be captured between the upper coils 10a, 10b and the lower coils 12a, 12b. When implanted, the various anchoring devices herein can provide a solid support structure to secure a prosthetic valve in place and avoid migration due to the operation of the heart.

FIG. 2B shows a general delivery device 2 for installing an anchoring device at a native mitral valve annulus 50 using a transseptal technique. The same or a similar delivery device 2 could be used to delivery an anchoring device at the tricuspid valve without having to leave the right atrium to cross the septum into the left atrium. The delivery device 2 includes an outer sheath or guide sheath 20 and a flexible delivery catheter 24. The sheath 20 has a shaft in the shape of an elongated hollow tube through which the delivery catheter 24, as well as various other components (e.g., the anchoring device, a prosthetic heart valve, etc.), can pass, thus allowing the components to be introduced into the patient's heart 5. The sheath 20 can be steerable so that the sheath 20 can be bent at various angles needed for the sheath to pass through the heart 5 and enter the left atrium 51. While in the sheath 20, the delivery catheter 24 is in a relatively straight or straightened configuration (compared to a bent configuration discussed in greater detail below), e.g., the delivery catheter 24 is held in sheath 20 in a configuration or shape that corresponds to the configuration or shape of the sheath 20.

Like the sheath 20, the delivery catheter 24 has a shaft having the shape of an elongated hollow tube. However, the delivery catheter 24 has a smaller diameter than the sheath 20 so that it can slide axially within the sheath 20. Meanwhile, the delivery catheter 24 is large enough to house and deploy an anchoring device, such as the anchoring device 1.

The flexible delivery catheter 24 also has a flexible distal section 25. The distal section 25 can bend into a configuration that allows for more accurate placement of the anchoring device 1, and in general should have a robust design that allows for the distal section 25 to be bent and held at such configuration. For example, as shown in FIG. 2B, the flexible distal section 25 can bend into a curved configuration in which the distal section 25 is curved to assist in extrusion or pushing out of the anchoring device 1 on a ventricular side of the mitral valve 50, so that the lower coils (e.g., functional coils and/or encircling coils) of the anchoring device 1 can be properly installed below the annulus of the native valve. The flexible distal section 25 can also be bent into the same or in a different curved configuration so that the upper coil(s) (e.g., a stabilization coil/turn or upper coils 10a, 10b) of the anchoring device can be accurately deployed on the atrial side of the annulus of the native valve. For example, the flexible distal section 25 can have the same configuration for installing the upper coils 10a, 10b as is used for installing the lower coils 12a, 12b. In other embodiments, the flexible distal section 25 can have one configuration for installing the lower coils 12a, 12b and another configuration for installing the upper coils 10a, 10b. For example, the flexible distal section 25 can be axially translated backwards from the position described above for releasing the lower coils 12a, 12b to release and position the upper coils 10a, 10b on the atrial side of the annulus of the native valve.

In use, when using a transseptal delivery method to access the mitral valve, the sheath 20 can be inserted through a femoral vein, through the inferior vena cava 57 and into the right atrium 56. Alternatively, the sheath 20 can be inserted through a jugular vein or subclavian vein or other upper vasculature location and passed through the superior vena cava and into the right atrium. The interatrial septum 55 is then punctured (e.g., at the fossa ovalis) and the sheath 20 is passed into the left atrium 51, as can be seen in FIG. 2B. (In tricuspid valve procedures, it is unnecessary to puncture or cross the septum 55.) The sheath 20 has a distal end portion 21, which can be a steerable or pre-curved distal end portion to facilitate steering of the sheath 20 into the desired chamber of the heart (e.g., the left atrium 51).

In mitral valve procedures, with the sheath 20 in position in the left atrium 51, the delivery catheter 24 is advanced from the distal end 21 of the sheath 20, such that the distal section 25 of the delivery catheter 24 is also in the left atrium 51. In this position, the distal section 25 of the delivery catheter 24 can be bent or curved into one or more curved or activated configuration(s) to allow for an anchoring device 1 to be installed at the annulus of the mitral valve 50. The anchoring device 1 can then be advanced through the delivery catheter 24 and installed at the mitral valve 50. The anchoring device 1 can be attached to a pusher that advances or pushes the anchoring device 1 through the delivery catheter 24 for implantation. The pusher can be a wire or tube with sufficient strength and physical characteristics to push the anchoring device 1 through the delivery catheter 24. In some embodiments, the pusher can be made of or include a spring or coil (e.g., see flexible tubes 87, 97 in FIGS. 17A-18C below), a tube extrusion, a braided tube, or a laser cut hypotube, among other structures. In some embodiments, the pusher can have a coating over and/or inside it, e.g., it can have an interior lumen lined by PTFE to allow a line (e.g., a suture) to be atraumatically actuated through the lined lumen. As noted above, in some embodiments, after the pusher has pushed and properly positioned the ventricular coils of the anchoring device 1 in the left ventricle, the distal section 25 can, for example, be axially translated backwards to release the atrial coils of the anchoring device 1 into the left atrium, while maintaining or holding a position of the ventricular coils of the anchoring device 1 within the left ventricle.

Once the anchoring device 1 is installed, the delivery catheter 24 can be removed by straightening or reducing the curvature of the flexible distal section 25 to allow the delivery catheter 24 to pass back through the sheath 20. With the delivery catheter 24 removed, a prosthetic valve, for example, a prosthetic transcatheter heart valve (THV) 60 can then be passed, for example, through the sheath 20 and secured within the anchoring device 1, as shown for example in FIG. 2C. When the THV 60 is secured within the anchoring device 1, the sheath 20 along with any other delivery apparatuses for the THV 60 can then be removed from the patient's body and the openings in the patient's septum 55 and right femoral vein can be closed. In other embodiments, after the anchoring device 1 has been implanted, a different sheath or different delivery device altogether can be separately used to deliver the THV 60. For example, a guide wire can be introduced through sheath 20, or the sheath 20 can be removed and the guide wire can be advanced via the same access point, through the native mitral valve, and into the left ventricle, using a separate delivery catheter. Meanwhile, even though the anchoring device is implanted trans-septally in this embodiment, it is not limited to transseptal implantation, and delivery of the THV 60 is not limited to transseptal delivery (or more generally via the same access point as delivery of the anchoring device). In still other embodiments, after transseptal delivery of the anchoring device 1, any of various other access points can thereafter be used to implant the THV 60, for example, trans-apically, trans-atrially, or via the femoral artery.

Figure 3A:
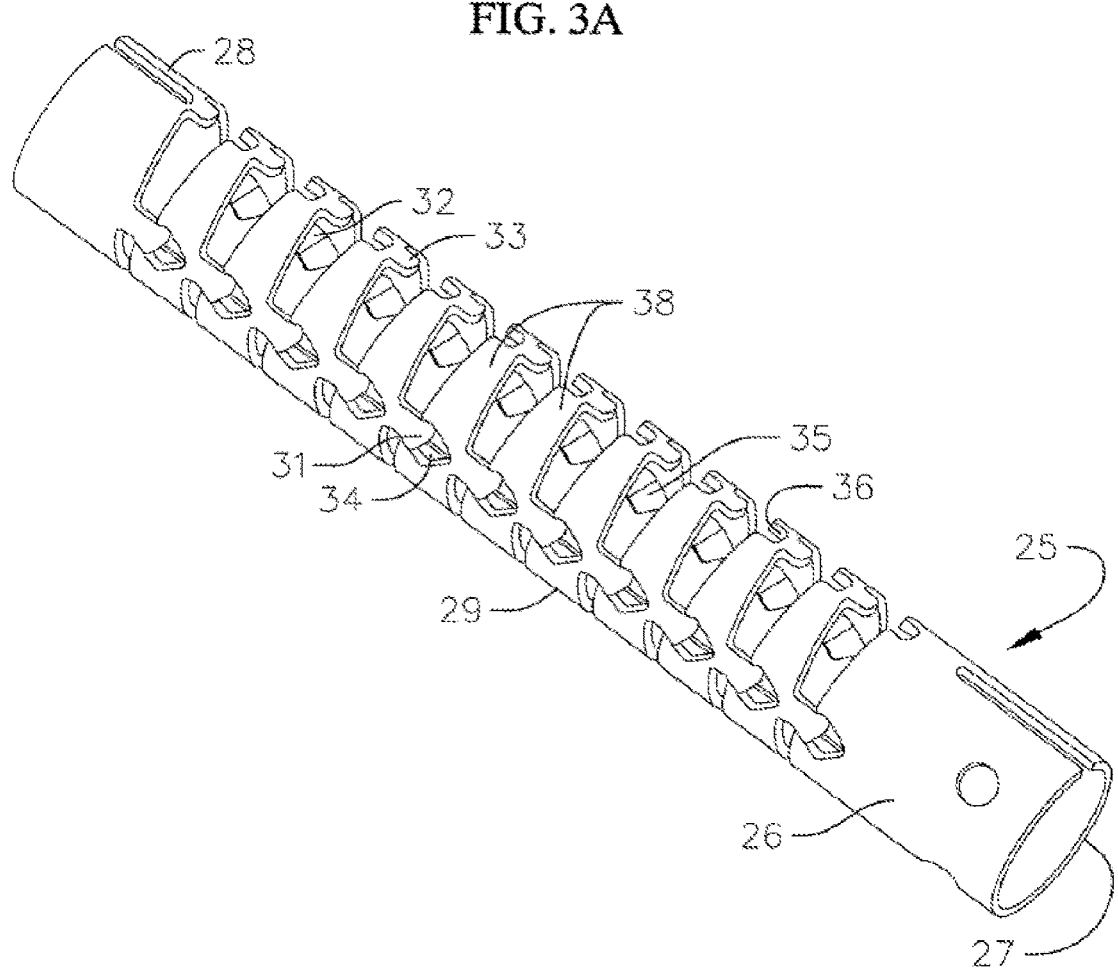
FIG. 3A shows a perspective view of an exemplary distal section of a delivery catheter used as part of an exemplary delivery device for implanting an anchoring device.
Figure 3B:
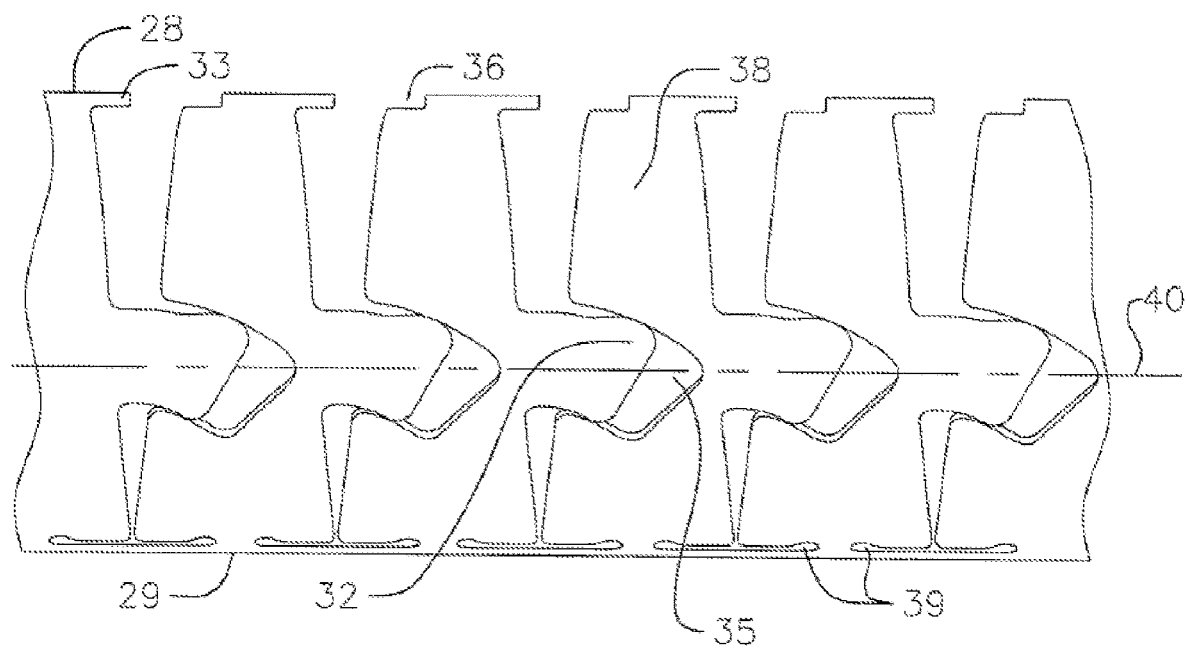
FIG. 3B is a cross-sectional view of several links of the distal section of FIG. 3A.

FIG. 3A shows a perspective view of an exemplary distal section 25 that can be used in a delivery catheter 24. The distal section includes two opposite ends, two opposite sides 26 & 27, a top 28, and a bottom 29 extending between the two ends. These have been labelled for ease of description and understanding and are not intended to limit the orientation of the distal section 25. The distal section 25 of FIG. 3A forms a generally cylindrical hollow tube that can include a plurality of links 38. Each link 38 has the shape of a cylindrical segment and each link 38 is aligned with and connected to adjacent links 38 to form the cylindrical tube shape of the distal section 25. While the distal section 25 is cylindrical in this embodiment, other shapes, such as ovular distal sections, are also possible. Each link 38 of the distal section 25 can have a greater width at the bottom 29 than at the top 28, giving the links 38 the general shape of an acute trapezoid when viewed from the side, as best seen in FIG. 3B. The bottom of each link 38 can have slits 39 to allow for more flexing of the links 38 relative to one another.

Figure 4:
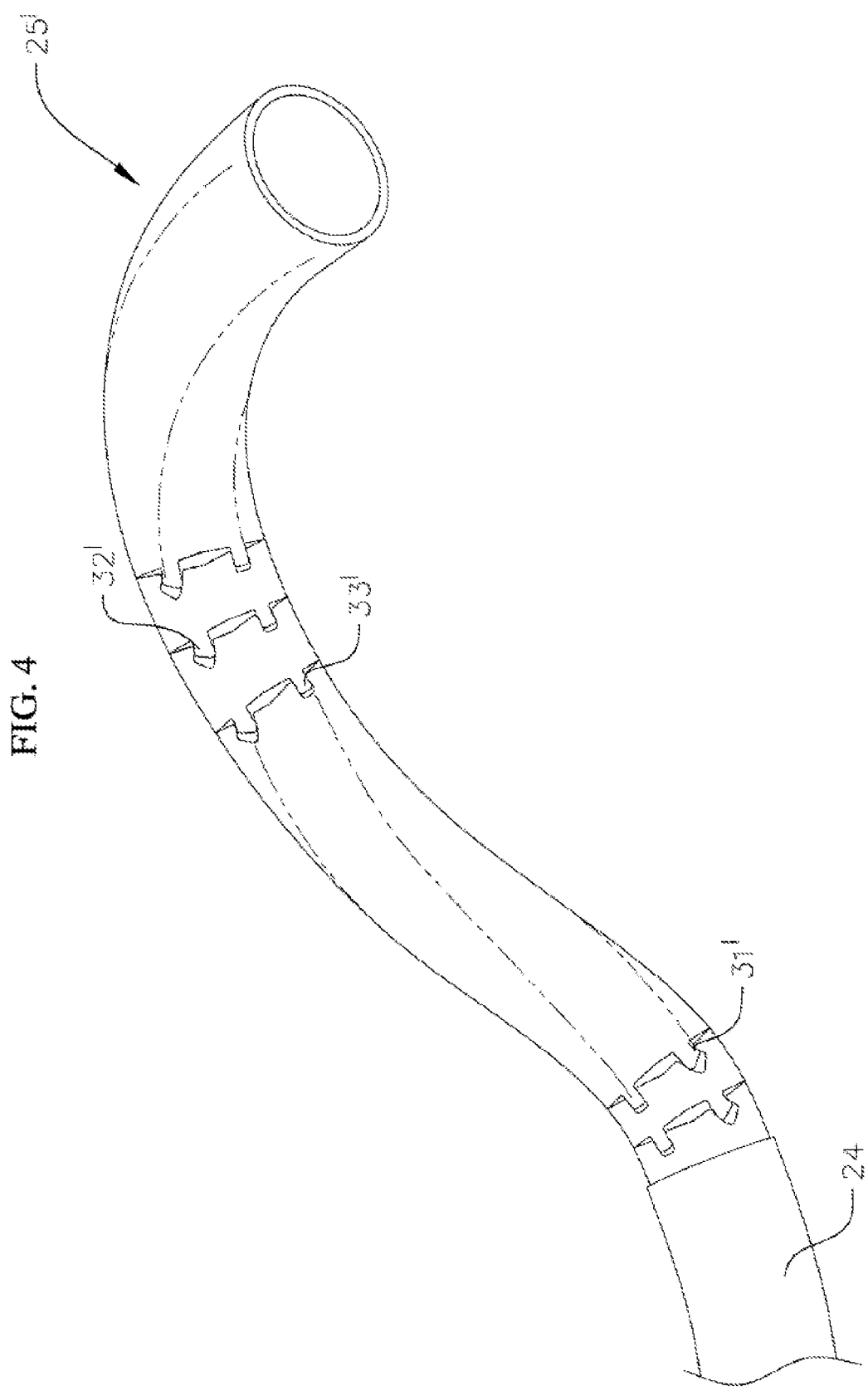
FIG. 4 is a perspective view of the distal section of the delivery catheter in a bent or curved configuration.

The distal section 25 can include a double guiding pattern forming a hybrid bending section that incorporates both side teeth 31, 32 and top teeth 33. To this effect, each link 38 can include two side teeth 31, 32 on opposite sides of the link 38 and a top tooth 33. With respect to the distal section 25, the two rows of side teeth 31, 32 of the links 38 can run the length of the sides 26, 27 of the distal section 25, respectively, and the top teeth 33 can run the length of the distal section 25 on the top 28, as best seen in FIG. 3A. While the rows of side teeth 31, 32 and top teeth 33 are shown to run straight along the length of the distal section 25 in this illustrated embodiment, other embodiments can have different configurations. For example, in some embodiments, the rows of side teeth 31, 32 and top teeth 33 can spiral around the tube of the distal section 25, for example, as shown in FIG. 4, to effect specific bending shapes of the distal section 25 when the distal section 25 is actuated. In certain embodiments, the side teeth 31, 32 can be mirror images of each other to allow analogous bending on opposite sides 26, 27 of the distal section 25. In other embodiments, the side teeth 31, 32 can have different shapes and/or sizes in comparison to each other. The teeth 31, 32, 33 can take any other suitable shape and/or size that allows the distal section 25 to move to a flexed configuration while delivering an anchoring device. While the teeth 31, 32, 33 are all right-facing teeth in the illustrated embodiment (e.g., directed to the right in the view shown in FIG. 3B), in other embodiments, the teeth can be left-facing teeth (see, for example, FIG. 4) or the top and side teeth can face different directions, for example.

Adjacent to each side tooth 31, 32 and each top tooth 33 is a corresponding side slot or groove 34, 35 and top slot or groove 36, respectively, on an adjacent link 38. Each slot 34, 35, 36 can have a shape complementary to the side tooth 31, 32 or top tooth 33 to which it is adjacent. When the distal section 25 is in a straightened configuration, the side teeth 31, 32 are partially inserted into the side slots 34, 35 and the top teeth 33 are partially separated from their adjacent top slots 36 by a gap. Having the side teeth 31, 32 partially within the side slots 34, 35 in this straightened configuration provides additional torque resistance to the distal section 25 when the distal section 25 of the delivery catheter 24 is not fully flexed. However, in other embodiments, the side teeth 31, 32 may not be positioned partially within the side slots 34, 35 when the distal section 25 is in the straightened configuration.

When the distal section 25 is bent, each side tooth 31, 32 moves further into its corresponding side slot 34, 35 and each top tooth 33 moves closer to and then into its corresponding top slot 36. The addition of the top teeth 33 and top slots 36 provides enhanced torqueability and torque resistance to the distal section 25 when it is in the fully flexed configuration. Further, having both side teeth 31, 32 and top teeth 33 provides additional guiding control and structural support when adjusting the distal section 25 from its straightened to its flexed configuration.

FIG. 3B is a detailed cross-sectional view of several links 38 of the distal section 25 of FIG. 3A. While FIG. 3B is described with respect to the side teeth 32, this description equally applies to side teeth 31 on the opposite side of the distal section 25. Side teeth 32 are shown as being positioned along a tooth line 40 that is low relative to the top 28 of the distal section 25. This positioning causes the side teeth 32 to have a smaller displacement, i.e., the distance the side teeth 32 move into the adjacent slot 35 is much shorter or less than if the side teeth 32 were positioned closer to the top 28 of the distal section 25. For example, in the illustrated embodiment, the distance that the side teeth 31, 32 move during flexing is smaller compared to the distance that the top teeth 33 move. In other words, the top teeth 33 move a greater distance relative to adjacent links 38 when the distal section 25 is adjusted to a fully bent configuration, as compared to the side teeth 31, 32. This arrangement allows the use of shorter side teeth 31, 32 (e.g., to have side teeth with shorter longitudinal lengths), which can in turn be incorporated into shorter bending sections in the distal section 25.

Further, the low tooth line also provides more space for wider tooth slots 34, 35 to accommodate, for example, even larger side teeth since the tooth slots 34, 35 are located at the wider lower portions of the links 38. Having more space to house larger and/or more appropriate or robust tooth slots 34, 35 for the side teeth 31, 32 can enhance guiding of the teeth 31, 32 into the slots 34, 35, for example, during bending. The low tooth line also allows for the above discussed robust tooth design that can still provide structural support while bending the links away from each other, i.e., in the opposite direction of the bending configuration. Therefore, when bending the links away from each other, the side teeth can still maintain their interface with the adjacent side slots, and this maintained tooth-slot interface can provide for more structural support and torqueability.

FIG. 4 is a perspective view of a distal section 25' in a bent configuration according to a modification of the first embodiment. The distal section 25' in FIG. 4 is similar to the distal section 25 of FIG. 3A, except that in FIG. 4, the rows of top teeth 33' and the rows of side teeth 31', 32' are shifted laterally around the tube-shaped distal section 25' instead of continuing in a straight line down the length of the distal section. This positioning of the rows of teeth 31', 32', 33' along, for example, a spiral line allows the distal section 25' to bend in three dimensions, as opposed to a single plane as would occur in FIG. 3A. As seen in FIG. 4, the example distal section 25' has a three dimensional curved shape. Various embodiments of distal sections can be laser cut (e.g., into a sheet or tube) so that the top and side teeth follow a pattern that will form a desired shape during bending. For example, patterns can be cut that create a distal section having a bent shape that, when used in surgery, allows the distal section to be positioned at the mitral or other valve, such that an anchoring device can be advanced from the distal section and accurately positioned at the valve.

Figure 5:
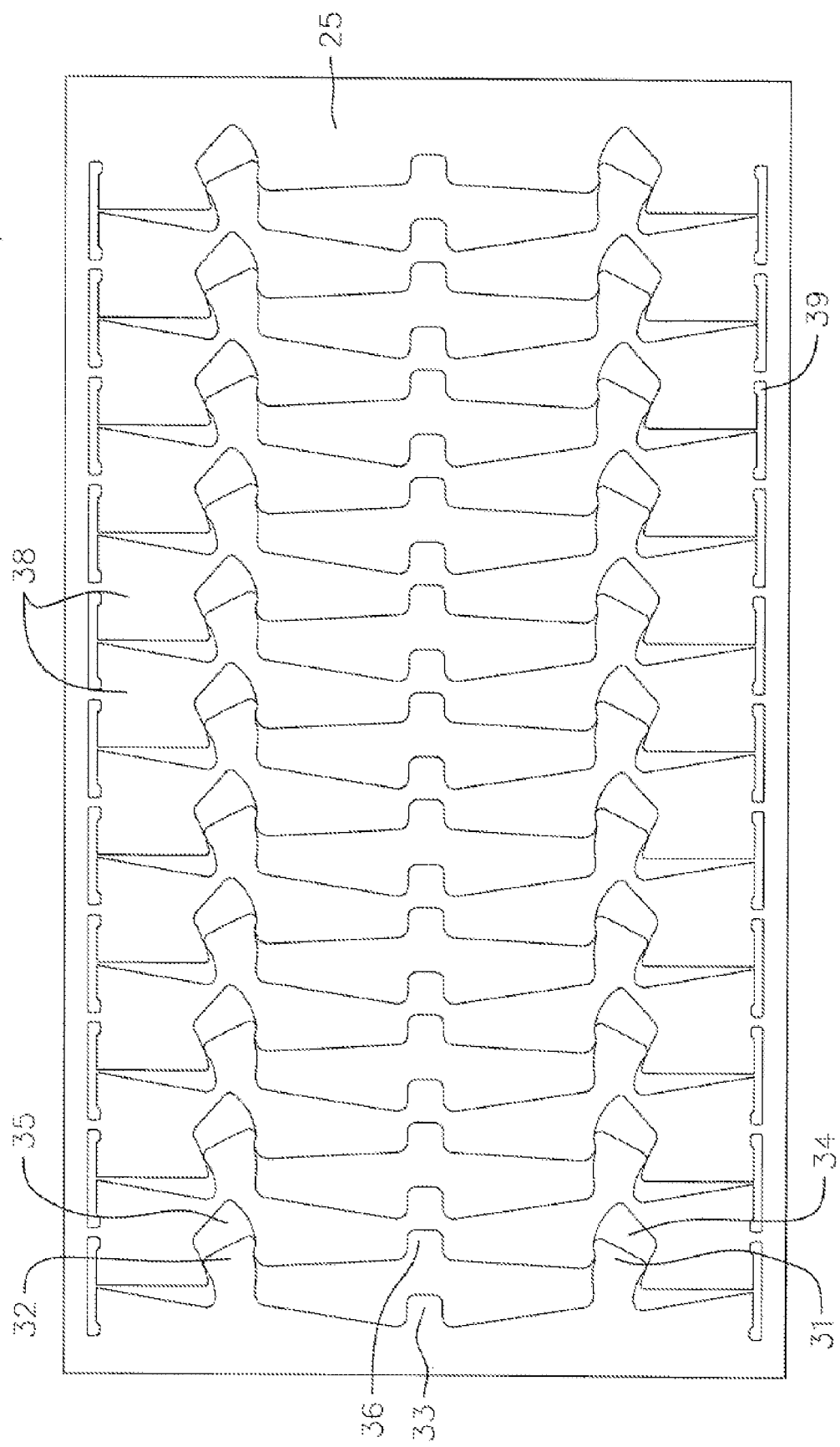
FIG. 5 is a flat view of an exemplary laser cut sheet that can be used for forming a distal section of a delivery catheter.

Distal sections 25, 25' can be manufactured by cutting, for example, by laser cutting a flat metal strip or sheet with the desired pattern and then rolling the patterned metal strip or sheet into a hypotube. Alternatively, the desired pattern (e.g., the same or similar patterns to those shown in various figures herein) could be cut directly into a tube (e.g., a hypotube) without using a sheet or having to roll the material. As an example, FIG. 5 shows a flat view of an exemplary laser cut file or sheet 30 that can be used for the distal section 25 of FIG. 3A. This laser cut sheet 30 includes both the top teeth 33 and their associated slots 36 and the side teeth 31, 32 and their associated slots 34, 35 arranged in straight rows along the length of the distal section 25. However, as noted above, this laser cut file 30 can be modified to have the teeth 31, 32, 33 and their associated slots 34, 35, 36 arranged in other different paths or configurations, for example, in rows of spiral lines, in order to create a curved or spiral bent distal section 25' similar to the one shown in FIG. 4. In other embodiments, various patterns can be cut that provide distal sections that can bend in other shapes or configurations that help accurately navigate and deploy an anchoring device into position at the implant site during surgery.

Many types of sheets capable of being folded into tubing can be used for making the cut distal sections. Further many types of tubes can be cut into the desired pattern(s). For example, Nitinol and stainless steel can be used, as well as various other suitable metals known in the art, as materials for the sheets or tubes.

While the above embodiments include both top and side teeth, such that each link 38 has three teeth total, other embodiments may only include one of either the top or side teeth, or no teeth at all.

Figure 6:
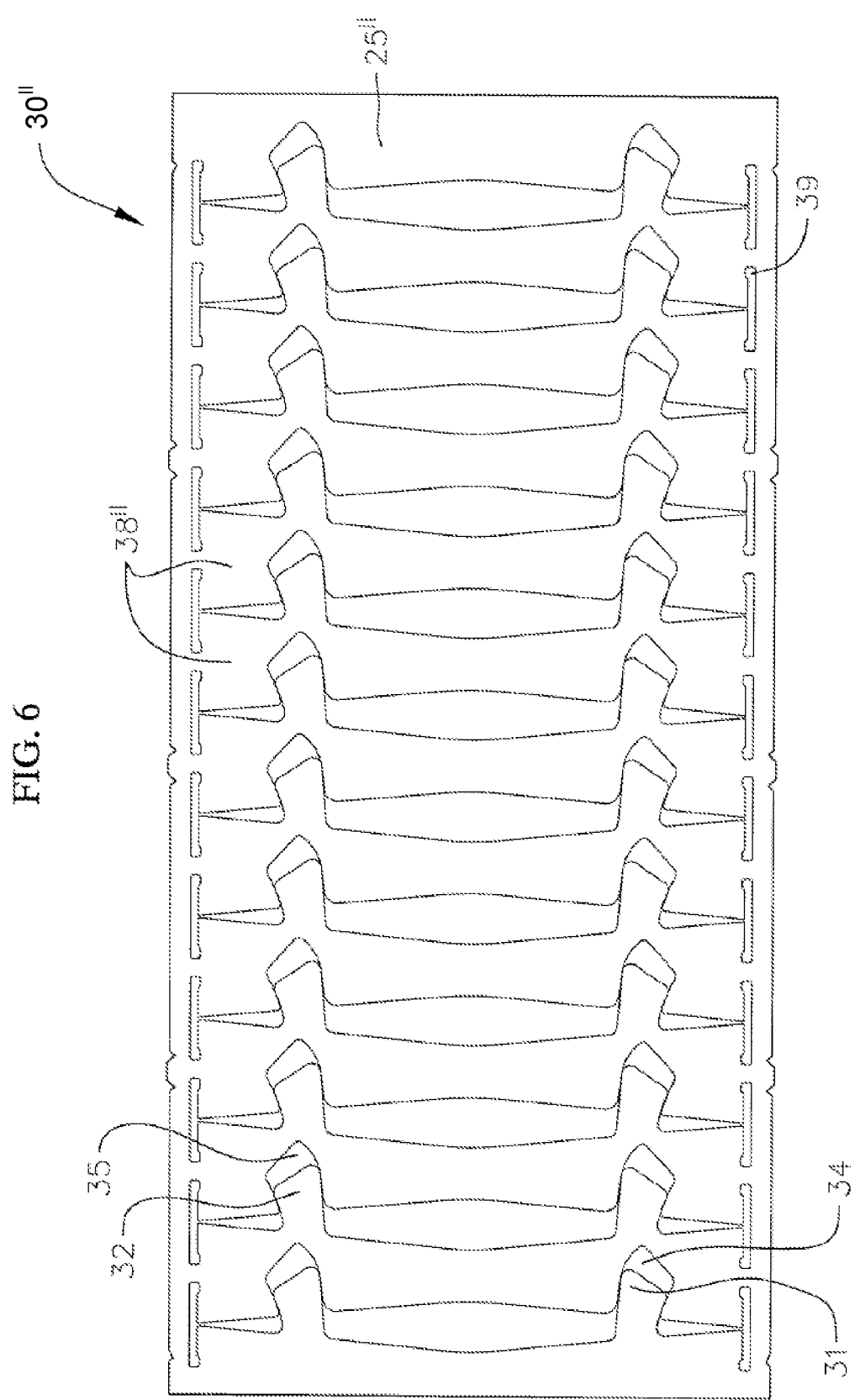
FIG. 6 is a flat view of another exemplary laser cut sheet that can be used for forming a distal section of a delivery catheter.

FIG. 6 is a flat view of another exemplary laser cut sheet 30" for a distal section 25" of a delivery catheter. The distal section 25" of FIG. 6 is similar to the distal section 25 of FIG. 5, however, links 38" of the distal section 25" only include the two side teeth 31, 32 and their associated slots 34, 35, and do not include any top teeth or corresponding slots.

Figure 7:
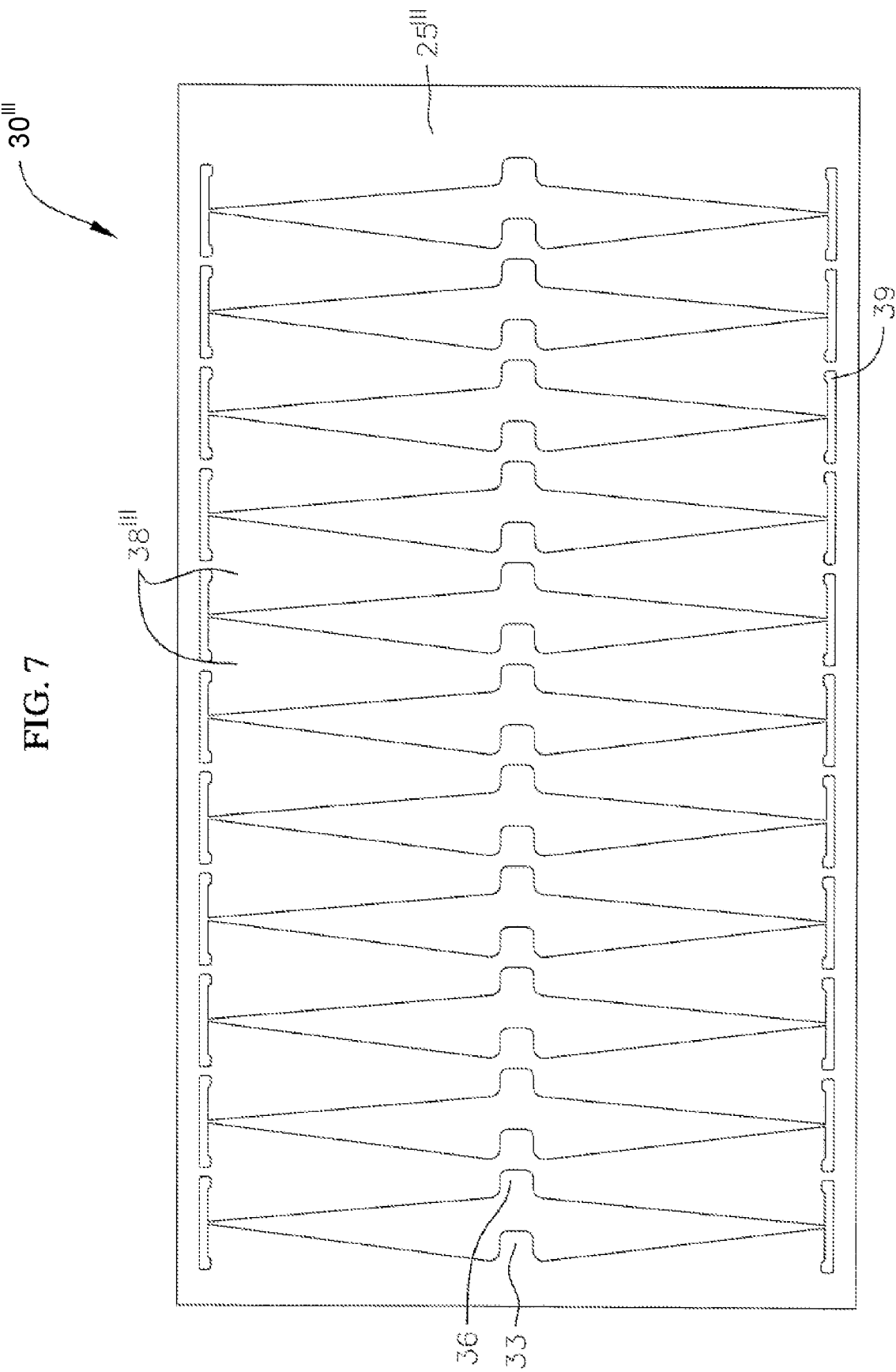
FIG. 7 is a flat view of another exemplary laser cut sheet that can be used for forming a distal section of a delivery catheter.

FIG. 7 is a flat view of another exemplary laser cut sheet 30'" for a distal section 25'" of a delivery catheter. The distal section 25'" of FIG. 7 is also similar to the distal section 25 of FIG. 5, however, each of the links 38'" of the distal section 25'" only includes the single top tooth 33 and its associated slot 36 and do not include any side teeth or corresponding slots.

In other embodiments, more or less than three teeth in any combination can be included on each link. Meanwhile, while FIGS. 6 and 7 are shown with teeth arranged in straight rows along the length of the distal sections 25", 25'", respectively, the laser cut sheets 30", 30'" can also be modified to include various tooth patterns and arrangements in order to have distal sections capable of bending in specific desired shapes, similarly as discussed above.

Various sheath and catheter designs can be used to effectively deploy the anchoring device at the implant site. For example, for deployment at the mitral position, the delivery catheter can be shaped and/or positioned to point towards commissure A3P3, so that a coil anchor deployed from the catheter can more easily enter the left ventricle and encircle the chordae 62 during advancement. However, while the various exemplary embodiments of the invention described below are configured to position the distal opening of the delivery catheter at commissure A3P3 of the mitral valve, in other embodiments, the delivery catheter can approach the mitral plane to point to, and the anchoring device can be advanced through, commissure A1P1 instead. In addition, the catheter can bend either clockwise or counter-clockwise to approach either commissure of the mitral valve or a desired commissure of another native valve, and the anchoring device can be implanted or inserted in a clockwise or counter-clockwise direction (e.g., coils/turns of the anchoring device can turn in a clockwise or counter-clockwise direction depending on how the anchoring device will be implanted).

In still further embodiments, the catheter itself can also be positioned to pass below a plane of the annulus of a native valve and sit in one of the commissures or to extend into a ventricle (e.g., through one of the commissures). In some embodiments, the distal end of the catheter can even be used to capture and/or corral some or all the chordae tendineae 62. The catheter can be positioned in any suitable manner that allows an anchoring device to be deployed at an implant site. In some embodiments, the catheter itself can have an atraumatic tip design, to provide atraumatic access to the implant site, for example, by reducing or eliminating any damage that could potentially be caused by the advancement and/or shape manipulation of the catheter while it is positioned at the implant site.

Figure 19:
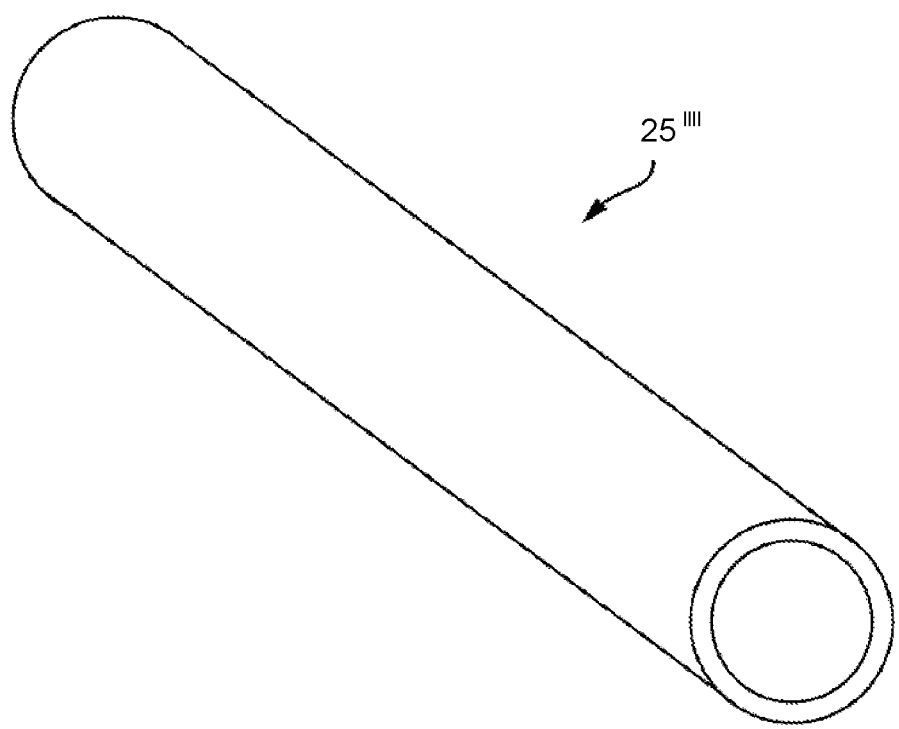
FIG. 19 shows a perspective view of an exemplary distal section of a delivery catheter usable as part of the delivery device for implanting an anchoring device.

While several of the above embodiments for the distal section of a delivery catheter include teeth and corresponding slots, other embodiments for the distal section can include no teeth nor corresponding slots. FIG. 19 is a perspective view of another exemplary distal section 25'''' that can be used for a delivery catheter. In this embodiment, the distal section 25'''' is a solid, generally cylindrical hollow tube made from a flexible material. The flexible material can be, for example, nitinol, steel, and/or plastic, or any other suitable material or combination of materials that allow the distal section 25'''' to be moved to a flexed configuration while delivering an anchoring device. While the illustrated embodiment shows the distal section 25'''' being a generally cylindrical tube, it should be understood that, in alternative embodiments, the shape of the distal section 25''' can take any suitable form that is capable of delivering an anchoring device. Some embodiments of the distal section may include linear slits and/or rectangular windows.

Figure 8:
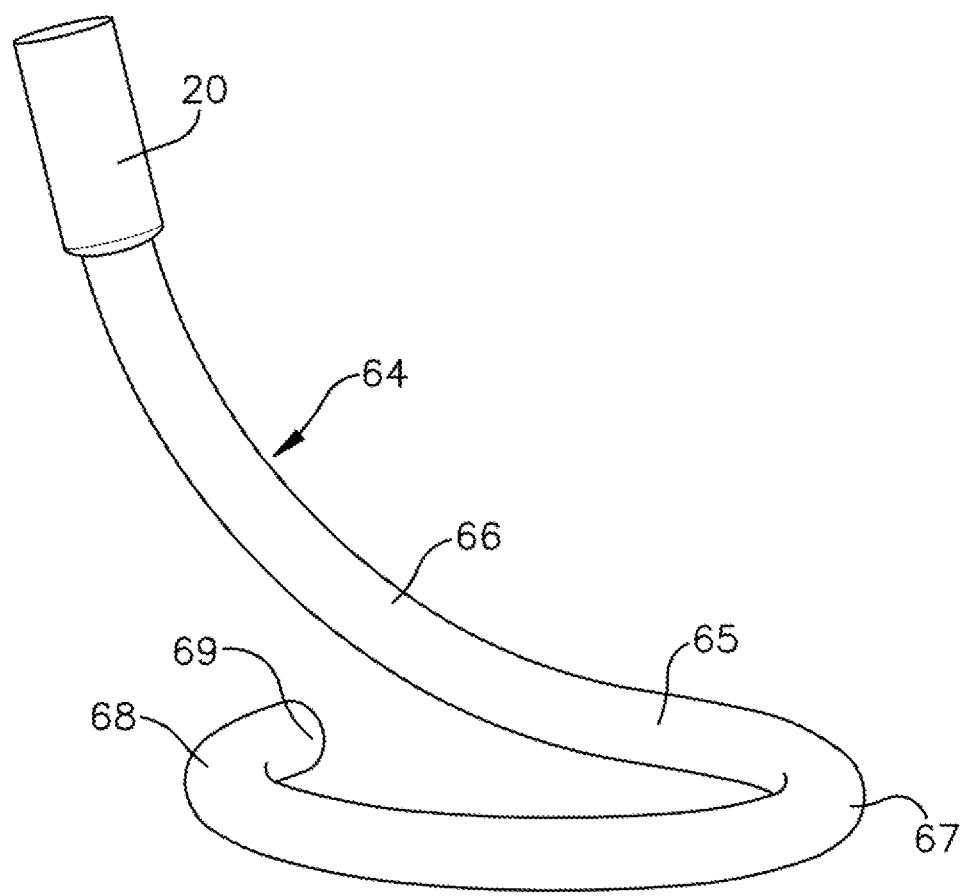
FIG. 8 shows a perspective view of a bent or curved configuration of a distal section of a delivery catheter usable for implanting an anchoring device at a native valve, e.g., using a transseptal technique.

FIG. 8 shows a perspective view of a curved configuration or a "hockey stick" configuration of a distal section 65 of a delivery catheter 64. This configuration can be used for implanting an anchoring device at a native valve (e.g., at a native mitral valve using, for example, a transseptal technique). In the "hockey stick" configuration, the distal end 65 of the delivery catheter 64 extending from a transseptal sheath 20 has four main subsections: a first flexing section that forms a shallow curved portion 66, a second flexing section that forms a circular or curved planar portion 67, a turn 68 and a flexible end portion 69. The shapes of these subsections allow the distal section 65 to navigate the delivery catheter 64 into position at a native valve (e.g., a native mitral valve) and accurately deploy an anchoring device at the native valve (e.g., at the mitral position). The distal section 65 can take any suitable form that allows the distal section to take the flexed configuration described above, such as, for example, any form described in the present application. While, in the illustrated embodiment, the distal section 65 of the delivery catheter 64 curves in a clockwise direction, in other embodiments (for example, as seen in the embodiment in FIGS. 9A-9U), the distal section 65 can instead curve in an opposite, counter-clockwise direction, e.g., at circular/curved planar portion 67 and/or turn 68.

Figure 9A:
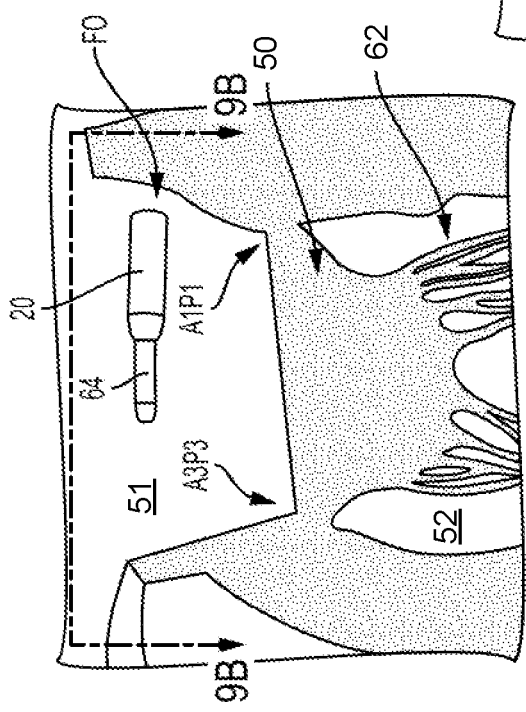
FIG. 9A is a side cutout view of a portion of a patient's heart that illustrates an exemplary delivery device entering the left atrium through the fossa ovalis in an exemplary method.
Figure 9B:
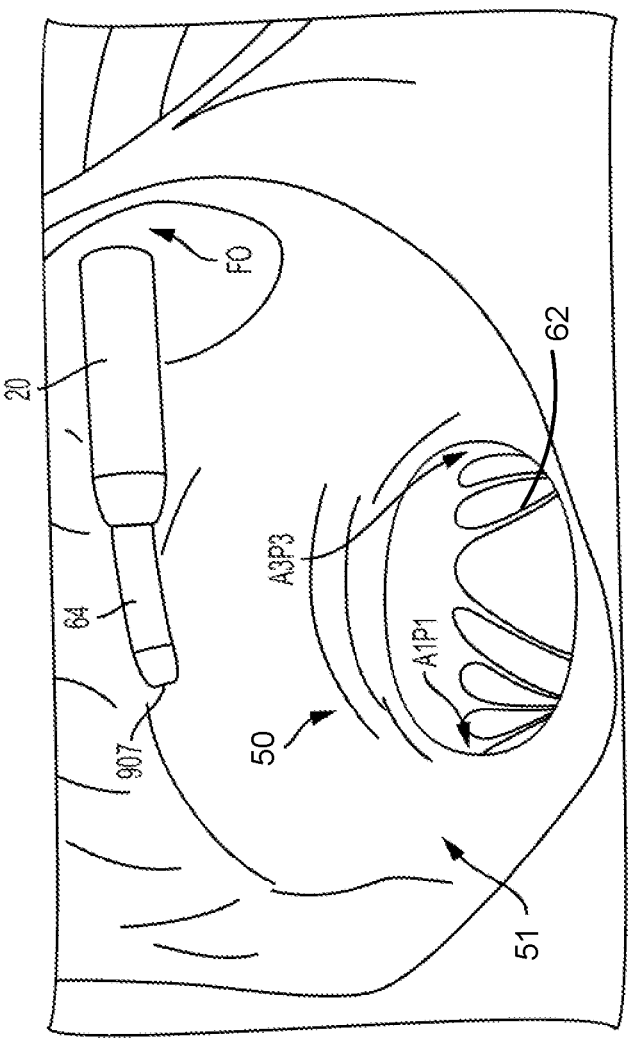
FIG. 9B illustrates the delivery device of FIG. 9A entering the left atrium of the patient's heart in the position shown in FIG. 9A, in which the delivery device is shown from a view taken along the lines B-B in FIG. 9A.
Figure 9C:
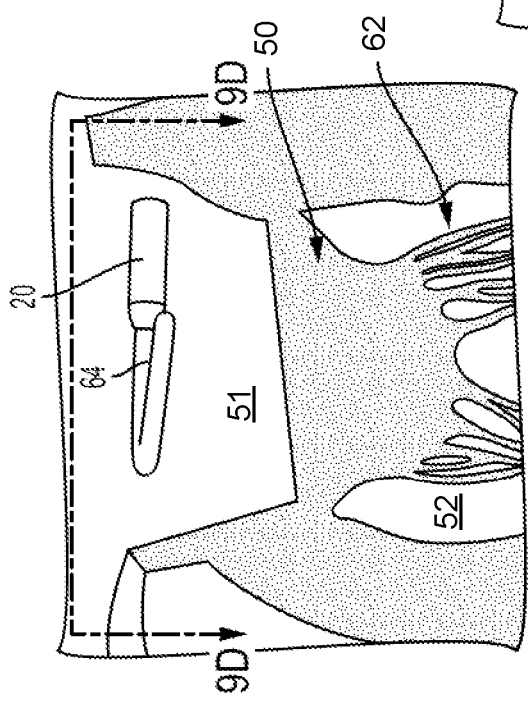
FIG. 9C illustrates the delivery device of FIG. 9A in a second position.
Figure 9D:
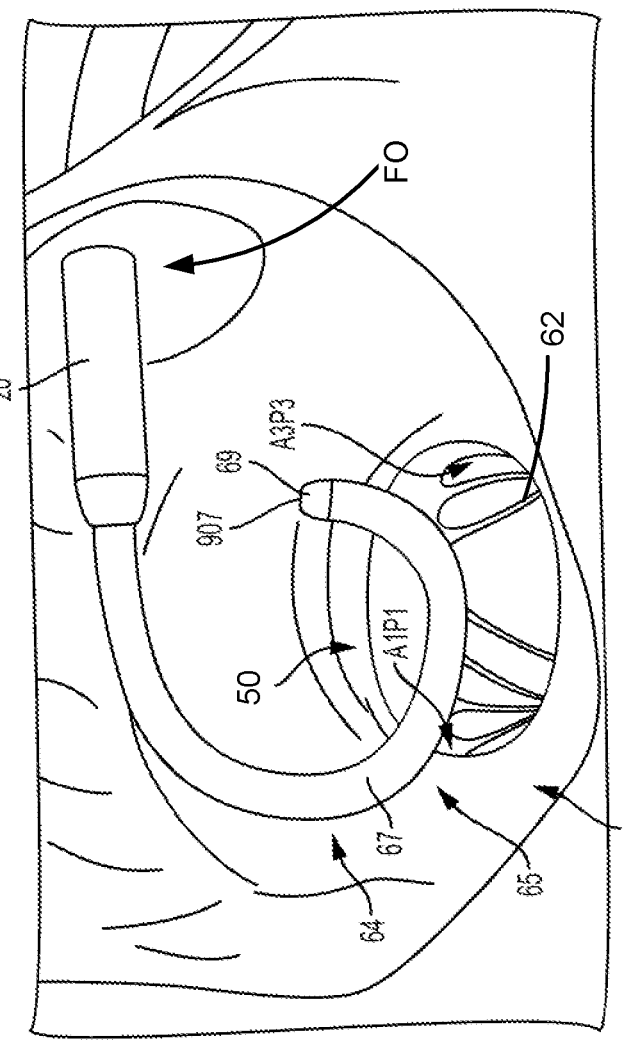
FIG. 9D illustrates the delivery device of FIG. 9A in the second position shown in FIG. 9C, in which the delivery device is shown from a view taken along the lines D-D in FIG. 9C.
Figure 9E:
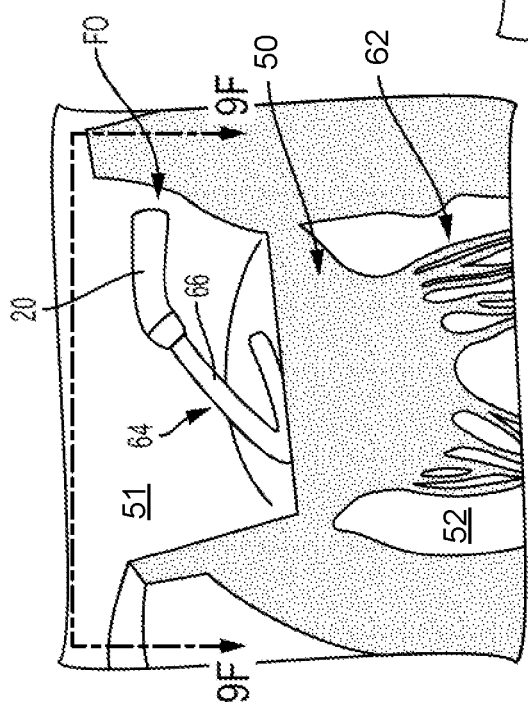
FIG. 9E illustrates the delivery device of FIG. 9A in a third position.
Figure 9F:
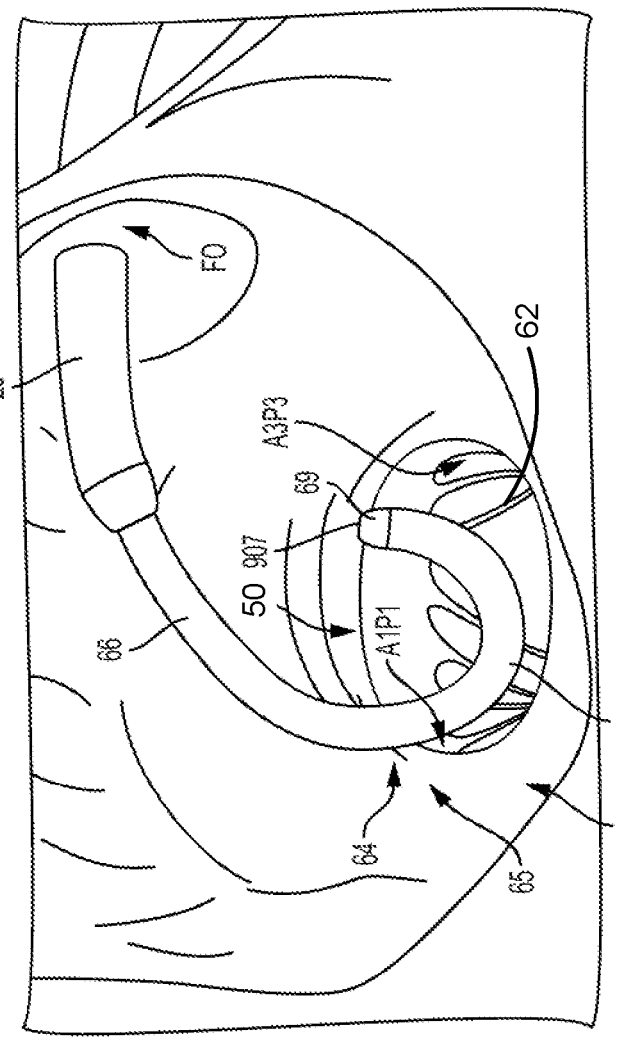
FIG. 9F illustrates the delivery device of FIG. 9A in the third position shown in FIG. 9E, in which the delivery device is shown from a view taken along the lines F-F in FIG. 9E.
Figure 91:
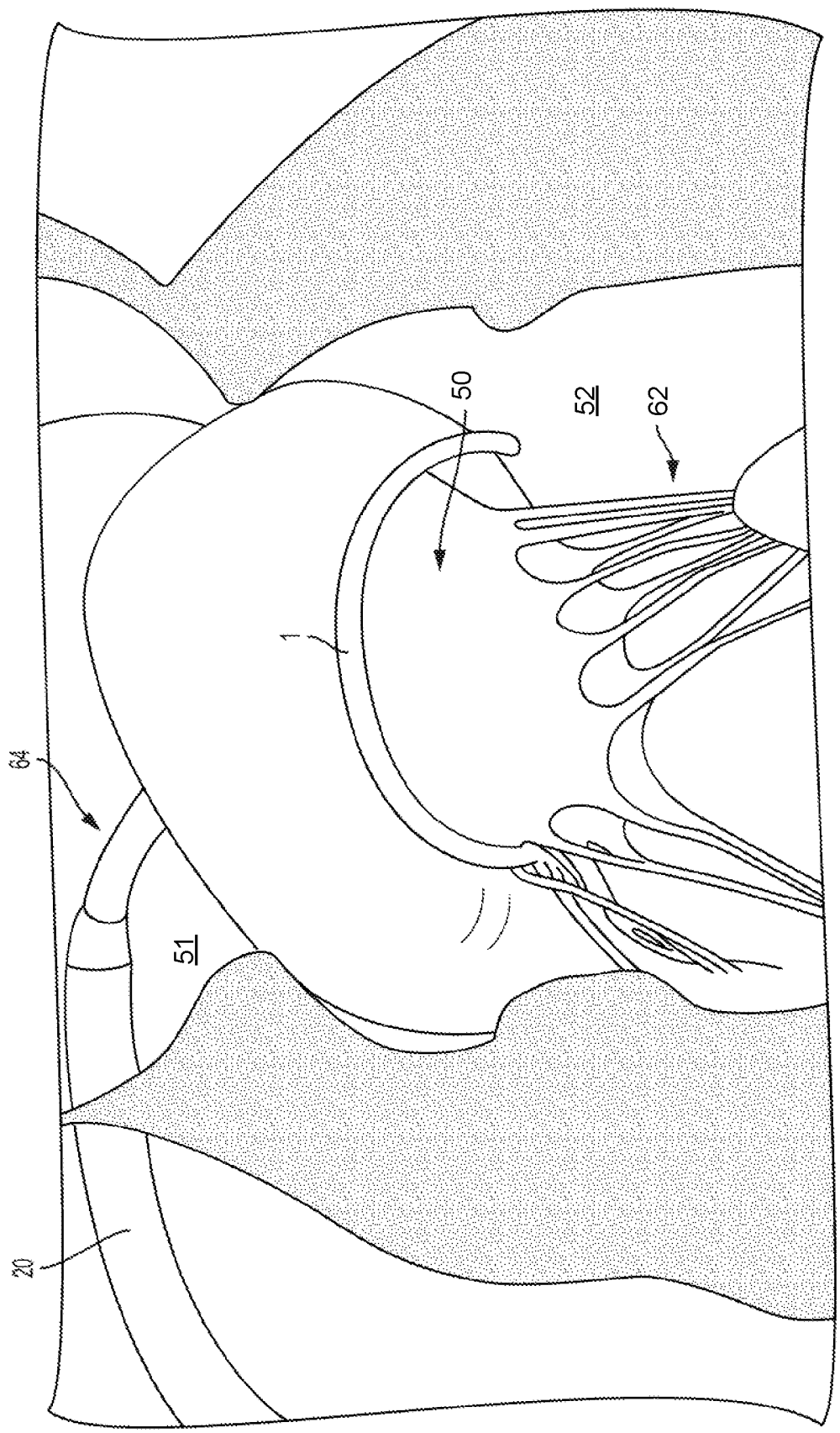
Figure 9J:
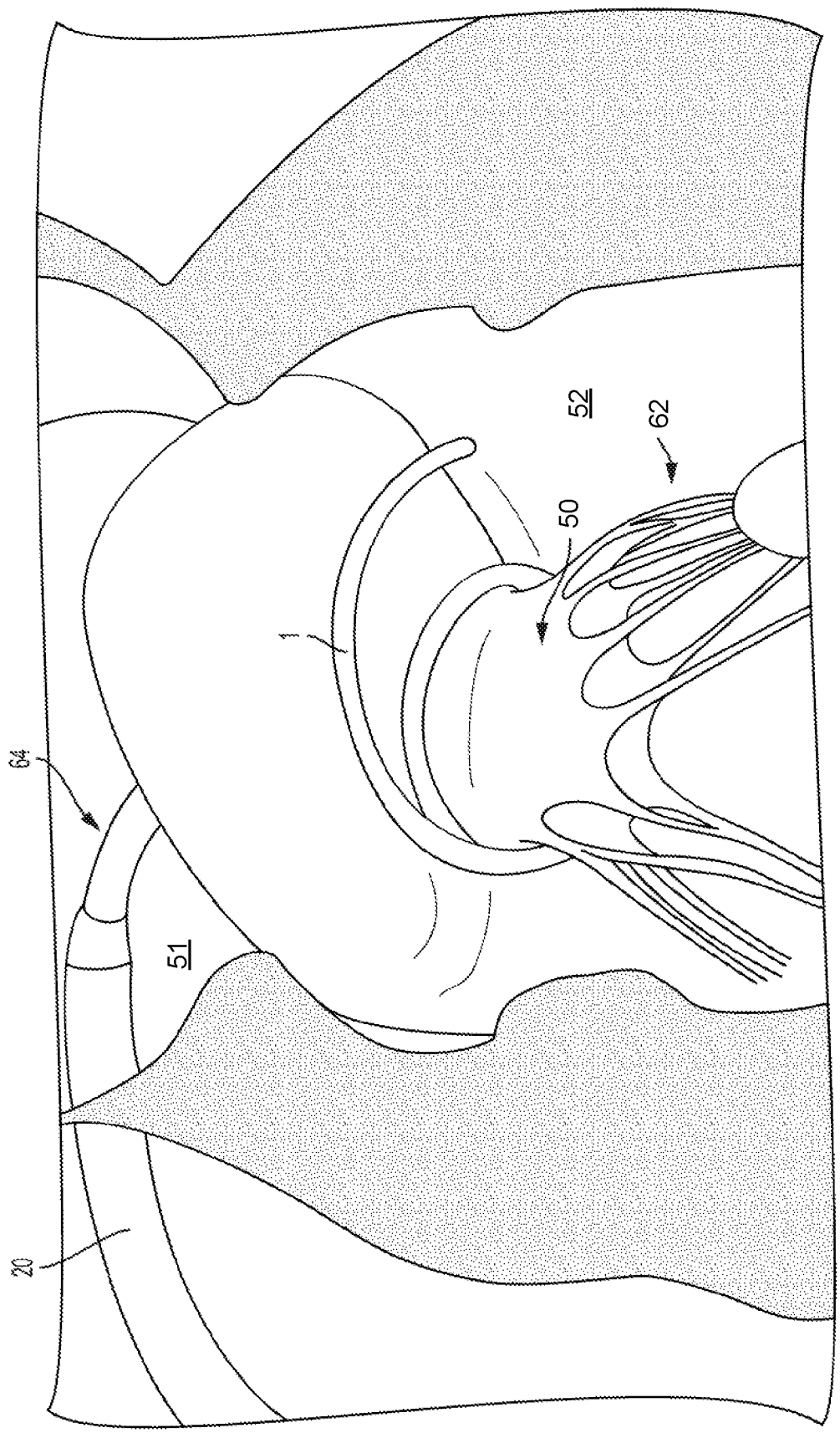
FIG. 9J illustrates the anchoring device of FIG. 9I further wrapping around the chordae tendineae and leaflets in the left ventricle of the patient's heart as it is being delivered by the delivery device of FIG. 9A.
Figure 9L:
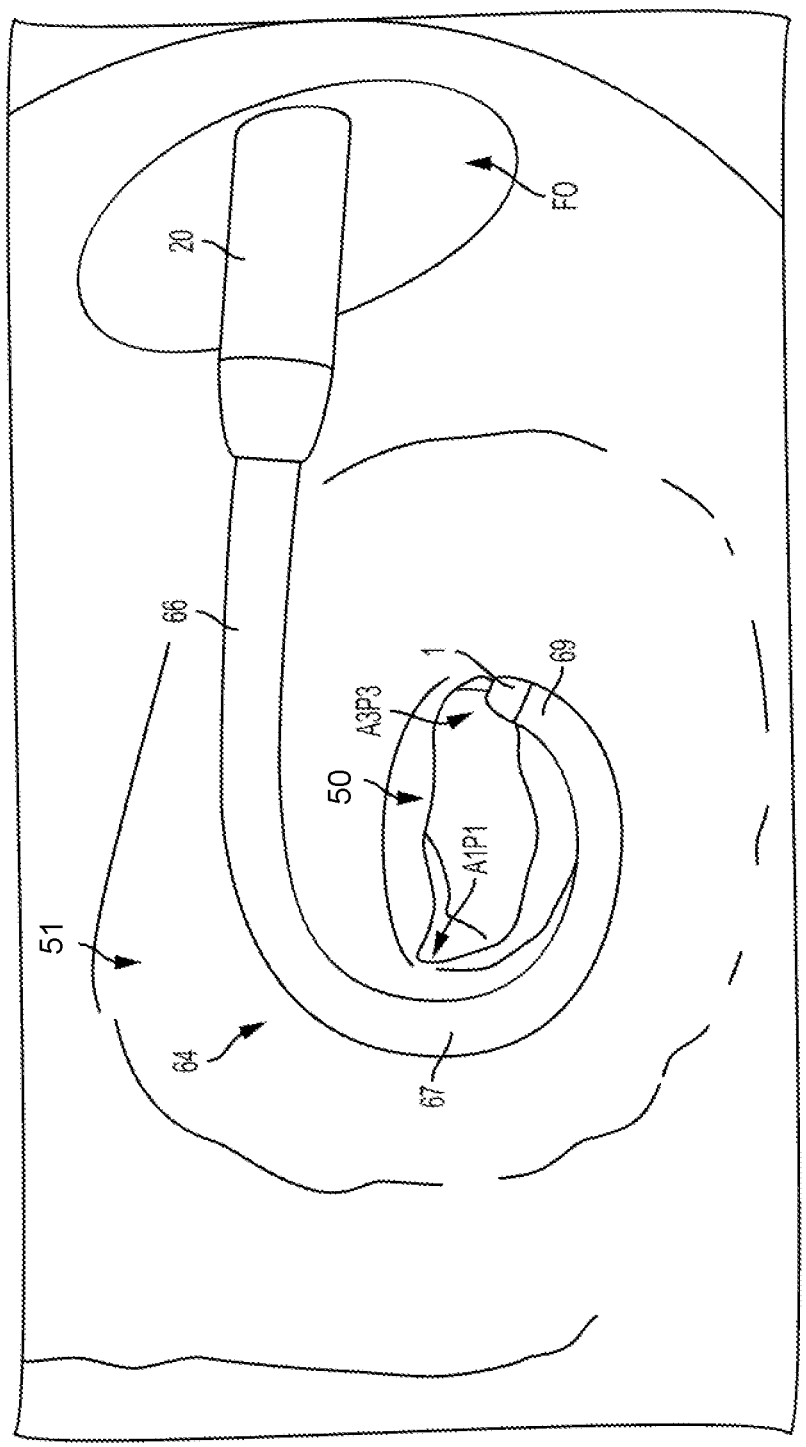
FIG. 9L is a view looking down into the patient's left atrium, illustrating the delivery device of FIG. 9A, after the anchoring device of FIG. 9I is wrapped around the chordae tendineae and leaflets in the left ventricle of the patient's heart.
Figure 9N:
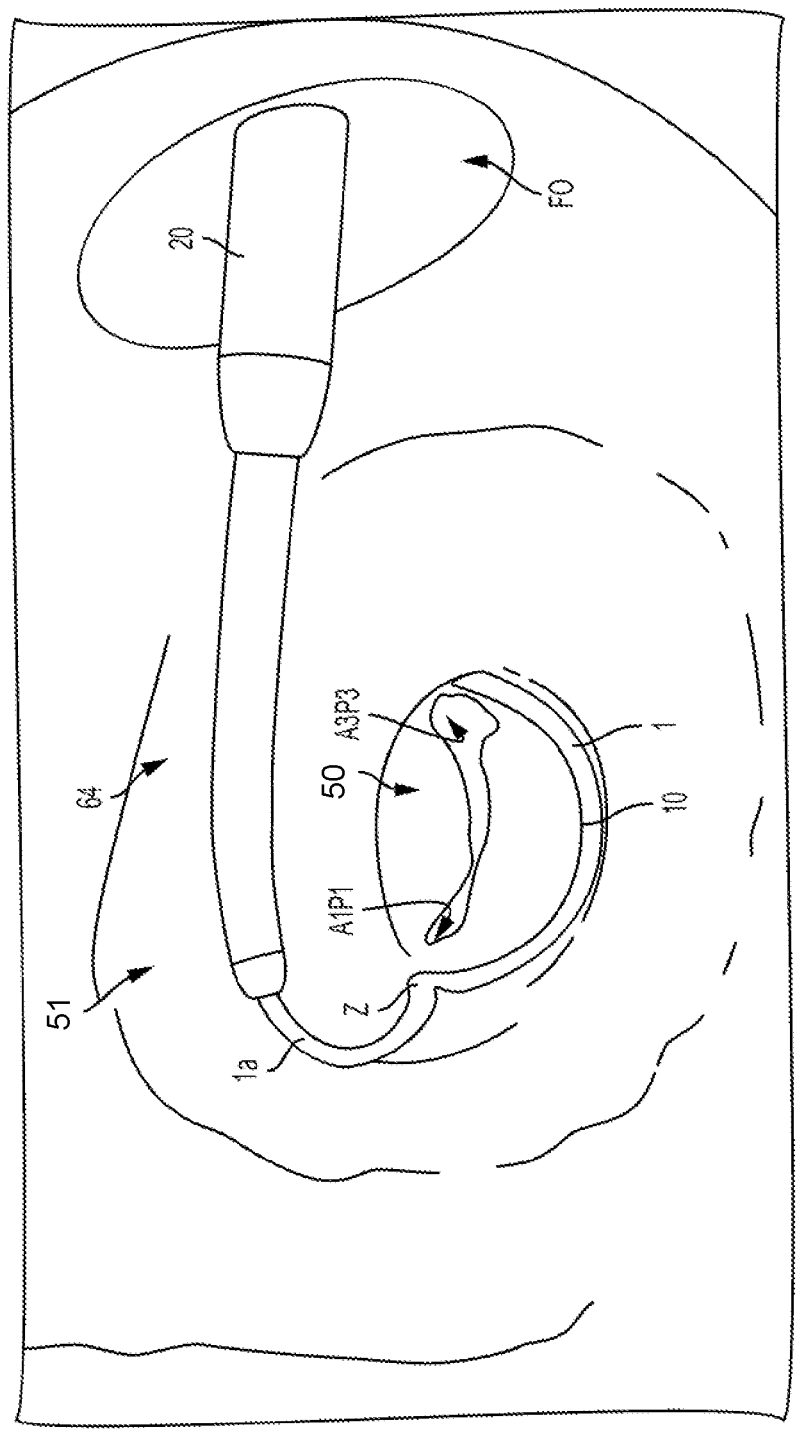
FIG. 9N illustrates the delivery device of FIG. 9A in the left atrium of the patient's heart, in which the delivery device is retracting to deliver a further portion of the anchoring device in the left atrium of the patient's heart.
Figure 90:
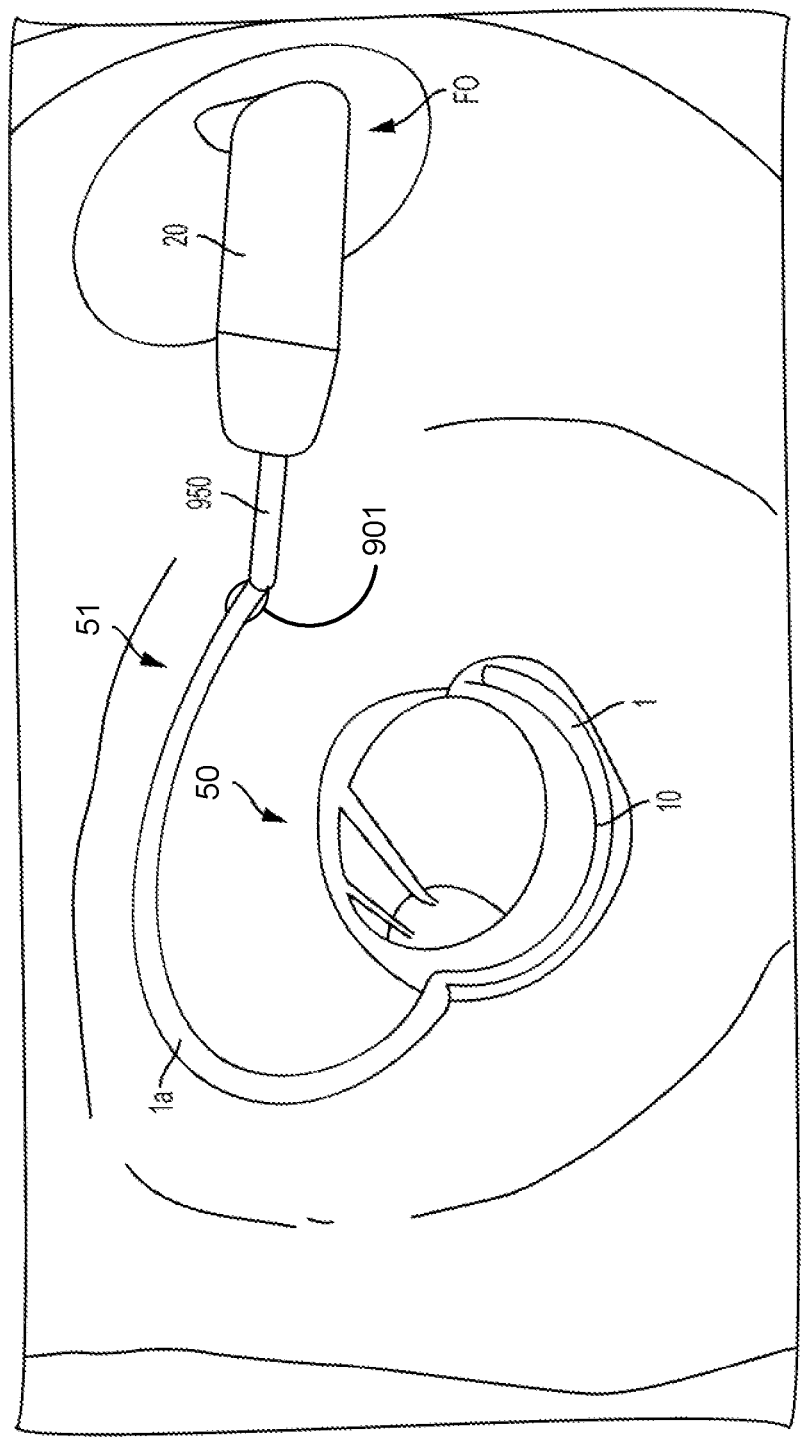
Figure 9P:
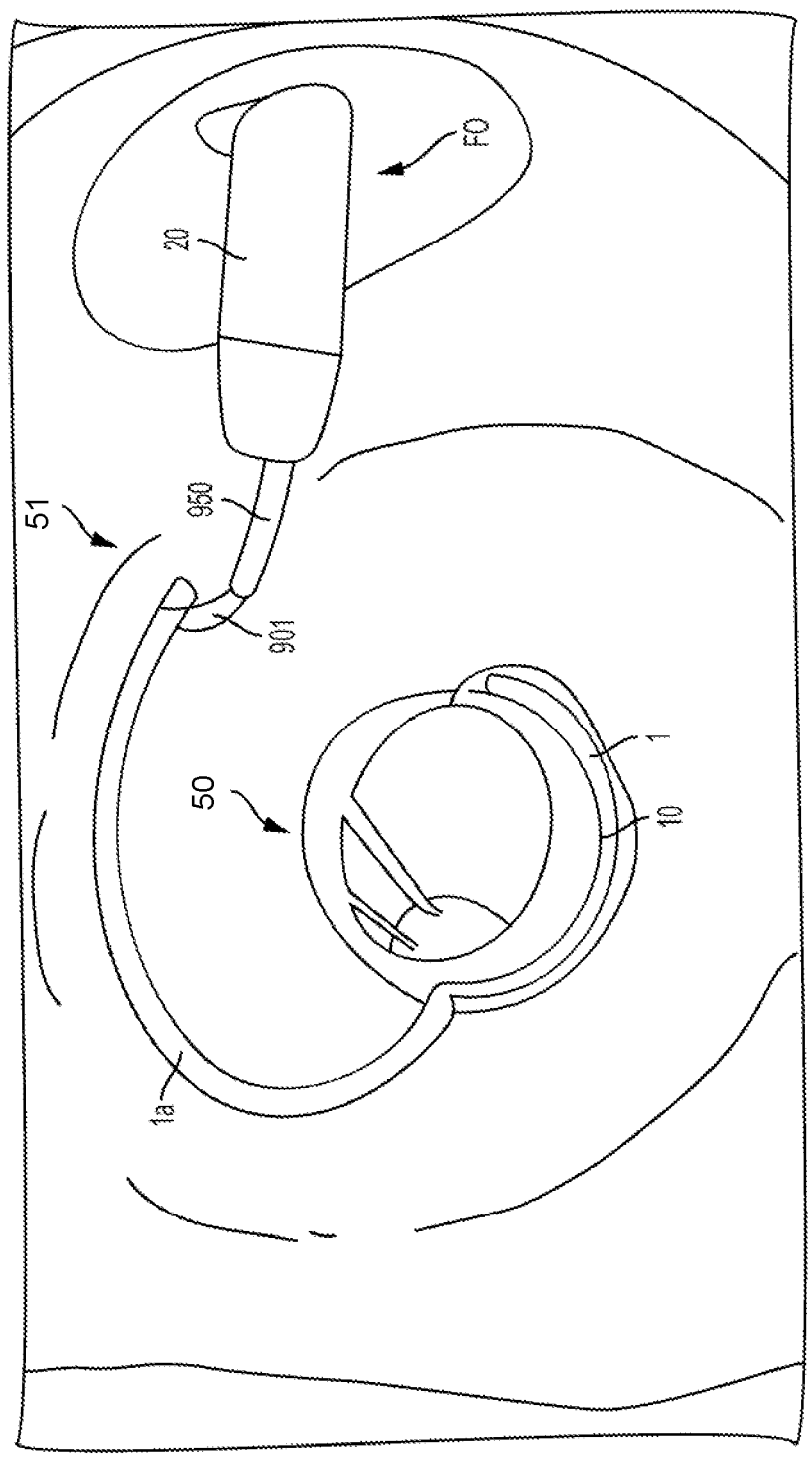
FIG. 9P illustrates the delivery device of FIG. 9A in the left atrium of the patient's heart, in which the anchoring device is fully removed from the delivery device and is loosely and removably attached to the pusher by a suture.
Figure 9Q:
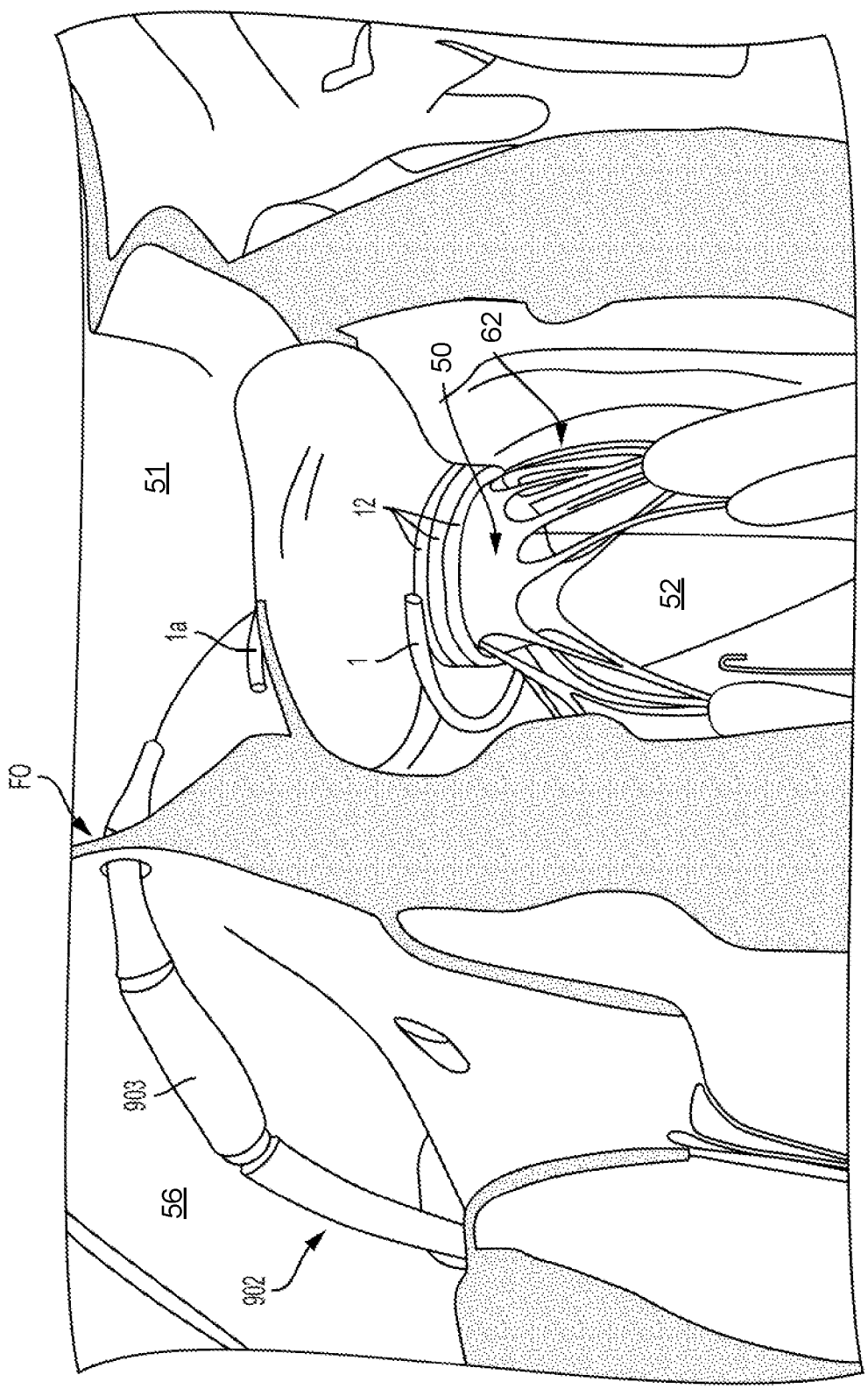
FIG. 9Q is a cutout view of the patient's heart that illustrates an exemplary embodiment of a prosthetic heart valve being delivered by an exemplary embodiment of a heart valve delivery device to the mitral valve of the patient.
Figure 9R:
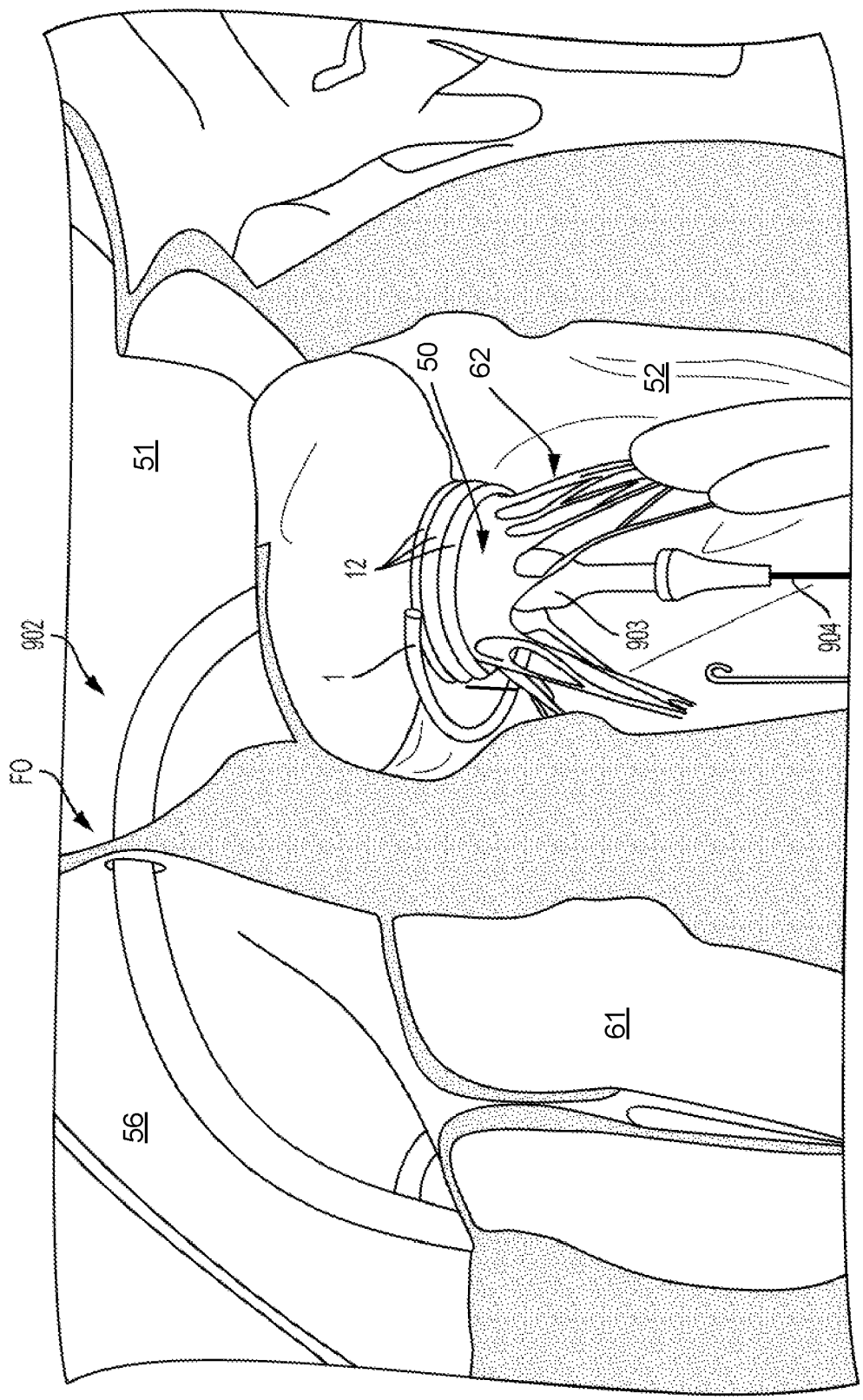
FIG. 9R illustrates the heart valve of FIG. 9Q being further delivered to the mitral valve of the patient by the heart valve delivery device.
Figure 9S:
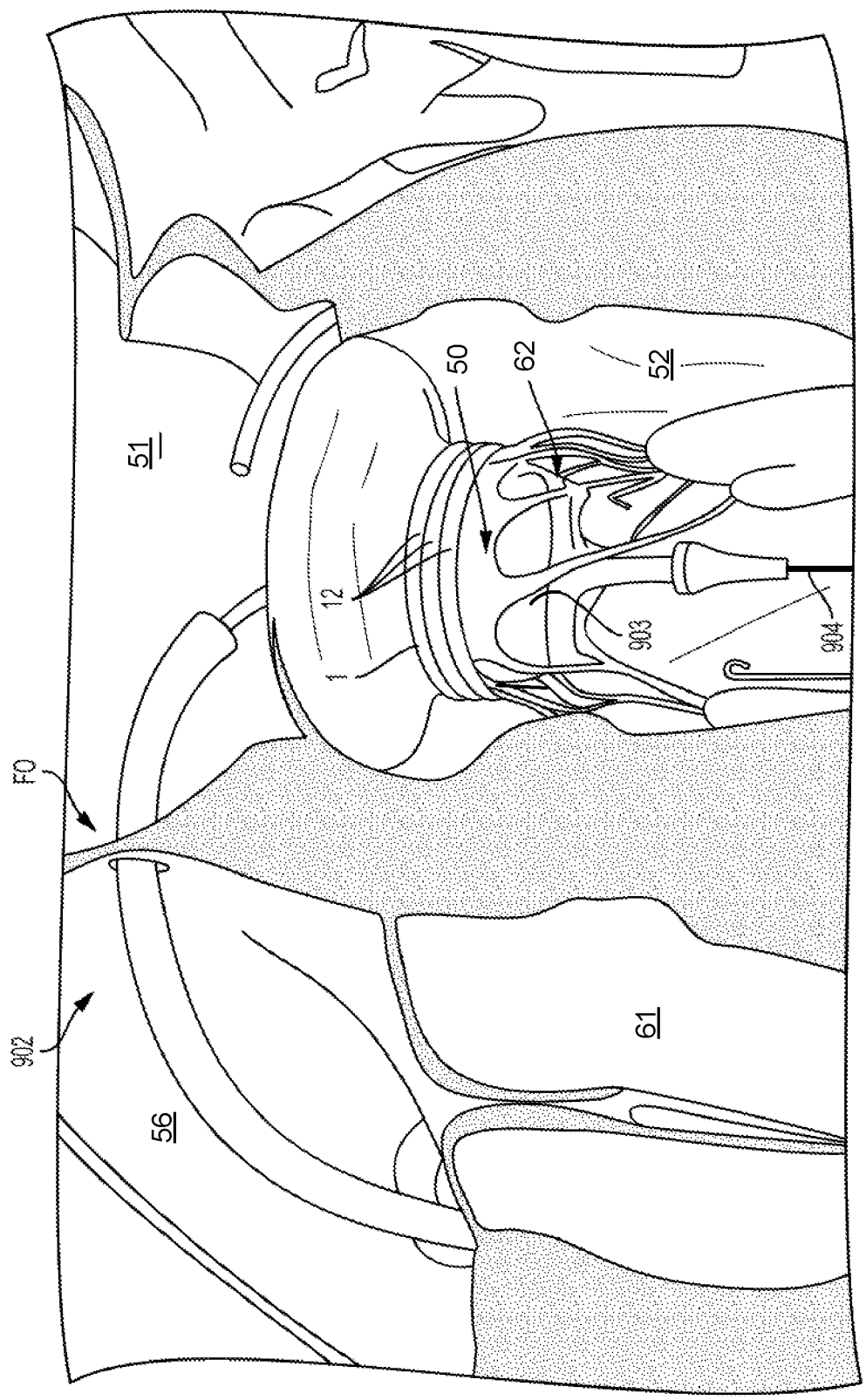
FIG. 9S illustrates the heart valve of FIG. 9Q being opened by inflation of a balloon to expand and attach the heart valve to the mitral valve of the patient.
Figure 9T:
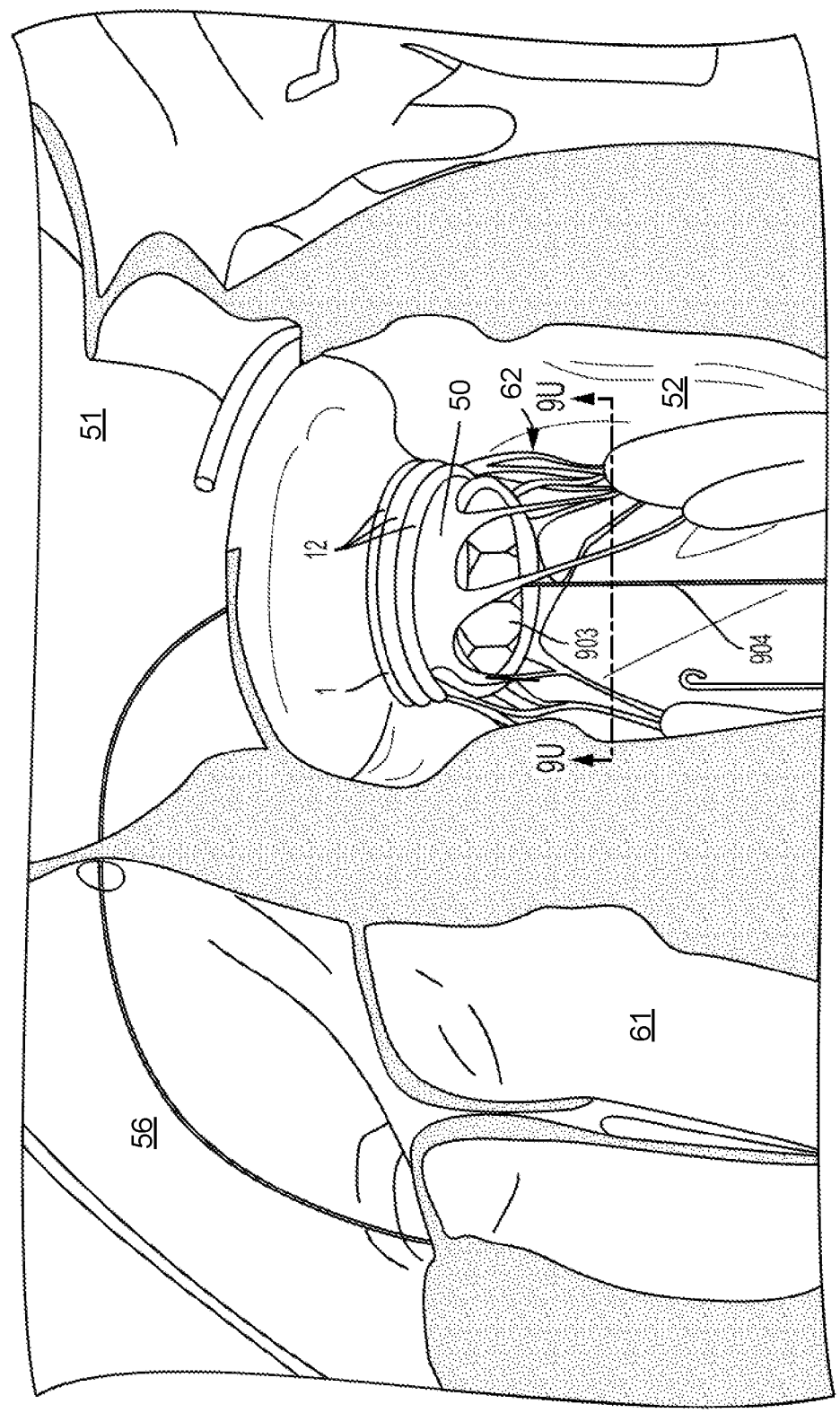
FIG. 9T illustrates the heart valve of FIG. 9Q attached to the mitral valve of the patient's heart and secured by the anchoring device of FIG. 9I.
Figure 9U:
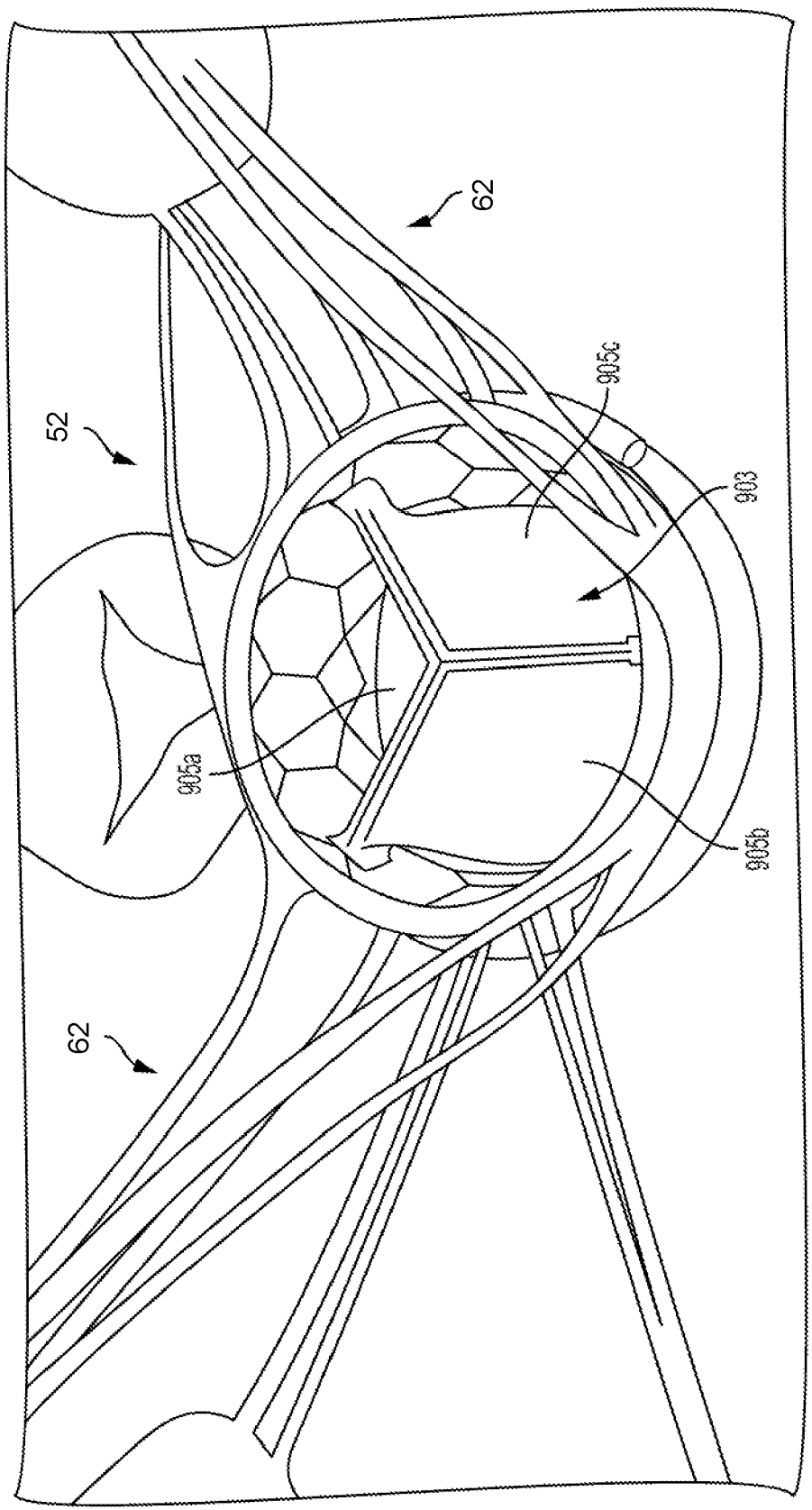
FIG. 9U is an upward view of the mitral valve from the left ventricle that illustrates the prosthetic heart valve of FIG. 9Q attached to the mitral valve of the patient's heart from a view taken along the lines U-U in FIG. 9T.

FIGS. 9A-9U illustrate another exemplary embodiment of a delivery device (which can be the same as or similar to other anchoring devices described herein) delivering and implanting an anchoring device (which can be the same as or similar to other anchoring devices described herein) at a native valve of a patient (e.g., at the native mitral valve 50 of a patient using a transseptal technique). FIG. 9A is a cutout view of the left atrium of a patient's heart that illustrates a sheath 20 (e.g., a guide sheath or transseptal sheath) passing through the interatrial septum, which can happen at the fossa ovalis (FO), and into the left atrium, and a delivery catheter 64 extending from the sheath 20. FIG. 9B illustrates the transseptal sheath 20 and the delivery catheter 64 in the position shown in FIG. 9A from a view looking down at the mitral valve 50 from the left atrium 51 (i.e., from a view taken along the line B-B in FIG. 9A). Referring to FIG. 9A, the sheath 20 enters the left atrium such that the sheath is substantially parallel with the plane of the mitral valve 50. The sheath 20 and delivery catheter 64 can take any suitable form, such as, for example, any form described in the present application.

In some embodiments, the sheath 20 can be actuated or steerable so that the sheath 20 can be positioned or bent until it makes an angle (e.g., a 30-degree angle or an approximately 30-degree angle) with respect to the septum and/or FO wall. In some embodiments, the angle orientation (e.g., 30-degree angle orientation) can be adjusted or controlled by rotating or further actuating the sheath 20, and can be adjusted to better control the orientation at which the delivery catheter 64 enters the left atrium. In other embodiments, the deflection angle of the sheath 20 relative to the septum and/or FO can be either more or less than 30 degrees, depending on each situation, and in some applications, can even be oriented at or bent to be 90 degrees relative to the septum and/or FO. In certain embodiments, the deflection angle of the sheath can be moved between about 0 degrees and about 90 degrees, such as, for example, between about 5 degrees and about 80 degrees, such as between about 10 degrees and 70 degrees, such as between about 15 degrees and about 60 degrees, such as between about 20 degrees and about 50 degrees, such as between about 25 degrees and about 40 degrees, such as between about 27 degrees and about 33 degrees.

Referring to FIGS. 9C-9D, after the outer sheath or guide sheath 20 passes through the septum and/or FO and is placed in a desired position, the delivery catheter 64 exits and extends from the sheath 20. The delivery catheter is controlled such that the delivery catheter includes a distal end 65 having a circular or curved planar portion 67. In the illustrated embodiment, the distal end 65 of the delivery catheter 64 is moved such that the distal end 65 curves in a counter-clockwise direction to create the circular/curved planar portion 67 (the anchoring device can also coil in a counter-clockwise direction). In alternative embodiments, the distal end 65 is moved such that the distal end 65 curves in the clockwise direction to create the circular/curved planar portion 67 (in these embodiments the anchoring device can also coil in a clockwise direction).

Referring to FIGS. 9E-9F, the delivery catheter 64 is also extended downward by a shallow curved portion 66 of the distal end 65. As shown in FIG. 9E, the delivery catheter 64 is extended downward until the circular/curved planar portion 67 of the distal end 65 nears the plane of the mitral valve 50, which is generally about 30 to 40 mm below the FO wall. In some situations, however, the plane of the mitral valve may be less than 30 mm below the FO or more than 30 mm below the FO. In certain embodiments, the delivery catheter 64 is configured to extend 60 mm or less from the outer sheath, such as, for example, 50 mm or less, such as 45 mm or less, such as 40 mm or less, such as 35 mm or less, such as 30 mm or less, such as 25 mm or less, such as 20 mm or less. In some embodiments, the maximum extension of the delivery catheter 64 from the exterior sheath is between about 20 mm and about 60 mm, such as, for example, between about 25 mm and about 50 mm, such as between 30 mm and about 40 mm. In certain embodiments, the delivery catheter 64 can be moved to any of the various configurations described herein by engaging one or more actuation points 70, 71 of the delivery catheter 64.

The circular/curved planar portion 67 is advanced or lowered to lie near, on top of, or substantially on top of the plane of the mitral valve 50. When lowered to or near the level of the annulus, the planar portion 67 or a plane of the planar portion 67 can be parallel or nearly parallel (e.g., planar or nearly planar) with a plane of the annulus, or the planar portion 67 can be slightly upwardly angled relative to the plane of the annulus. The delivery catheter 64 also curves to circle its way back towards commissure A3P3. The delivery catheter 64 can be moved to create the circular/curved planar portion 67 and/or the shallow curved portion 66 by any suitable means, such as, for example, a pull wire and ring system, or any other suitable means, including those described elsewhere in the present application. While the illustrated embodiment shows the distal end 65 being moved to create the circular or curved planar portion 67 prior to distal end being moved to create the shallow curved portion 66, it should be understood that the downward extension of the distal end 65 to create the shallow curved portion 66 can occur prior to the distal end 65 being curved in the counter-clockwise direction to create the circular or curved planar portion 67.

Referring to FIGS. 9G-9H, an actuation point 70 (and/or one or more other actuation points) can be located between the shallow curved portion 66 and the circular/curved planar portion 67 that allows the distal section 65 to be adjusted. In the illustrated embodiment, the actuation point 70 can be adjusted to cause the planar portion 67 and the flexible end 69 to be angled in a somewhat downward direction such that the flexible end 69 and distal tip 907 extend below the annulus (or below an upper plane of the annulus) in the direction of and/or into the commissure A3P3 of the mitral valve 50. That is, the first actuation point 70 can be actuated such that the planar portion 67 (and, as a result, the flexible end 69) is angled downward toward the commissure A3P3 and positioned at or near (e.g., extending slightly into or through, such as 1-5 mm or less) the commissure. Additionally or alternatively to further actuating point 70, the delivery device (e.g., the sheath and/or delivery catheter) can be torqued or rotated to cause the angle of the circular/curved planar portion 67 to angle downward toward and/or into the commissure as desired. This torqueing or rotating can sometimes be necessary to get the angles right if the actuations of the curved portions does not fully position the distal region of the catheter as desired. In some embodiments, a second actuation point 71 can be located between the portion 67 and the flexible end 69.

FIG. 9I illustrates the delivery catheter 64 deploying an exemplary embodiment of an anchoring device 1 through the commissure A3P3 and around the chordae tendineae 62 and native leaflets in the left ventricle 52 of the patient's heart. The anchoring device 1 or a lower end or encircling coil/turn of the anchoring device with a larger diameter or radius of curvature exits the distal opening of the delivery catheter 64 and begins to take its shapeset or shape memory form in the direction of the circular or curved planar portion 67 of the delivery catheter 64.

For the anchoring device 1 to move through the commissure A3P3 of the mitral valve 50, the delivery catheter 64 is positioned such that the circular/curved planar portion 67 and the distal opening of the flexible end 69 of the delivery catheter 64 are angled downward, and the distal opening of the flexible end 69 is directed toward and/or into the commissure A3P3. As a result of the circular/curved planar portion 67 and the distal opening of the flexible end 69 being in a downward direction, the anchoring device 1 exits the delivery catheter 64 in a downward direction. After the anchoring device 1 exits the delivery catheter 64, the anchoring device 1 begins to curve to take its shapeset or shape memory form. Because the circular/curved planar portion is angled in a downward direction, the anchoring device 1 begins to curve in an upward direction after about ½ turn of the anchoring device is deployed, as illustrated by FIG. 9I. To prevent the anchoring device 1 or lower end/encircling coil/turn from engaging the mitral valve 50 in an upward direction as it is being delivered out of the delivery catheter 64, once the anchoring device begins to be wrapped around the chordae tendineae 62 (as shown in FIG. 9I), the delivery catheter 64 can be moved (e.g., by moving at actuation point 70) such that the circular/curved planar portion 67 is substantially parallel with the plane of the mitral valve 50 (see FIG. 9L). This can be done by actuating at point 70 and/or torqueing or rotating the delivery device or a portion thereof (e.g., the delivery catheter) to adjust the angle of the planar portion 67 as desired.

Referring to FIG. 9J, after the circular/curved planar portion 67 is moved to be substantially planar with the mitral valve annulus, the anchoring device 1 can be further deployed from the delivery catheter 64, such that the anchoring device wraps around the chordae tendineae 62 in a position that is substantially parallel to the plane of the mitral valve 50. This prevents the anchoring device from curving in an upward direction and engaging the underside of the mitral valve annulus and/or the top wall of the left ventricle.

Referring to FIG. 9K, the anchoring device 1 is disposed around the chordae tendineae 62 to loosely position the anchoring device on the ventricular side of the mitral valve for holding a heart valve. In the illustrated embodiment, the anchoring device 1 is disposed in the left ventricle 52 such that three functional coils 12 of the anchoring device are wrapped closely around the chordae tendineae and/or native leaflets. The lower end turn/coil or encircling turn/coil can be seen extending outwardly somewhat because of its larger radius of curvature. In some embodiments, the anchoring device 1 can include less than three coils 12 or more than three coils 12 that are disposed around the chordae tendineae and/or leaflets.

FIG. 9L illustrates the delivery catheter 64 in the left atrium 51 in a position after the coils 12 of the anchoring device are disposed around the chordae tendineae 62 and native leaflets (as shown in FIG. 9K). In this position, the circular/curved planar portion 67 of the delivery catheter 64 is substantially parallel with the plane of the mitral valve 50 and the flexible end 69 is located at or near (e.g., extending slightly into or through, such as 1-5 mm or less) the commissure A3P3 of the mitral valve 50.

Referring to FIG. 9M, after the delivery catheter 64 and the anchoring device 1 are positioned as shown in FIGS. 9K-9L, the delivery catheter is translated or retracted axially along the anchoring device in the direction X and into the outer sheath 20. Translation or retracting of the delivery catheter can causes the portions of the anchoring device positioned one the atrial side of the native valve (e.g., in the atrium) to be unsheathed and released from the delivery catheter. For example, this can unsheathe and release any upper portion of any functional coil and/or upper coil positioned on the atrial side of the native valve (if any). In one exemplary embodiment, the anchoring device 1 does not move or does not substantially move as the delivery catheter is translated, e.g., a pusher can be used to hold the anchoring device in place and/or inhibit or prevent retraction of the anchoring device when the delivery catheter is retracted.

Referring to FIG. 9N, in the illustrated example, translation or retraction of the delivery catheter can also unsheathe/release any upper end coil/turn (e.g., a larger diameter stabilization coil/turn) of the anchoring device 1 from the delivery catheter. As a result of the unsheathing/releasing, the atrial side of the anchoring device or upper coil (e.g., stabilization coil with a larger diameter or radius of curvature) extends out of the delivery catheter 64 and begins to assume its preset or relaxed shape-set/shape-memory shape. The anchoring device can also include an upward extending portion or connecting portion that extends upward from a bend Z and can extend and/or bridge between an upper end stabilization coil/turn and other coil/turns of the anchoring device (e.g., functional coils/turns). In some embodiments, the anchoring device can have only one upper coil on the atrial side of the native valve. In some embodiments, the anchoring device can include more than one upper coil on the atrial side of the native valve.

Referring to FIG. 9O, the delivery catheter 64 continues to translate back into the outer sheath or guide sheath 20, which causes the upper portion of the anchoring device 1 to be released from inside the delivery catheter. The anchoring device is connected closely to the pusher 950 by an attachment means, such as suture/line 901 (other attachment or connection means can also be used, such as in FIGS. 17A-18C). The upper end coil/turn or stabilization coil/turn is shown as being disposed along the atrial wall to temporarily and/or loosely hold the position or height of the anchoring device 1 relative to the mitral valve 50.

Referring to FIG. 9P, the anchoring device 1 is fully removed from a lumen of the delivery catheter 64, and slack is shown in a suture/line 901 that is removably attached to the anchoring device 1, e.g., suture/line 901 can loop through an eyelet at the end of the anchoring device. To remove the anchoring device 1 from the delivery catheter 64, the suture 901 is removed from the anchoring device. However, before the suture 901 is removed, the position of the anchoring device 1 can be checked. If the position of the anchoring device 1 is incorrect, the anchoring device can be pulled back into the delivery catheter by the pusher 950 (e.g., a pusher rod, pusher wire, pusher tube, etc.) and redeployed.

Referring to FIG. 9Q, after the delivery catheter 64 and the outer sheath 20 are detached from the anchoring device 1, a heart valve delivery device/catheter 902 can be used to deliver a heart valve 903 to the mitral valve 50. The heart valve delivery device 902 may utilize one or more of the components of the delivery catheter 64 and/or outer or guide sheath 20 or the delivery device 902 may be independent of the delivery catheter 64 and outer or guide sheath. In the illustrated embodiment, the heart valve delivery device 902 enters the left atrium 51 using a transseptal approach.

Referring to FIG. 9R, the heart valve delivery device/catheter 902 is moved through the mitral valve 50 such that heart valve 903 is placed between the leaflets of the mitral valve and the anchoring device 1. The heart valve 903 can be guided along a guide wire 904 to the deployment position.

Referring to FIG. 9S, after the heart valve 903 is placed in the desired position, an optional balloon is expanded to expand the heart valve 903 to its expanded, deployed size. That is, the optional balloon is inflated such that the heart valve 903 engages the leaflets of the mitral valve 50 and forces the ventricular turns outward to an increased size to secure the leaflets between the heart valve 903 and the anchoring device. The outward force of the heart valve 903 and the inward force of the coil 1 can pinch the native tissue and retain the heart valve 903 and the coil to the leaflets. In some embodiments, a self-expanding heart valve can be retained in a radially compressed state within a sheath of the heart valve delivery device 902, and the heart valve can be deployed from the sheath, which causes the heart valve to expand to its expanded state. In some embodiments, a mechanically expandable heart valve is used or a partially mechanically expandable heart valve is used (e.g., a valve that may expand by a combination of self-expansion and mechanical expansion).

Referring to FIG. 9T, after the heart valve 903 is moved to its expanded state, the heart valve delivery device 902 and the wire 904 (still shown in FIG. 9T) are removed from the patient's heart. The heart valve 903 is in a functional state and replaces the function of the mitral valve 50 of the patient's heart.

FIG. 9U shows the heart valve 903 from an upward view in the left ventricle 52 along the lines U-U in FIG. 9T. In FIG. 9U, the heart valve 903 is in the expanded and functional state. In the illustrated embodiment, the heart valve 903 includes three valve members 905*a-c* (e.g., leaflets) that are configured to move between an open position and a closed position. In alternative embodiments, the heart valve 903 can have more than three valve members or less than three valve members that are configured to move between an open position and a closed position, such as, for example, two or more valve members, three or more valve members, four or more valve members, etc. In the illustrated embodiment, the valve members 905*a-c* are shown in the closed position, which is the position the valve members are in during the systolic phase to prevent blood from moving from the left ventricle and into the left atrium. During the diastolic phase, the valve members 905*a-c* move to an open position, which allows blood to enter the left ventricle from the left atrium.

While the embodiment illustrated in FIGS. 9A-9U show the delivery catheter 64 delivering an anchoring device 1 through the commissure A3P3, it should be understood that the delivery device 64 can take a configuration and be positioned to deliver the anchoring device 1 through the commissure A1P1, such that the anchoring device 1 can be wrapped around the chordae tendineae in the left ventricle of the patient's heart. In addition, while the illustrated embodiments show the delivery catheter 64 delivering an anchoring member 1 to the mitral valve and the heart valve delivery device 902 delivering a heart valve 903 to the mitral valve 50, it should be understood that the anchoring device 1 and the heart valve 903 can be used mutatis mutandis to repair the tricuspid valve, the aortic valve, or the pulmonary valve.

In one embodiment, the distal section 65 of the delivery catheter 64 can be a solid, generally cylindrical hollow tube (e.g. the distal section 25'''' described in FIG. 19).

The guide sheaths and/or the distal sections of the various delivery catheters herein can include one or multiple pull wires (e.g., 2-6 pull wires) to control or actuate the delivery catheters to desired configurations. For example, distal sections of the various delivery catheters herein can have a two-pull wire system (e.g., the two-pull wire system described in FIGS. 20A-23). For example, the configuration shown in FIGS. 9A-9U or the "hockey stick" shape configuration shown in FIG. 8 or any other configuration described in the present application can also be achieved by using a flexible tube catheter constructed with two pull rings positioned, for example, at or near the actuation points 70, 71 discussed above. The pull rings can be engaged with or connected to respective pull wires. The pull wires can be positioned 90° away from one another in a circumferential direction around the delivery catheter. A first pull ring that is positioned, for example, approximately halfway along the distal section 65, can be actuated by a first pull wire to pull the distal regions of the delivery catheter onto the native valve plane (e.g., the mitral plane), while a second pull ring positioned further distally, at or near the distal tip 907 of the delivery catheter, can be actuated by another pull wire to make the catheter curve in a different direction, for example, around the native valve plane (e.g., around the mitral plane) and towards a desired commissure (e.g., the mitral commissure A3P3) and further, if necessary.

In some embodiments, the two pull rings can be connected by a spine that is implemented on a radially opposite side of one of the pull wires, for example, opposite the pull wire for the distalmost pull ring. Such an added spine can restrict the relative movement between the pull rings, and help to better control the direction of deflection caused by pulling the pull wire for the distalmost pull ring, and preventing deflection of the flexible distal section in a direction perpendicular to the mitral plane, or in otherwise unintended directions. While the embodiment described above can include three pull rings and two pull wires, it should be understood that any number of pull rings and/or pull wires can be used to create the various configurations described herein. In addition, it should be understood that any suitable number of spines can be used to restrict the relative movement between the pull rings In some embodiments, the distal section 65 can be a laser cut hypotube (similar to the laser cut catheters described in FIGS. 4-7 above), arranged in a pattern such that, when bent, the distal section forms any of the various configurations described herein (e.g., the configurations described in FIGS. 9A-9U, the "hockey stick configuration, etc.). Also as discussed, such laser cut distal section can have two or more actuation points that can be actuated independent from one another, for example, with separate pull wires that are, for example, controlled by separate controls (e.g., knobs, tabs, inputs, buttons, levers, switches, etc.) or other mechanisms, in order to effectuate the dual directional deflections in the distal end in the fully bent configuration (e.g., the one curve being towards the mitral plane, and the other curve being the circular portion that curves generally around the mitral annulus).

In some embodiments, the entire distal section 65 does not need to be constructed as a laser cut hypotube. For example, the distal section 65 can include a first flexible straight section proximal to the shallow curved portion 66, an optional small laser cut elbow portion making up the shallow curved portion 66 to help bend the distalmost regions of the catheter onto the mitral plane, and then a second flexible section extending to the distal tip with the ability to curve along the mitral plane so as to point the end of the catheter towards commissure A3P3. The first flexible section allows the distal section 65 to get near the mitral plane after exiting the transseptal sheath 20, and is flexible enough to be pushed and advanced through the sheath 20, but still rigid enough to resist being affected by the anchoring device when the anchoring device is being advanced and delivered through the catheter. The first flexible section can be constructed, for example, with a polyether block amide (PEBAX) having a hardness of approximately SOD, that is coated over a coiled or braided tube. Meanwhile, the small laser cut elbow portion can have a maximum deflection of approximately 150° to assist in bringing the distal regions of the catheter onto the mitral plane. Lastly, the second flexible section can extend to the distal tip of the delivery catheter, and be configured to flex to point the catheter towards commissure A3P3, as well as to potentially flex further to assist with chordae encircling by the anchoring device, similarly as has already been discussed above. The second flexible section can also be constructed, for example, with PEBAX, with for example a hardness of approximately 55D, and that is also reflowed over a coiled or braided tube. Using this configuration can still yield a distal section 65 that can be shaped and actuated substantially similarly to the laser cut hypotube discussed above, without the need to form the entire distal section 65 as a laser cut hypotube, or any portion from a laser cut hypotube.

While the delivery catheter 64 having a distal section 65 is described using the embodiments described above, it should be understood that the embodiment described above are only exemplary. The delivery catheter 64 can take any suitable form that is capable of creating the shape configurations described herein. In addition, the delivery catheter can be constructed with any suitable material that is capable of creating the shape configurations described herein.

Figure 10:
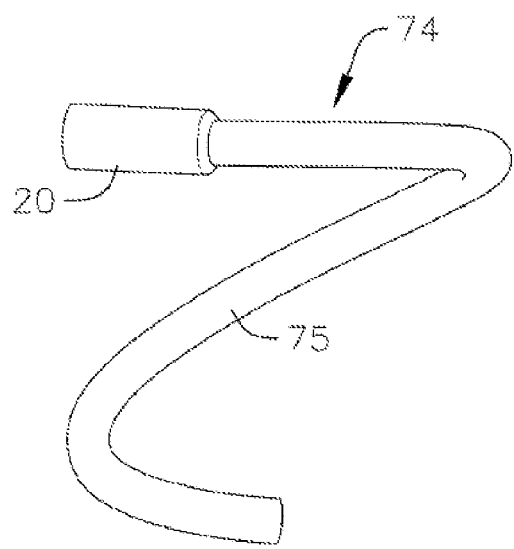
FIG. 10 shows a perspective view of a spiral configuration of a distal section of a delivery catheter that can be used for implanting an anchoring device at a native valve, which can optionally be used during a transseptal technique.

FIG. 10 shows a perspective view of an exemplary distal section 75 of a delivery catheter 74 (which can be the same as or similar to other delivery catheters described herein) for implanting an anchoring device (which can be the same as or similar to other anchoring devices described herein) at a native valve. For the mitral valve, this can be done using a transseptal technique. The delivery catheter is shown as assuming an example of a spiral configuration. Unlike the "hockey stick" configuration, and similar to the configuration discussed in FIGS. 9A-9U, the sheath 20 extends through the FO in a direction parallel to the plane of the native valve annulus (e.g., the mitral plane). In this embodiment, the distal section 75 then exits the sheath 20 and extends for approximately one spiral down to commissure A3P3 of the mitral valve. The distal section 75 can be shape set with a spiral where the distal end of the catheter can initially extend below the native valve annulus plane during deployment. The user can then adjust the height of the distal end, for example, by applying an upward tension on a flex wire integrated into or attached to the catheter, to bring the distal end up to or just above the native valve annulus plane of the patient's heart.

In some embodiments, the distal section 75 can be a full laser cut hypotube (similar to the laser cut catheter described in FIGS. 4-7 above) where the cuts are arranged in a pattern such that, when bent, the distal section forms the spiral configuration. In some embodiments, the spiral configuration of the laser cut hypotube is allowed to be shape set to a spiral that stretches or extends to the native valve annulus plane (e.g., that stretches or extends from the FO to a position that is lower than the mitral plane). Respective gaps between the top teeth and their associated slots (e.g., where the slots are radially wider than the teeth to provide a space for the teeth to move radially when they are in their respective slots) allows the vertical stretching of the catheter to occur. The distal section can be shape set with this vertically stretched configuration. Then when the spiral is in the mitral anatomy, the distal tip of the catheter can be pulled up to position it along or just above the mitral plane, for example, by flexing or tensioning the flex wire in or otherwise attached to the distal section of the catheter as previously discussed. This feature allows the spiral to be adjusted to varying heights to accommodate different patient anatomies.

In another embodiment employing the delivery catheter 74 with the spiral configuration, the distal section 75 may not be constructed as a laser cut hypotube, but can instead be formed as a coated coil. For example, the catheter can be formed by a braided or coiled tube with a low durometer PEBAX with a hardness of about 55D, for example, coated over it. When flexed, the catheter can make a spiral configuration similarly as discussed above. Meanwhile, to control the height of the spiral, a pusher wire can be included that runs along the shaft of the delivery catheter and optionally connects to the distal end of the catheter. The pusher wire has sufficient strength and physical properties to allow the distal end of the catheter to be pushed and/or pulled onto the native valve annulus plane (e.g., the mitral plane). For example, the pusher wire can be a NiTi wire, a steel, or any other suitable wire. In one embodiment, pushing the pusher wire will lower the distal end of the spiral, and pulling back on the pusher wire will raise the distal end of the delivery catheter, in case the distal end goes below the native valve annulus plane (e.g., below the mitral plane).

In another embodiment employing the delivery catheter 74 with the spiral configuration, the distal section may not be laser cut or otherwise cut at all (e.g., similar to the distal section 25'''' shown in FIG. 19). For example, the distal section 75 of the delivery catheter 74 can be formed by a flexible tube catheter constructed with pull rings, pull wires, and/or spines configured to move the delivery catheter 74 into the spiral configuration.

While the delivery catheter 74 having a distal section 75 is described using the embodiments described above, it should be understood that the embodiments described above are only exemplary. The delivery catheter 74 can take any suitable form that is capable of creating the spiral configuration. In addition, the delivery catheter can be constructed with any suitable material that is capable of creating the spiral configuration (e.g., the distal section 75 can take the form of the delivery catheter 114 shown in FIGS. 20A-23).

Figure 11:
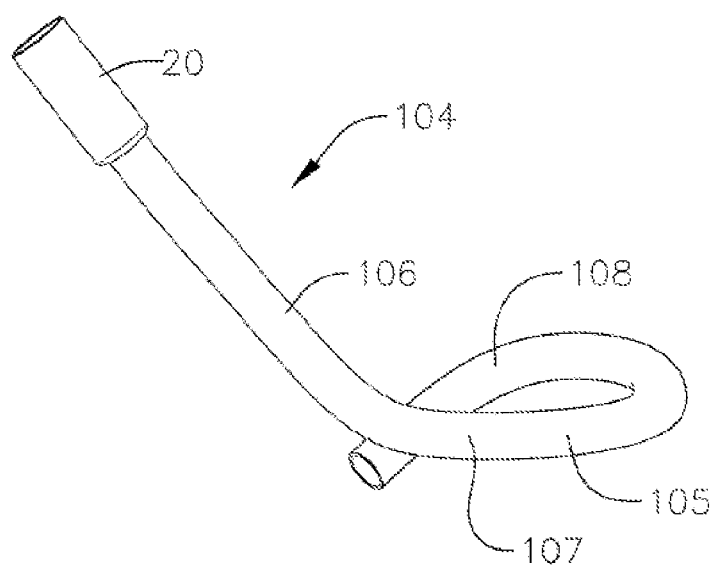
FIG. 11 shows a perspective view of a hybrid configuration of a distal section of a delivery catheter that can be used for implanting an anchoring device at a native valve, which can optionally be used during a transseptal technique.

FIG. 11 shows a perspective view of a hybrid configuration of a distal section 105 of a delivery catheter 104. The delivery catheter 104 combines features from both the "hockey stick" and the spiral configurations discussed above. In the hybrid configuration, similar to the "hockey stick" configuration, the distal section 105 of the delivery catheter 104 first has a shallow curved or bent portion 106 to bend the catheter 104 towards the mitral plane. In an alternative embodiment, the catheter 104 is bent by increasing the proximal flex of the bent portion 106. The shallow curved portion can be followed by a circular or curved planar portion 107 that begins curving, for example, in a counter-clockwise direction as shown. In other embodiments, the delivery catheter 104 can instead bend or curve in a clockwise direction (e.g., as seen in FIG. 8). The planar portion 107 can be substantially parallel to the mitral plane.

Meanwhile, distal to the planar portion 107 is a flexible end portion 108 that can be bent, angled, or otherwise pointed slightly downwards out of the plane in which the planar portion 107 is arranged, to more effectively point the distal opening of the delivery catheter 104 towards or through a commissure or other target. In some embodiments, the flexible end portion 108 can form a downwardly spiraling region of the delivery catheter 104. The flexible end portion 108 can be deflected or displaced from the planar portion 107 by, for example, between about 2 mm and about 10 mm in a vertical direction, such as between about 3 mm and about 9 mm, such as between about 4 mm and about 8 mm, such as between about 5 mm and about 7 mm, such as about 6 mm. In other embodiments, the vertical displacement can be about 2 mm or more, such as about 3 mm or more, such as about 4 mm or more, such as about 5 mm or more, such as about 6 mm or more, such as about 7 mm or more, such as about 8 mm or more, such as about 9 mm or more, such as about 10 mm. Furthermore, in some embodiments, the flexible end portion 108 (i.e., the downward spiraling section) can begin substantially from the curved portion 106, such that there is only a small portion, or even no portion, of the distal section 105 of the delivery catheter 104 that extends in a plane substantially parallel to the mitral plane.

Like the previously described delivery catheters, the distal section 105 of the delivery catheter 104 can be made of or include a laser cut hypotube, a braided or coiled tube catheter, a flexible tube having no cuts, or other flexible tubular construction. In some embodiments, the distal section 105 of the catheter 104 can be coated, for example, with PEBAX. Furthermore, the distal end 105 of the delivery catheter 104 can be actuated or manipulated, for example, via shape setting, pull wires and/or pull rings, spines, and/or utilizing various other ways or features described in the present application.

Meanwhile, while in the above described embodiments, the delivery device is generally or mostly positioned above the native valve annulus plane (e.g., mitral plane), and the anchoring device is extruded from the delivery device while still on the atrial side or just slightly beyond it ((e.g., 1-5 mm or less), and advanced into the ventricle (for example, through a commissure of the native valve), in some other embodiments, at least a portion or a substantial portion of the delivery device itself can also be positioned in the left ventricle. For example, FIG. 12 shows a delivery device for installing an anchoring device 1 at a native mitral valve using a transseptal technique, where much of the distal end of the delivery device itself (e.g., the curved portion or actuatable portion) is also advanced through the native mitral valve and into the left ventricle.

Figure 12:
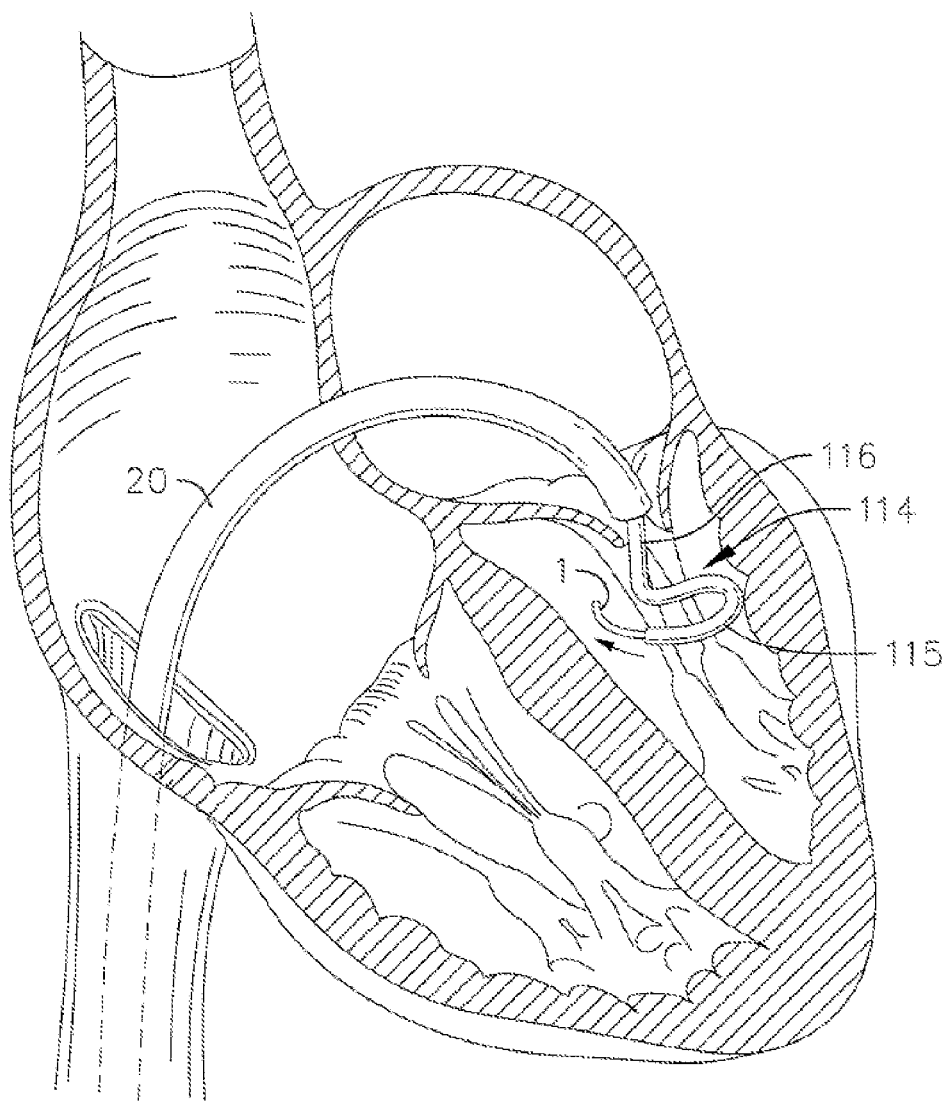
FIG. 12 shows a partial perspective view of an exemplary delivery device that can be used for implanting an anchoring device at a native mitral valve, e.g., using another transseptal technique.

Referring to FIG. 12, the delivery device shown includes an outer guide sheath 20 and a flexible delivery catheter 114 that can be advanced through and out of a distal end of the guide sheath 20. In the embodiment shown, the guide sheath 20 can first be steered, for example as seen in FIG. 12, through an opening that is formed in the interatrial septum (e.g., at the fossa ovalis), and into the left atrium. The guide sheath 20 can then be manipulated to curve or bend downwards towards the native mitral valve annulus, so that the distal opening of the guide sheath 20 points substantially coaxially with a central axis of the mitral annulus. A vertical position of the guide sheath 20 can be such that the distal opening of the guide sheath 20 is substantially aligned with the native mitral annulus, or can be positioned in the left atrium slightly above the native mitral annulus, or, in some embodiments (as shown in FIG. 12), can extend through the native mitral annulus and into the left ventricle.

Once the guide sheath 20 is positioned substantially as shown in FIG. 12, the delivery catheter 114 is then advanced out of the distal opening of the guide sheath 20. In this embodiment, the distal end of the guide sheath 20 is positioned at or slightly above the native mitral annulus, so that the delivery catheter 114 can first be advanced into the left atrium, just above the native mitral annulus. The delivery catheter 114 can initially be advanced out of the distal opening of the guide sheath 20 in an unactuated, substantially straight configuration, and can thereafter be actuated into the bent configuration shown in FIG. 12 after advancement out of the guide sheath 20. In some embodiments, the delivery catheter 114 can be actuated to any other suitable configuration, such as, for example, any configuration described in the present application.

The flexible delivery catheter 114 can include two main deflectable sections or more, e.g., a distal section 115 that is bendable into a curved configuration that is relatively wider and more circular in shape for assisting in shaping the anchoring device 1 when the anchoring device 1 is advanced out of the delivery catheter 114 and delivered to the implant site, and a more proximal section 116 that forms a sharper bent portion, for example, a bend of approximately 90 degrees, to assist in bringing the distal section 115 into a plane that is substantially coplanar with or parallel to the native annulus plane (e.g., the mitral plane). The delivery catheter 114 can take any suitable form, such as, for example, any form described in the present application.

Figure 13:
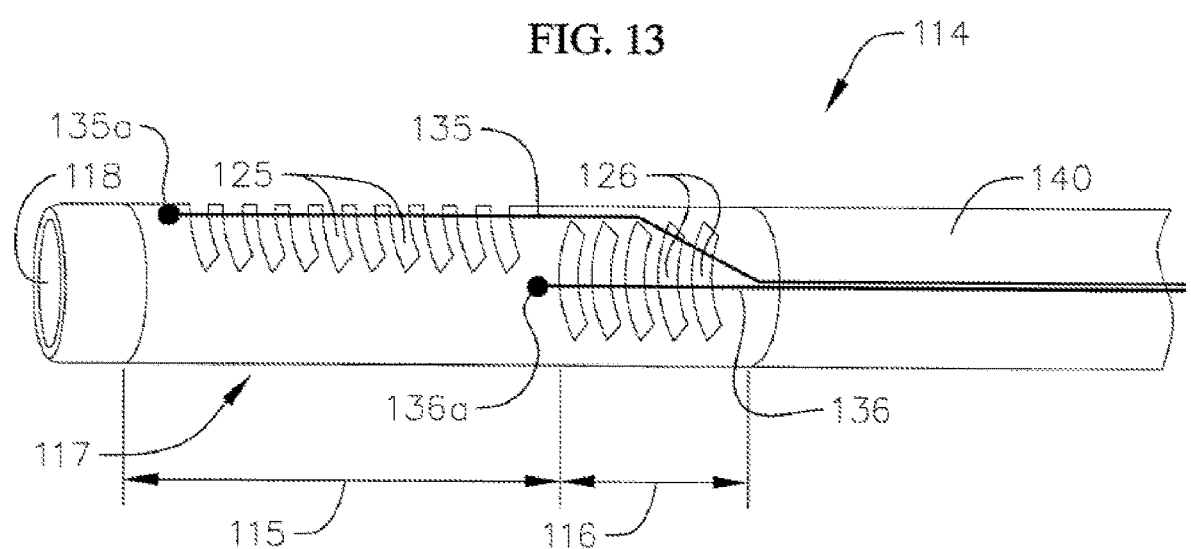
FIG. 13 shows a schematic side view of an exemplary distal section of a delivery catheter with an exemplary two control wire or pull wire system that can be used in various delivery catheters or delivery devices herein.
Figure 14:
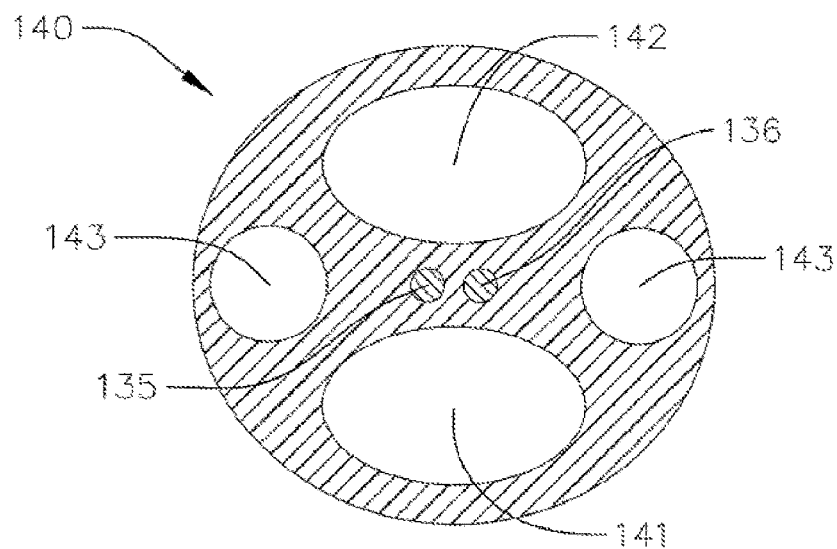
FIG. 14 shows a cross-sectional view of a multi-lumen extrusion portion of the delivery catheter of FIG. 13, the cross-section taken in a plane perpendicular to a longitudinal axis of the delivery catheter.

Referring to FIGS. 13-16, in one exemplary embodiment, a distal region 117 of an exemplary delivery catheter 114 can be constructed of a hypotube having a first series of slots 125 and a second series of slots 126. The delivery catheter can also have a pull wire system (e.g., a two pull wire system that includes a first pull wire 135 and a second pull wire 136). FIG. 13 shows a schematic side view of a distal section 117 of an exemplary embodiment of a delivery catheter 114. FIG. 14 shows a cross-sectional view of a multi-lumen extrusion portion of the delivery catheter 114, the cross-section taken in a plane perpendicular to a longitudinal axis of the delivery catheter, and FIGS. 15 and 16 respectively show schematic perspective views of the delivery catheter 114 of FIG. 13 in partial and fully actuated states. Other delivery catheters that are deployed and used in different manners, for example, as shown in any of the embodiments discussed above, can also be constructed in a similar two pull wire system.

In one embodiment, the delivery catheter 114 has a distal region 117 including two flexible sections 115, 116. A first series of slots 125 can be arranged (e.g., linearly arranged or otherwise) along a first side of the distal region 117, corresponding and providing flexibility to the first flexible section 115, so that the first flexible section 115 can form a generally circular configuration (e.g., which can be similar to that shown in FIG. 12) when the delivery catheter is actuated. A second series of slots 126 can be arranged linearly along a second side of the distal region 117, corresponding and providing flexibility to the second flexible section 116, so that the second flexible section 116 can form the sharper bend shown in FIG. 12 when the delivery catheter 114 is actuated. The slots 125, 126 can be laser cut or formed similarly as discussed in previous embodiments, or can otherwise be formed in various other manners, so long as the slots 125, 126 contribute to the desired shaping of the delivery catheter 114 upon actuation. The second series of slots 126 is positioned slightly proximal to the first series of slots 125 corresponding to the bending positions of the sections 115, 116, and can be offset in a circumferential direction, for example, by approximately 90 degrees around the distal region 117, in order to allow for two orthogonal bends in the region, where the respective radii of curvature and directions of articulation of the sections 115, 116 can be different from one another. In some embodiments, the section 115, 116 can be offset in a circumferential direction by, for example, between about 65 degrees and about 115 degrees, such as between about 75 degrees and about 105 degrees, such as between about 80 degrees and about 100 degrees, such as between about 85 degrees and about 95 degrees.

In certain embodiments, each of the sections 115, 116 can have an associated pull wire 135, 136, for respectively controlling the bending of the sections 115, 116. The pull wire 135 can extend distally past the slots 125 and can be attached to the distal region 117, for example, via welding or other attachment means at connection point 135a and/or a pull ring. Similarly, the pull wire 136 can extend distally past the slots 126 and can be welded or otherwise attached to the distal region 117 at connection point 136a and/or a pull ring.

Meanwhile, on a proximal side of the distal region 117, the delivery catheter 114 can include a proximal section 140 that can be formed as a braided multi-lumen tube extrusion. As can be seen in the cross-section of FIG. 14, the proximal section 140 of the delivery catheter 114 can have one or more central lumens through which the pull wires 135, 136 extend to reach the distal region 117. The pull wires 135, 136 can be arranged to extend side-by-side through a central region of proximal section 140, and can then exit distally from the proximal section 140 and attached to the side walls of the distal region 117, as previously described. The central positioning of the pull wires 135, 136 through the proximal section 140 provides for an anti-whipping or anti-bending effect through the delivery catheter 114 when the pull wires 135, 136 are used, allowing the delivery catheter 114 to maintain full torqueability. However, in some embodiments, the pull wires are not centrally positioned, but run along the side walls or outer walls from end to end.

In addition, the proximal section 140 can have a main lumen 141. Where the pull wires are not centered, the main lumen can be centered. Optionally, main lumen 141 can be offset from the center of the extrusion, e.g., when the pull wires are centered. The main lumen 141 is sufficiently sized for an anchoring device to pass and be delivered therethrough. The main lumen 141 can have, for example, an ovoid cross-section, a circular cross-section, or can have a cross-section with any other appropriate shape, so long as the anchoring device 1 can be effectively advanced through it. In addition to the main lumen, a number of optional parallel dummy lumens can also be formed in and extend longitudinally through the proximal section 140, e.g., in order to affect a symmetric moment of inertia about the pull wires through the proximal section 140. In the embodiment shown, a first dummy lumen 142 is optionally positioned diametrically opposite the main delivery lumen 141 and is formed to be substantially the same shape as the main lumen 141 (e.g., ovoid in the illustrated embodiment). In addition, two more optional dummy lumens 143 are positioned diametrically opposite one another and circumferentially between the lumens 141 and 142. The additional dummy lumens 143 are illustrated to be slightly smaller than the lumens 141, 142, and have a more circular shape. In practice, the size and shape of the dummy lumens 143 can otherwise vary, and will generally be selected based on the respective sizes of the lumens 141, 142, and the amount of space remaining in the extrusion. In addition, the main lumen 141 and the first dummy lumen 142 can also have variable sizes and shapes, depending on the particular application. Furthermore, in some other embodiments, more or less than four total lumens can be formed in the proximal section 140, to affect a desired symmetry and moment of inertia, and to even out the stiffness, about the pull wires that run through the center axis of the proximal section 140.

Figure 15:
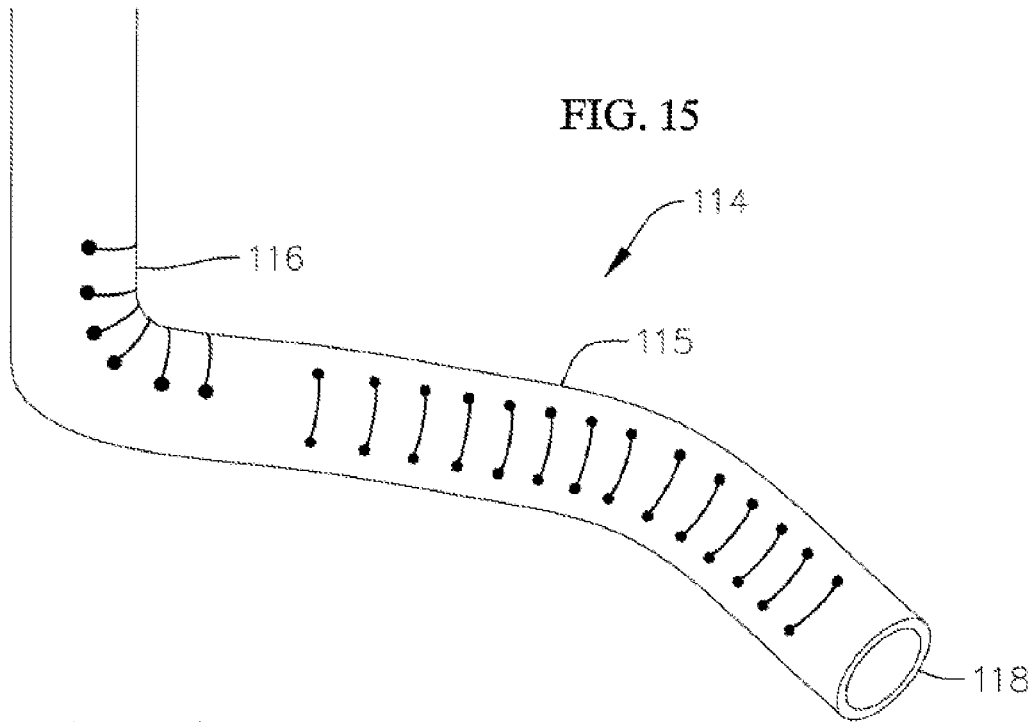
FIG. 15 shows a schematic perspective view of the delivery catheter of FIGS. 13-14 in a partially actuated state.
Figure 16:
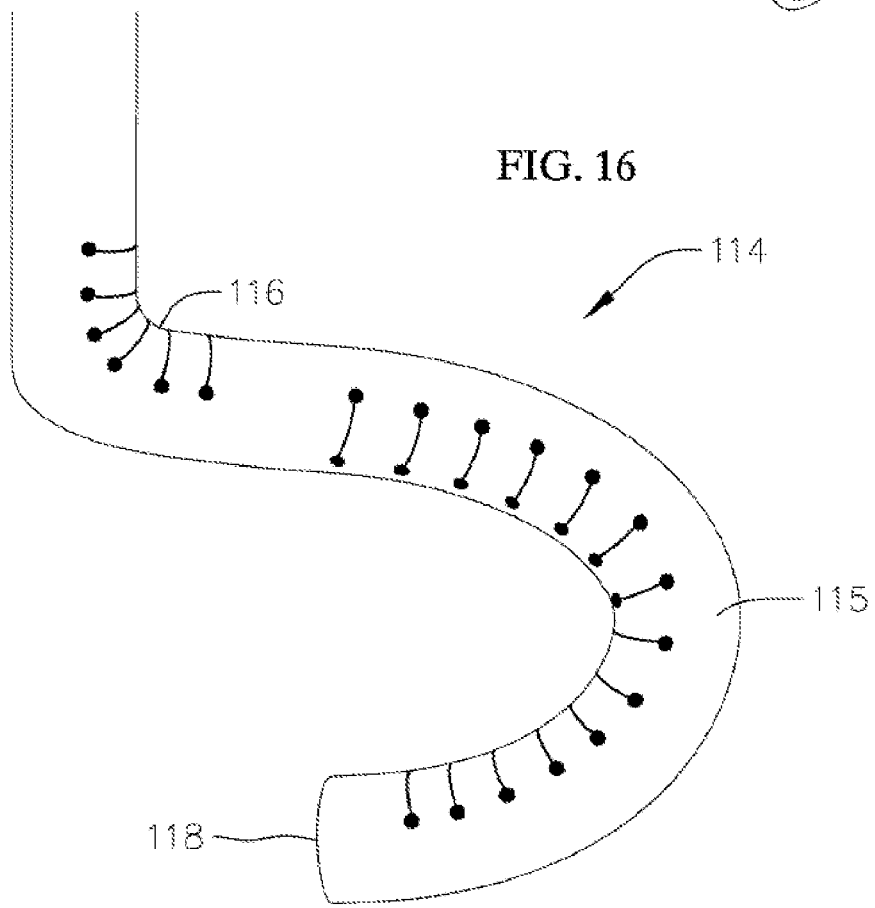
FIG. 16 shows a schematic perspective view of the delivery catheter of FIGS. 13-15 in a fully actuated state.

Referring back to FIGS. 2B, 9A-9N, and 12, in practice, once the guide sheath 20 is arranged or positioned as desired (e.g., as shown or described elsewhere herein, for example, crossing the septum in a mitral procedure, distal regions of the delivery catheter (e.g., distal region 117 or any of the other distal regions described herein), and in some embodiments, a portion of a proximal section (e.g., proximal section 140), are advanced out of the distal opening of the guide sheath 20. The portions of the delivery catheter (e.g., catheter 114) that extend out of the guide sheath 20 can be positioned in the left atrium before the delivery catheter is adjusted to its actuated configuration or final actuated configuration. In some cases, part of the delivery catheter can also extend (e.g., as in FIG. 12 or with just the tip extending slightly, such as 1-5 mm or less) into the left ventricle through the native mitral valve before the delivery catheter is adjusted to its actuated configuration or final actuated configuration. The pull wires 135, 136 can then be tensioned in order to actuate the distal region 117 and to gain articulation of the two bends, e.g., in sections 115, 116, at the distal portions of the delivery catheter 114. For example, in one sequence, as shown in FIG. 15, the second pull wire 136 can first be tensioned in order to bend section 116 and bring the portions of the delivery catheter 114 distal to section 116 substantially planar and/or parallel to the native annulus. Then, as shown in FIG. 16, the first pull wire 135 can then be tensioned, to bend section 115 to its rounded or curved actuated state, such that the curvature of section 115 is substantially planar to and/or parallel with the native valve annulus (e.g., with the mitral plane). In other embodiments, the pull wires 135, 136 can be tensioned partially or fully in different amounts and/or orders to properly and safely navigate around the patient's anatomy during actuation. For example, section 115 can be actuated and curved to form a circular or curved planar portion (e.g., similar to planar portion 67) before actuating or curving section 116 to lower and/or properly angle the curved planar portion or section 115 (e.g., as described with respect to FIG. 9). After these actuating steps, in one embodiment, the distal region 117 of the delivery catheter 114 can be fully or mostly positioned in the left atrium, or on the atrial side of the native valve.

In some circumstances, actuation of the curved regions of the delivery catheter may not alone be enough to properly position the distal tip at or near the commissure in a desired position for delivery, and torqueing or rotating the delivery device or a portion thereof (e.g., rotating the delivery catheter and/or guide sheath) can be used to angle the delivery catheter and a tip of the delivery catheter as desired. For example, after the distal region 117 of the delivery catheter 114 is fully actuated or curved as desired (e.g., as described above), the assembly can be torqued and rotated to cause the tip of the delivery catheter 114 to be angled or aligned at or into a commissure of the native valve, for example, at commissure A3P3 of the mitral valve. The delivery catheter 114 can then be further torqued and rotated so that the distal tip of the delivery catheter 114 passes through the commissure and into the left ventricle. Optionally, further rotation and/or actuation of the delivery catheter 114 can then facilitate circumferential advancement of the distal tip of the delivery catheter 114 in the left ventricle, to be looped or positioned around an outside of the mitral anatomy, for example, chordae tendineae, papillary muscles, and/or other features in the left ventricle. The design of the proximal section 140 and the central arrangement of the pull wires 135, 136 helps provide for an anti-whipping or anti-bending effect through the delivery catheter 114 when the pull wires 135, 136 are operated, allows for maintaining of full torqueability of the delivery catheter 114 through the transseptal bend, and facilitates the actuated shape of the distal region 117 to be held and maintained more effectively during this rotation step.

Referring to FIG. 12, if a user elects to move the distal region of the catheter into a ventricle (e.g., left or right ventricle), movement of the delivery catheter 114 around the anatomy in the ventricle can serve to gather or capture the corralled anatomy within the bend of the distal region 117. In some embodiments, after the distal region 117 of the delivery catheter 114 is moved to a desired position around the chordae and other features in the ventricle, the first pull wire 135 can still be tensioned further, in order to reduce the radius of curvature of the rounded section 115, in order to cinch and gather the chordae and other native anatomy passing through the center of the rounded section 115 even further towards the center of the native annulus. Such radial cinching or gathering of the native anatomy in the ventricle can help facilitate an even more robust delivery of the anchoring device 1 later, for example, by making it easier for the anchoring device 1 to be advanced around the gathered chordae and other features.

After the delivery catheter 114 has been satisfactorily positioned around the chordae and other desired anatomy in the left ventricle, the anchoring device 1 can be advanced out of the distal opening of the delivery catheter 114. The curved shape of the rounded section 115 can facilitate smoother and easier extrusion of the anchoring device 1 from the delivery catheter 114, since the curvature of the rounded section 115 can be formed to be substantially similar to the final curvature of the anchoring device 1. Furthermore, the initial looping of the distal region 117 around at least part of the desired mitral anatomy in the left ventricle can facilitate easier delivery of the anchoring device 1 outside and around the same anatomy that has already been corralled. Once the ventricular portion of the anchoring device 1 has been advanced to a desired position in the left ventricle, the atrial portion of the anchoring device 1 can be released from the delivery catheter 114 in a similar manner as one of the various ways discussed above, for example, by backwards axial translation of the delivery catheter 114. Such translation of the delivery catheter 114 can also help retract the delivery catheter 114 itself out of the left ventricle and back into the left atrium. Then, after the anchoring device 1 has been fully delivered and moved to a desired position, the tensioning in the pull wires 135, 136 can be released, and the delivery catheter 114 can be straightened and retracted back through the guide sheath 20. Thereafter, a prosthesis (e.g., a THV or other prosthetic valve) can be advanced to and expanded in the anchoring device 1, similarly as previously discussed.

FIGS. 20A-20E, 22 and 23 illustrate an exemplary embodiment of a delivery catheter that can operate in the same or similar manner as the delivery catheters 64, 114 described above. Any of the components, mechanisms, functions, elements, etc. (e.g., the steering or actuation mechanism or pull wire system, pull wires, rings, spines, etc.) of this embodiment can be incorporated into other delivery catheters (and even guide sheaths) described herein. In the example illustrated by FIGS. 20A-20E, 22, and 23, the distal region 117 of the delivery catheter 114 can be constructed of flexible tube 2030 (e.g., which can be the same as or similar to the flexible tube 25'''' shown in FIG. 19 or other tubes described herein). The delivery catheter has a steering/actuation mechanism or pull wire system that can be used to actuate and curve the distal region of the catheter. A steering/actuation mechanism or pull wire system herein can have one or more pull wires (e.g., 1-6 or more pull wires), one or more rings or pull rings (e.g., 1-7 or more rings), one or more spines, and/or other components.

Figure 21A:
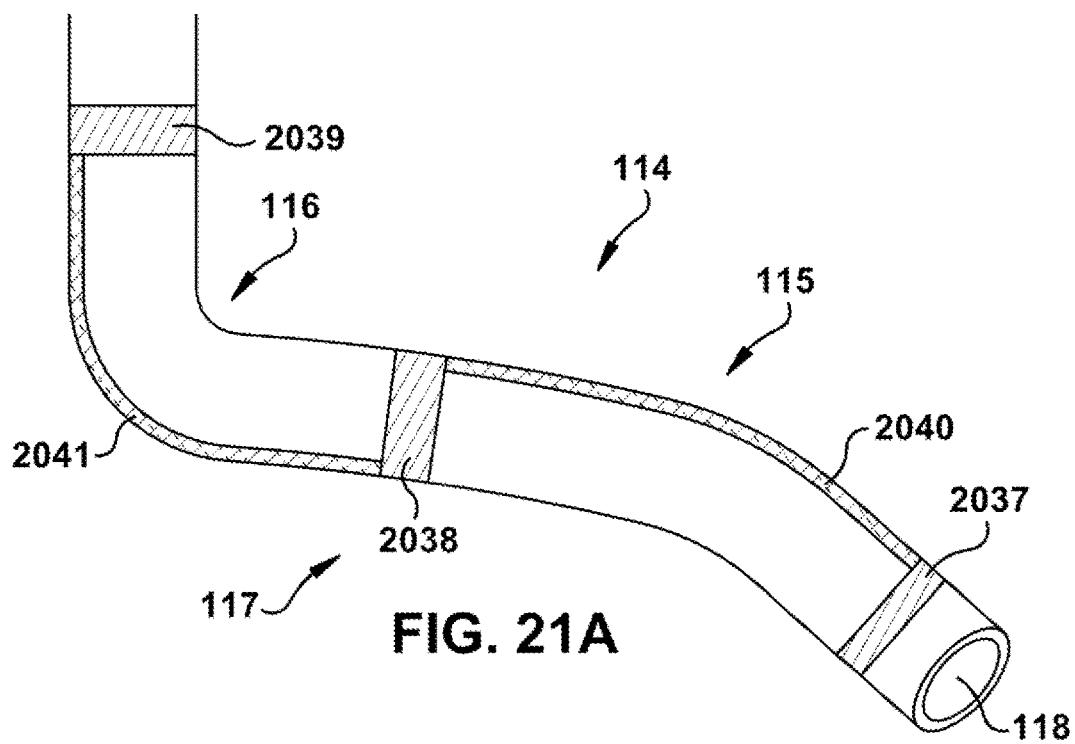
FIG. 21A shows a schematic perspective view of a distal section of the delivery catheter of FIGS. 20A-20E in a partially actuated state.
Figure 21B:
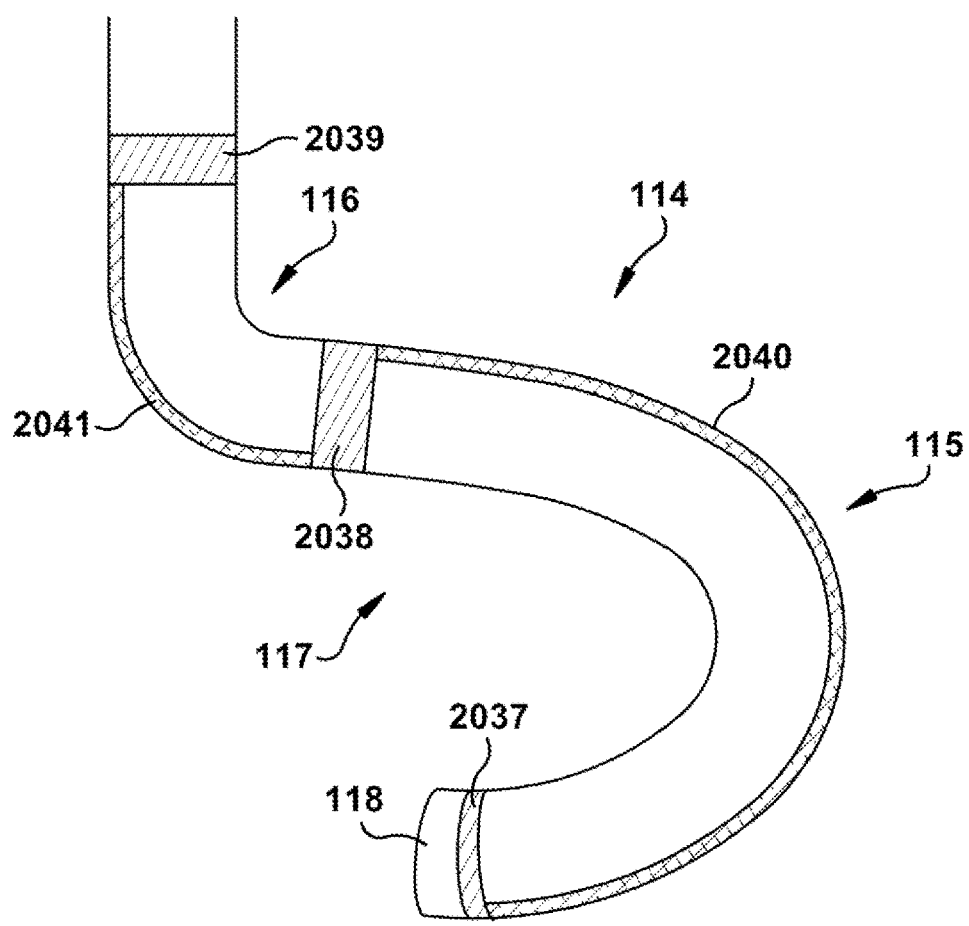
FIG. 21 B shows a schematic perspective view of the distal section of the delivery catheter of FIGS. 20A-20E in a more actuated state.
Figure 23:
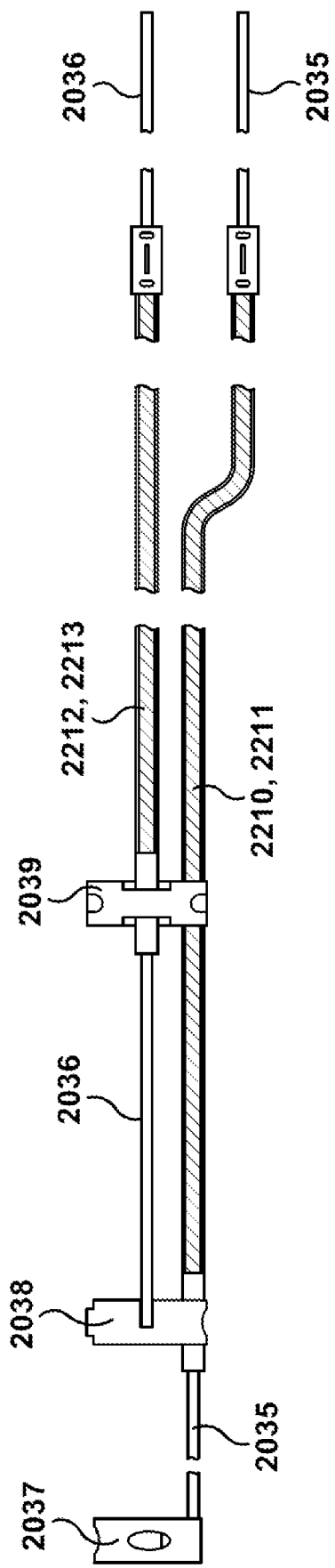
FIG. 23 shows a schematic view of an exemplary two pull wire system for the delivery catheter shown in FIGS. 20A-20E.

In the illustrated embodiment, the delivery catheter has a two pull wire system that includes a first pull wire 2035, a second pull wire 2036, three rings or pull rings (i.e., a first ring 2037, a second ring 2038, a third ring 2039), a first spine 2040, and a second spine 2041. FIG. 20A shows an end view of a distal section 117 of the delivery catheter 114. FIG. 20C is a sectional view of the delivery catheter 114 of FIG. 20A taken along the plane indicated by lines C-C. FIG. 20B is a sectional view of the delivery catheter 114 taken along the plane indicated by lines B-B. FIG. 20D shows a cross sectional view of the delivery catheter 114 taken along the plane indicated by lines D-D in FIG. 20A. FIG. 20E is taken along the plane indicated by a cross-sectional view of the delivery catheter 114 taken along the plane indicated by lines E-E in FIG. 20A. FIGS. 21A and 21B are schematic perspective views of the delivery catheter 114 in partially and fully actuated states, respectively, similar to the views of FIGS. 15 and 16. FIG. 22A is a partial view of the delivery catheter 114. FIGS. 22B-22D show cross-sectional views of the delivery catheter taken along the planes indicated by lines B-B, C-C, and D-D, respectively, in FIG. 22A. FIG. 23 is a side view of the two-pull wire system for the delivery catheter 114. Other delivery catheters or sheaths that are deployed and used in different manners, for example, as shown in any of the embodiments discussed above, can also be constructed with a similar two pull wire system. While the illustrated embodiments show the delivery catheter 114 having rings 2037, 2038, 2039 and spines 2040, 2041, it should be understood that the delivery catheter 114 can be constructed having any number of rings and/or spines, or without any rings or spines.

In the illustrated embodiment, the delivery catheter 114 has a distal region 117 including the two flexible sections 115, 116. Referring to FIG. 20C, the first flexible section 115 extends between the first ring 2037 and the second ring 2038. A first pull wire 2035 is attached to the first ring 2037 at connection point A, and actuation of the first pull wire 2035 causes the first flexible section 115 to form the generally circular configuration shown in FIGS. 11 and 12. Referring to FIGS. 20C and 20D and 22A and 22B, an optional spine 2040 is connected between the first ring 2037 and the second ring 2038. The spine 2040 is made of a stiffer material than the flexible tube 2030 and, therefore, is configured to restrict the movement, such as compression, of between the rings 2037, 2038 when the first pull wire 2035 is actuated. The spine 2040 can be made of, for example, stainless steel, plastic, or any other suitable material that is stiffer than the flexible tube. The flexible tube 2030 can be made out of, for example, nitinol, steel, and/or plastic, or any other suitable material or combination of materials that allow the delivery catheter 114 to be moved to a flexed configuration (e.g., the flexed configuration shown in FIG. 12). In certain embodiments, the ratio of Shore D hardness for the spine 2040 to Shore D hardness of the flexible tube 2030 is between about 3:1. In certain embodiments the, ratio of shore D hardness of the spine 2040 to the flexible tube 2030 is between about 1.5:1 and about 5:1, such as between about 2:1 and about 4:1, such as between about 2.5:1 and about 3.5:1. In alternative embodiments, the ratio of Shore D hardness of the spine 2040 to the flexible tube 2030 is greater than 5:1 or less than 1.5:1.

In the illustrated embodiment, the spine 2040 is disposed substantially opposite the first pull wire 2035 such that a center of the spine 2040 is circumferentially offset from the first pull wire 2035 by approximately 180 degrees. A center of the spine 2040 can be circumferentially offset from the first pull wire 2035 by between about 70 degrees and about 110 degrees, such as between about 80 degrees and about 100 degrees, such as between about 85 degrees and about 95 degrees. Referring to FIG. 22B, the width of the spine 2040 (defined by the angle θ) can be any suitable width that allows the delivery catheter 114 to move to the bent configuration shown in FIGS. 11 and 12. In certain embodiments, the angle between the edges 2201, 2203 of the spine 2040 can between about 45 degrees and about 135 degrees, such as between about 60 degrees and about 120 degrees, such as between about 75 degrees and about 105 degrees such as between about 85 degrees and 95 degrees, such as about 90 degrees. A larger angle θ allows for the spine 2040 to have more control in restricting the movement of the rings 2037, 2038 as compared to a smaller angle θ. The spine 2041 can be made of, for example, nitinol, steel, and/or plastic, or any other suitable material or combination of materials.

Referring to FIG. 20B, the second flexible section 116 extends between the second ring 2038 and the third ring 2039. The second pull wire 2036 is attached to the second ring 2038 at connection point B, and actuation of the second pull wire 2036 causes the second flexible section 116 to form the sharper bend shown in FIGS. 11 and 12. Referring to FIGS. 20B and 20E and 22A and 22C, an optional spine 2041 is connected between the second ring 2038 and the third ring 2039. The spine 2041 is made of a stiffer material than the flexible tube 2030 and, therefore, is configured to restrict the movement of between the rings 2038, 2039 when the second pull wire 2036 is actuated. The spine 2041 can be made of, for example, stainless steel, plastic, or any other suitable material that is stiffer than the flexible tube. The flexible tube 2030 can be made out of, for example, nitinol, steel, and/or plastic, or any other suitable material or combination of materials that allow the delivery catheter 114 to be moved to a flexed configuration (e.g., the flexed configuration shown in FIG. 12). In certain embodiments, the ratio of Shore D hardness for the spine 2041 to Shore D hardness of the flexible tube 2030 is between about 3:1. In certain embodiments the, ratio of shore D hardness of the spine 2041 to the flexible tube 2030 is between about 1.5:1 and about 5:1, such as between about 2:1 and about 4:1, such as between about 2.5:1 and about 3.5:1. In alternative embodiments, the ratio of Shore D hardness of the spine 2041 to the flexible tube 2030 is greater than 5:1 or less than 1.5:1.

In the illustrated embodiment, the spine 2041 is disposed substantially opposite the second pull wire 2036 such that a center of the spine 2041 is circumferentially offset from the second pull wire 2036 by approximately 180 degrees. A center of the spine 2041 can be circumferentially offset from the second pull wire 2036 by between about 70 degrees and about 110 degrees, such as between about 80 degrees and about 100 degrees, such as between about 85 degrees and about 95 degrees. Referring to FIG. 22C, the width of the spine 2041 (defined by the angle β) can be any suitable width that allows the delivery catheter 114 to move to the bent configuration shown in FIG. 12. In certain embodiments, the angle β between the edges 2205, 2207 of the spine 2041 can between about 45 degrees and about 135 degrees, such as between about 60 degrees and about 120 degrees, such as between about 75 degrees and about 105 degrees such as between about 85 degrees and 95 degrees, such as about 90 degrees. A larger angle β allows for the spine 2040 to have more control (i.e. add more stiffness) in restricting the movement of the rings 2037, 2038 as compared to a smaller angle β.

Referring to FIGS. 20D and 20E, the delivery catheter 114 includes a lumen 2032 that is sufficiently sized for delivering an anchoring device 1 therethrough, and the lumen 2032 remains sufficiently sized for delivering the anchoring device 1 when the first pull wire 2035 and the second pull wire 2036 are actuated to move the delivery catheter 114 to the bent configuration shown in FIG. 12. The lumen 2032 can have, for example, an ovoid cross-section, a circular cross-section, or can have a cross-section with any other appropriate shape, so long as the anchoring device 1 can be effectively advanced through it.

The connection point B for attaching the second pull wire 2036 to the second ring 2038 is positioned proximal to the connection point A for attaching the first pull wire 2035 to the first ring 2037 and can be offset in a circumferential direction, for example, by approximately 90 degrees around the distal region 117. A 90 degree offset allows for two orthogonal bends in the region, where the respective radii of curvature and directions of articulation of the sections 115, 116 can be different from one another and independent from one another. In some embodiments, the section 115, 116 can be offset in a circumferential direction by, for example, between about 65 degrees and about 115 degrees, such as between about 75 degrees and about 105 degrees, such as between about 80 degrees and about 100 degrees, such as between about 85 degrees and about 95 degrees. Referring to FIGS. 20C and 20E, in certain embodiments, the wires 2035, 2036 run along a length L of the delivery catheter 114 such that the wires are substantially parallel to an axis X that extends through a center of the delivery catheter. In this embodiment, the wires 2035, 2036 are offset in a circumferential direction such that an angle α between the wires 2035, 2036 is between about 65 degrees and about 115 degrees, such as between about 75 degrees and about 105 degrees, such as between about 80 degrees and about 100 degrees, such as between about 85 degrees and about 95 degrees, such as about 90 degrees.

Referring to FIGS. 9A-9U and 20A-23, in practice, once the guide sheath 20 is arranged approximate the native valve annulus (e.g., the mitral annulus or tricuspid annulus), for example, at the position shown, distal regions of the delivery catheter 114, including distal region 117 (and in some embodiments, a portion of proximal section 2034) are advanced out of the distal opening of the guide sheath 20. Here, the portions of the delivery catheter 114 that extend out of the guide sheath 20 can be positioned in an atrium (e.g., left or right atrium), while in some cases, part of the delivery catheter 114 can also extend slightly (e.g., 1-5 mm or less) into a ventricle (e.g., left or right ventricle) through the native valve (e.g., native mitral valve) or a commissure of the native valve before the delivery catheter 114 is adjusted to its actuated configuration or, if partially actuated previously, to its full or final actuated configuration. The pull wires 2035, 2036 can then be tensioned in order to actuate the distal region 117 and to gain articulation of the two bends in sections 115, 116 at the distal portions of the delivery catheter 114. For example, in one sequence, as shown in FIG. 21A, the second pull wire 2036 can first be tensioned in order to bend section 116 and bring the portions of the delivery catheter 114 distal to section 116 substantially planar to the native annulus (e.g., native mitral annulus). Then, as shown in FIG. 21B, the first pull wire 2035 can then be tensioned, to bend section 115 to its rounded or curved actuated state, such that the curvature of section 115 is substantially planar to or parallel with a plane of the native valve annulus (e.g., the mitral plane). In other embodiments, the pull wires 2035, 2036 can be tensioned partially or fully in different amounts and/or orders to properly and safely navigate around or relative to the patient's anatomy during actuation. For example, the pull wires 2035, 2036 can be tensioned to move the delivery catheter 114 in the same manner that the delivery catheter 64 moved in FIGS. 9A-9U. Actuation of the pull wires or pull wire system can be used in combination with torqueing or rotating the delivery device or a portion there (e.g., the delivery catheter or sheath) to direct the distal region and distal tip of the catheter to a desired position and/or orientation.

For example, after the distal region 117 of the delivery catheter 114 is fully actuated or actuated to a desired configuration (as shown in FIG. 21B), the assembly can then be torqued and rotated so that the tip of the delivery catheter 114 is aligned at a commissure of the native valve (e.g., of the native mitral valve, for example, at commissure A3P3). The delivery catheter 114 can be torqued and rotated so that the distal tip of the delivery catheter 114 is directed toward and/or directed into the commissure. Further rotation of the delivery catheter 114 can then facilitate circumferential advancement of the distal tip of the delivery catheter 114 toward and/or into the commissure, and/or to change direction from a downward direction to a more even or parallel (or less downward) direction (e.g., after a first end of the anchoring device has been pushed or extruded out of the delivery catheter) so the end of the anchoring device does not come up undesirably after insertion and hit or push against the underside of the valve annulus, such that the anchoring device 1 can be looped or positioned around an outside of the native anatomy (e.g., outside of the native mitral anatomy), for example, chordae tendineae, papillary muscles, and/or other features in the ventricle.

Referring to FIGS. 22A-22D and 23, in certain embodiments, the delivery catheter 114 includes a first conduit 2210 (e.g., a tube, sleeve, etc.) for housing the first pull wire 2035 a second conduit 2212 for housing the second pull wire 2036. In the illustrated embodiment, the conduits 2210, 2212 are defined, at least in part, by a liner 2215 and an inner surface 2216 of the flexible tube 2030. In some embodiments, the conduits 2210, 2212 can take any other suitable form. In some embodiments, conduits are not used to house the pull wires 2035, 2036. The design of the proximal section 140 and the arrangement of the pull wires 2035, 2036 provide for an anti-whipping or anti-bending effect through the delivery catheter 114 when the pull wires 135, 136 are operated. This can allow for maintaining full torqueability of the delivery catheter 114 through the transseptal bend. This can also facilitate the actuated shape of the distal region 117 to be held and maintained more effectively during torqueing or rotation during delivery. In some embodiments, the delivery catheter 114 includes a first coil sleeve 2211 that extends around the first pull wire 2035 until it reaches the first flexing section 115 and a second coil sleeve 2213 that extends around the second pull wire 2036 until it reaches the second flexing section 116. The coil sleeves 2211, 2213 are configured to provide for the anti-whipping or anti-bending effect and for maintaining the full torqueability of the delivery catheter 114.

Deployment of the delivery device 1 from the delivery catheter 114 (and, optionally, movement of the delivery catheter 114 around the anatomy in the ventricle) serves to gather or capture the corralled anatomy within the anchoring device 1. In some embodiments, the distal region 117 of the delivery catheter 114 is moved to a desired position around the chordae and other features in the left ventricle, and the first pull wire 135 is tensioned in order to reduce the radius of curvature of the rounded section 115, and in order to cinch and gather the chordae and other mitral anatomy passing through the center of the rounded section 115 even further towards the center of the native annulus. Such radial cinching or gathering of the mitral anatomy in the left ventricle can help facilitate an even more robust delivery of the anchoring device 1 later, for example, by making it easier for the anchoring device 1 to be advanced around the gathered chordae and other features.

When the delivery catheter is used in the ventricle to corral native anatomy, after the delivery catheter 114 has been satisfactorily positioned around the chordae and other desired anatomy in the left ventricle, the anchoring device 1 can be advanced out of the distal opening of the delivery catheter 114. The curved shape of the rounded section 115 can facilitate smoother and easier extrusion of the anchoring device 1 from the delivery catheter 114, since the curvature of the rounded section 115 can be formed to be substantially similar to the final curvature of the anchoring device 1. Furthermore, the initial looping of the distal region 117 around at least part of the desired mitral anatomy in the left ventricle facilitates easier delivery of the anchoring device 1 outside and around the same anatomy that has already been corralled. Once the ventricular portion of the anchoring device 1 has been advanced to a desired position in the left ventricle, the atrial portion of the anchoring device 1 can be released from the delivery catheter 114 in a similar manner as one of the various ways discussed above, for example, by backwards axial translation of the delivery catheter 114. Such translation of the delivery catheter 114 can also help retract the delivery catheter 114 itself out of the left ventricle and back into the left atrium. Then, after the anchoring device 1 has been fully delivered and moved to a desired position, the tensioning in the pull wires 2035, 2036 can be released, and the delivery catheter 114 can be straightened and retracted back through the guide sheath 20. Thereafter, a THV or other prosthetic valve can be advanced to and expanded in the anchoring device 1, similarly as previously discussed.

In some embodiments (e.g., any of the embodiments for a delivery catheters described in the present application), an atraumatic tip 118 can also be formed at the end of the distal region 117, to prevent or reduce potential damage to the guide sheath 20 or the patient's anatomy when the delivery catheter 114 is advanced and maneuvered to its desired position and orientation. The atraumatic tip 118 can be an extension of the distal region 117 that is formed in a rounded or otherwise atraumatic shape, or can, for example, be an added layer that is formed from a different material from the distal region 117, for example, an additional braided layer and/or be made from a lower durometer material.

Optionally, the anchoring or docking device can also include a low-friction sleeve, e.g., a PTFE sleeve, that fits around all or a portion (e.g., the leading and/or functional turns) of the anchoring or docking device. For example, the low-friction sleeve can include a lumen in which the anchoring device (or a portion thereof) fits. The low-friction sleeve can make it easier to slide and/or rotate the anchoring device into position as it exits the delivery catheter with less-friction and being less likely to cause abrasions or damage to the native tissue than the surface of the anchoring device. The low-friction sleeve can be removable (e.g., by pulling proximally on the sleeve while holding a pusher and the anchoring device in place) after the anchoring device is in position in the native valve, e.g., to expose the surface of the anchoring device, which can be or include portions configured (porous, braided, large surface area, etc.) to promote tissue ingrowth.

The delivery catheter configurations described herein provide example embodiments that allow for accurate positioning and deployment of an anchoring device. However, in some instances, retrieval or partial retrieval of the anchoring device can still be necessary at any stage during or after deployment of the anchoring device in order, for example, to reposition the anchoring device at the native valve, or to remove the anchoring device from the implant site. The below embodiments describe various locks or lock-release mechanisms that can be used for attaching and/or detaching an anchoring or docking device from a deployment pusher that pushes the anchoring device out of the delivery catheter. Other locks or locking mechanisms are also possible, e.g., as described in U.S. Provisional Patent Application Ser. No. 62/560,962, filed on Sep. 20, 2017 incorporated by reference herein. The anchoring device can be connected at its proximal side to a pusher or other mechanism that can push, pull, and easily detach from the anchoring device.

In previous examples, a suture or line of the pusher or pusher tool passes through an opening or eyelet in the end of the anchoring device to hold the anchoring device and allow retrievability and release of the anchoring device. FIGS. 17A-17C show perspective views of a proximal end 82 of an exemplary anchoring device 81 and a ball locker or locking mechanism 84. The anchoring device 81 can be similar to the anchoring device embodiments described above, with the addition of the modified proximal end 82, as seen in FIG. 17A. The proximal end 82 of the anchoring device 81 has an elongate tube structure 83 that forms a locking tube, and the ball locking mechanism 84 includes a pusher 85 (which can be the same as or similar to other pushers herein mutatis mutandis) and a pull wire 86 that interact with the locking tube 83. The pusher 85 includes a flexible tube 87 which, although shown cut away in FIGS. 17A-17C, can be long enough to extend through the delivery catheter during deployment of the anchoring device 81. The pull wire 86 extends through the pusher 85 and can protrude through a distal end of the pusher 85 with a length that allows the pull wire 86 to also go through the locking tube 83 of the anchoring device 81. The pusher 85 has a distal tip 88 and a short wire 89 connected to and/or extending from the pusher tip 88. A distal end of the short wire 89 includes a spherical ball 90.

The locking tube 83 at the proximal end 82 of the anchoring device 81 is sized to receive the spherical ball 90 of the short wire 89 therethrough, as shown in FIG. 17B. The locking tube 83 is a short tube that can be welded to or otherwise affixed to a proximal end of the anchoring device 81 (as oriented during delivery). The internal diameter of the locking tube 83 is slightly greater than the external diameter of the spherical ball 90, so that the ball 90 can pass therethrough. The lock or locking mechanism is based on the relative diameters of the inner diameter of the locking tube 83, the diameter of the ball 90, and the diameters of the other portions of the short wire 89 and of the pull wire 86.

After the ball 90 passes through and out of the distal end of the locking tube 83, locking can be achieved by preventing the ball 90 from passing back through and being released from the locking tube 83. This can be accomplished by also inserting the pull wire 86 into the locking tube 83. When both the thinner portion of the short wire 89 and the pull wire 86 are threaded and positioned in the locking tube 83, as shown in FIGS. 17C-17D, the ball 90 is blocked from passing back through the locking tube 83, and thereby locking the anchoring device 81 to the pusher 85. As best seen in FIG. 17D, when the pull wire 86 is in the locking tube 83, the pull wire 86 blocks the short wire 89 from moving to a more central position in the bore of the locking tube 83, preventing the ball 90 from aligning with and retracting back out through the locking tube 83. Therefore, the ball 90 abuts against a distal end of the locking tube 83 when the pusher 85 is pulled proximally therefrom. In this locked position, the pusher 85 is locked to the anchoring device 81 and the pusher 85 can push or pull the anchoring device 81 to more accurately position the anchoring device 81 during surgery. Only upon pulling the pull wire 86 back out of the locking tube 83 is there a clear path and sufficient space for the ball 90 to be aligned with and released from the locking tube 83 and for the anchoring device 81 to be unlocked or disconnected from the pusher 85. Meanwhile, retracting the pull wire 86 to unlock the anchoring device 81 requires only a relatively small pull force, since the locking force relies mainly on the short wire 89, which takes most of the load when the mechanism is locked.

The pull wire 86 also need only travel a short distance to be removed from the locking tube 83. For example, unlocking the anchoring device 81 from the pusher 85 may only involve retracting the pull wire 86 by about 10 mm to remove the pull wire 86 from the locking tube 83 and to allow the spherical ball 90 to be released. In other embodiments, the anchoring device 81 may be unlocked from the pusher 85 by retracting the pull wire 86 by between about 6 mm and about 14 mm, such as between about 7 mm and about 13 mm, such as between about 8 mm and about 12 mm, such as between about 9 mm and about 11 mm. In certain embodiments, the anchoring device 81 may be unlocked from the pusher 85 by retracting the pull wire 86 less than 6 mm or more than 14 mm. The embodiment of FIGS. 17A-17D provides a robust and reliable locking mechanism which can achieve a strong locking force, while at the same time only needing a small pull force to unlock and detach the components from one another.

In use, the ball locking mechanism 84 can be assembled with the anchoring device 81, for example, as seen in FIG. 17C, prior to implantation. After a distal section of a delivery catheter is positioned at or near a native valve annulus, for example, at a mitral valve annulus, using one of the techniques described with respect to FIGS. 8, 9A-9U, and 10 above, the pusher 85 can push the anchoring device 81 through the delivery catheter to deploy the anchoring device 81. The user can then use the pusher 85 to further retract and/or advance the anchoring device 81 at the native valve annulus in order to more accurately position the anchoring device 81 at the implant site. Once the anchoring device 81 is accurately positioned, the pull wire 86 can be retracted from the locking tube 83, as shown in FIG. 17B, and the spherical ball 90 can then also be retracted and released from the locking tube 83, as shown in FIG. 17A, thereby detaching the anchoring device 81 from the ball locking mechanism 84. The pusher 85 can then be removed from the implant site.

Figure 18C:
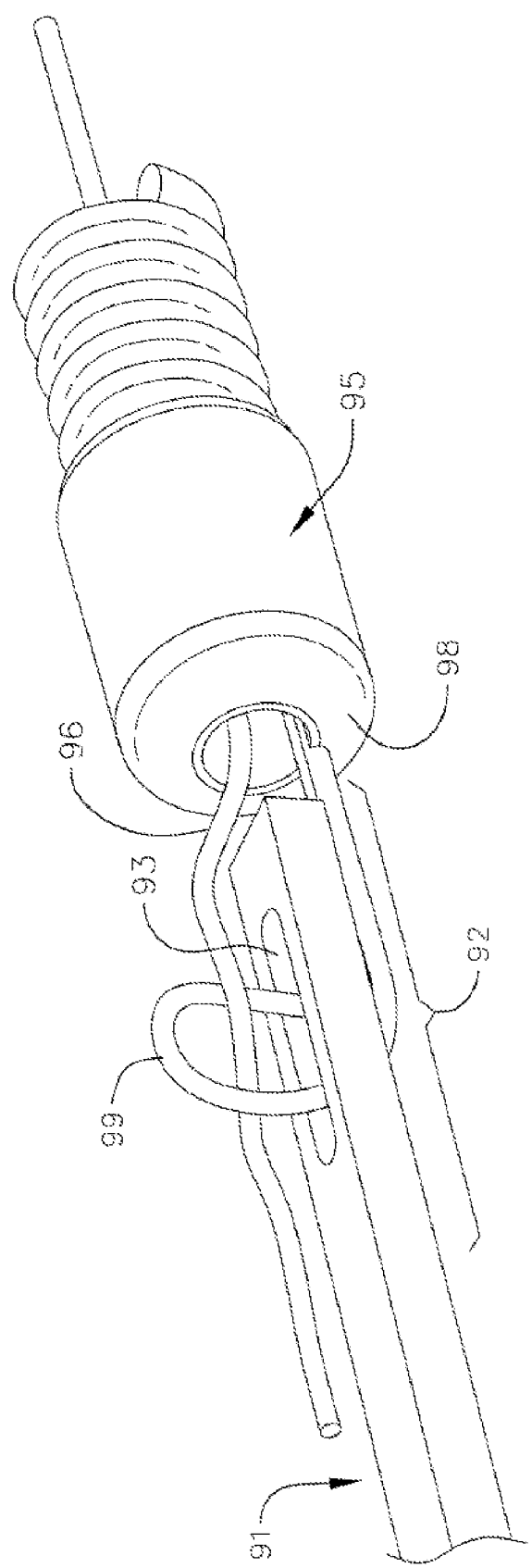

FIGS. 18A-18C show perspective views of a proximal end 92 of an anchoring device 91 and a loop locking mechanism 94, according to an embodiment of the invention. The anchoring device 91 can be similar to the anchoring device embodiments described above, with the addition of the modified proximal end 92, as seen in FIG. 18A. The proximal end 92 of the anchoring device 91 has an elongate proximal hole or slot 93, and the loop locking mechanism 94 includes a pusher 95 and a side wire or pull wire 96 that interact with the hole 93. The pusher 95 includes a flexible tube 97 which can be long enough to extend through the delivery catheter during deployment of the anchoring device 91. The pull wire 96 extends through the pusher 95 and can protrude through the distal end of the pusher 95 with a length that allows the pull wire 96 to engage a wire loop 99, as discussed in greater detail below. The pusher 95 has a distal tip 98 and a wire loop 99 connected to and/or extending from the pusher tip 98. In this embodiment, the loop 99 extends distally from the distal tip 98 of the pusher 95, and has a distalmost loop portion that extends perpendicularly to a longitudinal axis of the pusher 95, generally. While in this embodiment the wire loop 99 is shown as being a wire, such as a cylindrical metal wire, the invention is not so limited. In other embodiments, the loop 99 can also be made, for example, from a flat piece of metal or other material that is laser cut, can be formed by using a suture, or can take any other suitable form that is capable of entering slot 93 of the anchoring device 91 and receiving pull wire 96 to secure the anchoring device 91 to the pusher 95.

The hole 93 at the proximal end 92 of the anchoring device 91 is sized to receive the end of the wire loop 99, as shown in FIG. 18B. When the wire loop 99 is threaded and passed through the hole 93, an end of the wire loop 99 extends out past an opposite side of the hole 93, such that the loop 99 is exposed or protrudes from the opposite side. The loop 99 should be able to protrude from the opposite side of the hole 93 by an amount that is sufficient to allow the pull wire 96 to be inserted or threaded through the loop 99, as shown in FIG. 18C. Then, by passing the pull wire 96 through the loop 99, as shown in FIG. 18C, the anchoring device 91 can attach to or engage the pusher 95 in a locked position, where the pusher 95 can push or pull the anchoring device 91 to more accurately position the anchoring device 91 during surgery. In this locked position, the pull wire 96 anchors the loop 99 in position and prevents the loop 99 from being retracted back out of the hole 93. Only upon pulling the pull wire 96 back out of the loop 99 can the loop 99 be detached from the hole 93 and for the anchoring device 91 to be unlocked or disconnected from the pusher 95. Meanwhile, retracting the pull wire 96 to unlock the anchoring device 91 requires only a relatively small pull force, since the locking force relies mainly on the loop 99, which takes most of the load when the mechanism is locked.

The loop locking mechanism 94 relies on the interaction between the loop 99 of the pusher 95 and the pull wire 96. Therefore, the loop 99 should have a length that is, on one hand, long or tall enough to protrude from a side of the hole 93 opposite the side of insertion to leave sufficient room for the pull wire 96 to be passed through and on the other hand, short enough to reduce vertical shifting when locked, in order to maintain a tight connection between the pusher 95 and the anchoring device 91. Therefore, the embodiment in FIGS. 18A-18C also provide a robust and reliable locking mechanism which can achieve a strong locking force, while also only needing a small pull force and a small amount of retraction by the pull wire 96 for unlocking the components. For example, unlocking the anchoring device 91 from the pusher 95 may only involve retracting the pull wire 96 by about 10 mm to remove the pull wire 96 from the loop 99 and to allow the loop 99 to be released. In other embodiments, the anchoring device 91 may be unlocked from the pusher 95 by retracting the pull wire 96 by between about 6 mm and about 14 mm, such as between about 7 mm and about 13 mm, such as between about 8 mm and about 12 mm, such as between about 9 mm and about 11 mm. In certain embodiments, the anchoring device 91 may be unlocked from the pusher 95 by retracting the pull wire 86 less than 6 mm or more than 14 mm.

In use, the loop locking mechanism 94 can be assembled with the anchoring device 91, as seen in FIG. 18C, prior to surgery. After a distal section of a delivery catheter is positioned at or near a native valve annulus, for example, at a mitral valve annulus, using one of the techniques described with respect to FIGS. 8, 9A-9U, and 10 above, the pusher 95 can push the anchoring device 91 through the delivery catheter to deploy the anchoring device 91. The user can then use the pusher 95 to further retract and/or advance the anchoring device 91 at the native valve annulus in order to more accurately position the anchoring device 91 at the implant site. Once the anchoring device 91 is accurately positioned, the pull wire 96 can be retracted out of the loop 99, as shown in FIG. 18B, and the loop 99 can then be retracted out of the hole 93, as shown in FIG. 18A, thereby detaching the anchoring device 91 from the loop locking mechanism 94. The pusher 95 can then be removed from the implant site.

Additional pushers and retrieval devices and other systems, devices, components, methods, etc. are disclosed in U.S. provisional patent application Ser. No. 62/436,695, filed on Dec. 20, 2016 and U.S. Provisional Patent Application Ser. No. 62/560,962, filed on Sep. 20, 2017 and the related PCT Patent Application Serial No. PCT/US2017/066865 titled "SYSTEMS AND MECHANISMS FOR DEPLOYING A DOCKING DEVICE FOR A REPLACEMENT HEART VALVE" filed on Dec. 15, 2017 (that claims priority to the foregoing provisional applications) each of the foregoing applications is incorporated herein by reference in its entirety. Any of the embodiments and methods disclosed in the foregoing applications can be used with any of the embodiments and methods disclosed by the present application mutatis mutandis.

The various manipulations and controls of the systems and devices described herein can be automated and/or motorized. For example, the controls or knobs described above can be buttons or electrical inputs that cause the actions described with respect to the controls/knobs above. This can be done by connecting (directly or indirectly) some or all of the moving parts to a motor (e.g., an electrical motor, pneumatic motor, hydraulic motor, etc.) that is actuated by the buttons or electrical inputs. For example, the motor can be configured, when actuated, to cause the control wires or pull wires described herein to tension or relax to move the distal region of the catheter. Additionally or alternatively, the motor could configured, when actuated, to cause the pusher to move translationally or axially relative to the catheter to cause an anchoring or docking device to move within and/or into or out of the catheter. Automatic stops or preventative measures could be built in to prevent damage to the system/device and/or patient, e.g., to prevent movement of a component beyond a certain point.

It should be noted that the devices and apparatuses described herein can be used with other surgical procedures and access points (e.g., transapical, open heart, etc.). It should also be noted that the devices described herein (e.g., the deployment tools) can also be used in combination with various other types of anchoring devices and/or prosthetic valves different from the examples described herein.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved. Features, elements, or components of one embodiment can be combined into other embodiments herein.

Although the operations of some of the disclosed embodiments are described in a particular, sequential order for convenient presentation, it should be understood that this manner of description encompasses rearrangement, unless a particular ordering is required by specific language. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art. Steps of various methods herein can be combined.

In view of the many possible embodiments to which the principles of the disclosure can be applied, it should be recognized that the illustrated embodiments are only preferred examples of the invention and should not be taken as limiting the scope of the disclosure. Rather, the scope of the disclosure is defined by the following claims.

What is claimed is:

1. A delivery catheter for delivering a device to a native valve of a patient's heart, comprising:
   a flexible tube having a main lumen and a control wire lumen;
   a plurality of links disposed in a distal region of the flexible tube;
   wherein each link is aligned with and connected to at least one adjacent link with a slot formed between each pair of adjacent links; and
   wherein a top portion of each link is narrower than a bottom portion of each link and each link has a general shape of an acute trapezoid when the links are viewed from a side; and
   a control wire in the control wire lumen that is connected to the plurality of links;
   wherein applying tension to the control wire causes the distal region of the flexible tube to bend; and
   wherein each of the plurality of links comprises at least two opposing side teeth and at least two grooves, and wherein each tooth is received by corresponding groove of an adjacent link when the distal region of the flexible tube is bent and the at least two opposing side teeth are at least partially inserted into the corresponding groove of the adjacent link when the distal region of the flexible tube is not bent; and
   wherein each link further comprises a top tooth and a top groove, wherein the top tooth is received by a corresponding top groove of an adjacent link when the distal region of the flexible tube is bent and the top tooth is separated from the corresponding top groove of the adjacent link by a gap when the distal region of the flexible tube is not bent.

2. The delivery catheter of claim 1 wherein each link is connected to at least one adjacent link only at the bottom portion of the links.

3. The delivery catheter of claim 1 wherein the top portions of the links are drawn closer together when tension is applied to the control wire to bend the distal region.

4. The delivery catheter of claim 1 wherein the plurality of links are in a straight configuration when tension is removed from the control wire.

5. The delivery catheter of claim 1 wherein the flexible tube further comprises a polymer coating.

6. The delivery catheter of claim 1 wherein the flexible tube further comprises a polyether block amide coating.

7. The delivery catheter of claim 1 wherein the plurality of links are comprised of at least one of a shape memory material, stainless steel, or a polymer.

8. The delivery catheter of claim 1, wherein a bottom of each link includes at least one slit to allow for more flexing of the links relative to one another.

9. The delivery catheter of claim 1 wherein the links are cut from a single tube.

10. The delivery catheter of claim 1 wherein the links are cut from a single flat sheet of material that is rolled to form the links.

11. The delivery catheter of claim 1 wherein the control wire extends distally past the links and is attached to the distal region by a ring.

12. The delivery catheter of claim 1 further comprising:
a first ring in a distal region of the flexible tube; and
a second ring in the distal region of the flexible tube that is spaced apart from the first ring;
wherein the plurality of links are disposed in the distal region of the flexible tube between the first ring and the second ring.

13. The delivery catheter of claim 12 wherein the control wire is moveably coupled to the second ring.

14. The delivery catheter of claim 1 further comprising a coil sleeve disposed in the control wire lumen around the control wire.

15. The delivery catheter of claim 14 wherein the coil sleeve extends proximally from the distal region of the flexible tube such that a portion of the control wire that extends from the second ring and to the first ring is not covered by the coil sleeve.

16. A delivery catheter for delivering a device to a native valve of a patient's heart, comprising:
a flexible tube having a main lumen and a control wire lumen;
a first ring in a distal region of the flexible tube;
a second ring in the distal region of the flexible tube that is spaced apart from the first ring;
a control wire in the control wire lumen that is connected to the first ring;
a plurality of links disposed in the distal region of the flexible tube between the first ring and the second ring, wherein each link has a general shape of an acute trapezoid when the links are viewed from a side; and
a coil sleeve disposed in the control wire lumen around the control wire;
wherein the coil sleeve extends proximally from the distal region of the flexible tube such that a portion of the control wire that extends from the second ring and to the first ring is not covered by the coil sleeve;
wherein applying tension to the control wire causes the distal region of the flexible tube to bend; and
wherein each of the plurality of links comprises at least two opposing side teeth and at least two grooves, and wherein each tooth is received by corresponding groove of an adjacent link when the distal region of the flexible tube is bent and the at least two opposing side teeth are at least partially inserted into the corresponding groove of the adjacent link when the distal region of the flexible tube is not bent; and
wherein each link further comprises a top tooth and a top groove, wherein the top tooth is received by a corresponding top groove of an adjacent link when the distal region of the flexible tube is bent and the top tooth is separated from the corresponding top groove of the adjacent link by a gap when the distal region of the flexible tube is not bent.

17. The delivery catheter of claim 16 wherein each link is connected to at least one adjacent link only at a bottom portion of the links.

18. The delivery catheter of claim 16 a top portion of each link is narrower than a bottom portion of each link when the links are viewed from a side.

19. The delivery catheter of claim 18 wherein the top portions of the links are drawn closer together when tension is applied to the control wire to bend the distal region.

20. The delivery catheter of claim 16 wherein the plurality of links are in a straight configuration when tension is removed from the control wire.

21. The delivery catheter of claim 16 wherein the flexible tube further comprises a polymer coating.

22. The delivery catheter of claim 16 wherein the flexible tube further comprises a polyether block amide coating.

23. The delivery catheter of claim 16 wherein the plurality of links are comprised of at least one of a shape memory material, stainless steel, or a polymer.

24. The delivery catheter of claim 16 wherein a bottom of each link includes at least one slit to allow for more flexing of the links relative to one another.

25. The delivery catheter of claim 16 wherein the control wire is moveably coupled to the second ring.

26. The delivery catheter of claim 16 wherein the plurality of links are cut from a single tube, such that each link is aligned with and connected to at least one adjacent link with a slot formed between each pair of adjacent links.

27. The delivery catheter of claim 16 wherein the plurality of links are cut from a single flat sheet and rolled, such that each link is aligned with and connected to at least one adjacent link with a slot formed between each pair of adjacent links.

28. The delivery catheter of claim 16 wherein the control wire can extend distally past the links and can be attached to the distal region by welding or other attachment means at least at one connection point in the distal region.

29. A delivery catheter for delivering a device to a native valve of a patient's heart, comprising:
a flexible tube having a centered main lumen and a control wire lumen;
a first ring in a distal region of the flexible tube;
a second ring in the distal region of the flexible tube that is spaced apart from the first ring;
a control wire in the control wire lumen that is connected to the first ring;
a plurality of links disposed in the distal region of the flexible tube between the first ring and the second ring, wherein each link has a general shape of an acute trapezoid when the links are viewed from a side;
wherein the plurality of links are cut from a single piece of material, such that each link is aligned with and connected to at least one adjacent link with a slot formed between each pair of adjacent links; and
a coil sleeve disposed in the control wire lumen around the control wire;
wherein the coil sleeve extends proximally from the distal region of the flexible tube such that a portion of the control wire that extends from the second ring and to the first ring is not covered by the coil sleeve;
wherein applying tension to the control wire causes the distal region of the flexible tube to bend, and each of the plurality of links comprises at least two opposing teeth and at least two grooves, and wherein each tooth is received by corresponding groove of an adjacent link when the distal region of the flexible tube is bent; and
wherein the device is advanced in a straightened configuration through the central lumen of the flexible tube while the distal region of the flexible tube is bent and assumes a coiled configuration outside of the delivery catheter.

30. The delivery catheter of claim 29 wherein each link is connected to at least one adjacent link only at a bottom portion of the links.

31. The delivery catheter of claim 29 wherein a top portion of each link is narrower than a bottom portion of each link when the links are viewed from a side.

32. The delivery catheter of claim 31 wherein the top portions of the links are drawn closer together when tension is applied to the control wire to bend the distal region.

33. The delivery catheter of claim 29 wherein the plurality of links are in a straight configuration when tension is removed from the control wire.

34. The delivery catheter of claim 29 wherein the flexible tube further comprises a polymer coating.

35. The delivery catheter of claim 29 wherein the flexible tube further comprises a polyether block amide coating.

36. The delivery catheter of claim 29 wherein the plurality of links are comprised of at least one of a shape memory material, stainless steel, or a polymer.

37. The delivery catheter of claim 29, wherein a bottom of each link includes at least one slit to allow for more flexing of the links relative to one another.

38. The delivery catheter of claim 29 the control wire is moveably coupled to the second ring.

39. The delivery catheter of claim 29 wherein the links are cut from a single tube.

40. The delivery catheter of claim 29 wherein the links are cut from a single flat sheet of material that is rolled to form the links.

41. The delivery catheter of claim 29 wherein the control wire can extend distally past the links and can be attached to the distal region by welding or other attachment means at least at one connection point in the distal region.

* * * * *